(12) United States Patent
Björsne et al.

(10) Patent No.: US 7,144,914 B2
(45) Date of Patent: Dec. 5, 2006

(54) 3,7-DIAZABICYCLO[3.3.0]OCTANES AND THEIR USE IN THE TREATMENT OF CARDIAC ARRHYTHMIAS

(75) Inventors: Magnus Björsne, Mölndal (SE); Fritiof Pontén, Mölndal (SE); Gert Strandlund, Mölndal (SE); Peder Svensson, Göteborg (SE); Michael Wilstermann, Mölndal (SE)

(73) Assignee: Astrazeneca AB, Sodertalje (SE)

( * ) Notice: Subject to any disclaimer, the term of this patent is extended or adjusted under 35 U.S.C. 154(b) by 220 days.

(21) Appl. No.: 10/467,043

(22) PCT Filed: Jan. 29, 2002

(86) PCT No.: PCT/SE02/00152

§ 371 (c)(1),
(2), (4) Date: Jul. 31, 2003

(87) PCT Pub. No.: WO02/060902

PCT Pub. Date: Aug. 8, 2002

(65) Prior Publication Data

US 2004/0053986 A1    Mar. 18, 2004

(30) Foreign Application Priority Data

Feb. 2, 2001  (SE) ................................. 0100326

(51) Int. Cl.
*A61K 31/407* (2006.01)
*C07D 487/02* (2006.01)
(52) U.S. Cl. ....................................... 514/412; 548/453
(58) Field of Classification Search .............. 548/453; 514/412
See application file for complete search history.

(56) References Cited

U.S. PATENT DOCUMENTS

| | | | |
|---|---|---|---|
| 3,962,449 A | 6/1976 | Binning et al. | |
| 4,459,301 A | 7/1984 | Binnig et al. | |
| 4,550,112 A | 10/1985 | Schoen et al. | |
| 4,556,662 A | 12/1985 | Binnig et al. | |
| 5,468,858 A | 11/1995 | Berlin et al. | |
| 6,107,321 A * | 8/2000 | Madin | 514/383 |
| 6,355,641 B1 * | 3/2002 | Coffen et al. | 514/252.18 |

FOREIGN PATENT DOCUMENTS

| | | |
|---|---|---|
| DE | 39 30 266 A1 | 3/1991 |
| EP | 0 306 871 A2 | 3/1989 |
| EP | 0 308 843 A2 | 3/1989 |
| EP | 0 665 228 A1 | 8/1995 |
| EP | 0 728 758 A1 | 8/1996 |
| WO | WO-91/07405 A1 | 5/1991 |
| WO | WO-95/13279 A1 | 5/1995 |
| WO | WO-95/15327 A1 | 6/1995 |
| WO | WO-96/07656 A1 | 3/1996 |
| WO | WO-96/35691 A1 | 11/1996 |
| WO | WO-97/10223 A1 | 3/1997 |
| WO | WO-97/11945 A1 | 4/1997 |
| WO | WO-98/06725 A1 | 2/1998 |
| WO | WO-99/31100 A1 | 6/1999 |
| WO | WO 01/04107 * | 1/2001 |
| WO | WO-01/04107 A1 | 1/2001 |

OTHER PUBLICATIONS

Coffen et al, STN International, CAPLUS Database, Columbus, OH, Accession No. 2000:666717, Reg. No. 295341-40-1 (2005).*
Stolle et al, STN International, HCAPLUS Database, Columbus, OH, Accession No., 2001:50635, Reg. No. 321129-97-9 (2006).*
Obst, U., et al., "Synthesis of Novel Nonpeptidic Thrombin Inhibitors," Helvetica Chimica Acta, vol. 83, 855-909 (2000).
Marko, I.E., et al., "Asymmetric Grignard Addition to Aldehydes. An Example of Inverse Temperature Dependence of Enantiomeric Excess," Tetrahedron Asymmetry, vol. 5 (4), 569-572 (1994).
Obst. U., et al., "Molecular recognition at the thrombin active site: structure-based design and synthesis of potent and selective thrombin inhibitors and the X-ray crystal structures of two thrombin-inhibitor complexes," Chemistry & Biology, vol. 4 (4), 287-295 (1997).
Obst, U., et al., "Design of Novel, Nonpeptidic Thrombin Inhibitors and Structure of a Thrombin—Inhibitor Complex," Angew. Chem. Int. Ed. Engl., vol. 34 (16), 1739-1742 (1995).
"Special Report—Preliminary Report: Effect of Encainide and Flecainide on Mortality in a Randomized Trial of Arrhythmia Suppression After Myocardial Infarction," New England Journal of Medicine, vol. 321 (6), 406-412 (1989).
Garrison, G.L., et al., "Novel 3,7-Diheterabicyclo[3.3.1]nonanes That Possess Predominant Class III Antiarrhythmic Activity in 1-4 Day Post Infarction Dog Models: X-ray Diffraction Analysis of 3-[4-(1H-Imidazol-1-yl)benzoyl]-7-isopropyl-3,7-diazabicyclo[3.3.1]nonane Dihydroperchlorate," J. Med. Chem., vol. 39, 2559-2570 (1996).
Paroczai, M., et al., "Investigations to Characterize a New Antiarrhythmic Drug Bisaramil," Pharmacol. Res., vol. 24 (2), 149-162 (1991).

(Continued)

Primary Examiner—Joseph K. McKane
Assistant Examiner—Andrew B. Freistein
(74) Attorney, Agent, or Firm—Anneli Jonsson; Cozen O'Connor, P.C.

(57) ABSTRACT

There is provided compounds of formula (I) wherein $R^1$ to $R^4$, $R^a$ to $R^f$, A and B have meanings given in the description, which are useful in the prophylaxis and in the treatment of arrhythmias, in particular atrial and ventricular arrhythmias.

29 Claims, No Drawings

OTHER PUBLICATIONS

Wang, J., et al., "Class III Antiarrhythmic Drug Action in Experiemental Atrial Fibrillation, Differences in Reverse Use Dependence and Effectiveness Between d-Sotalol and the New Antiarrhythmic Drug Ambasilide," Circulation, vol. 90 (4), 2032-2040 (1994).

Chen, C.L., et al., "High-Performance Liquid Chromatographic Determination of SAZ-VII-22, a Novel Antiarrhythmic Agent, in Dog Plasma and Urine," Analytical Sciences, vol. 9, 429-431 (1993).

Abou-Gharbia, M., et al., "Synthesis and Structure-Activity Relationship of Substituted Tetrahydro- and Hexahydro-1,2-benzisothiazol-3-one 1,1-Dioxides and Thiadiazinones: Potential Anxiolytic Agents," J. Med. Chem., vol. 32, 1024-1033 (1989).

Ohnmacht, C.J., et al., "Synthesis and Carbon-13 NMR Study of 2-Benzyl, 2-Methyl, 2-Aryloctahydropyrrolo[3,4-c]pyrroles and the 1,2,3,5-Tetrahydropyrrolo[3,4-c]pyrrole Ring System," J. Heterocyclic Chem., vol. 20, 321-329 (1983).

Knowles, P., et al., "A Synthesis of 3,7,10-Triazatricyclo [3.3.3.01.5]undecane, '3,7,10-Triaza[3.3.3]propellane', and some Derivatives," J. Chem. Soc. Perkin Trans. I, 1475-1477 (1983).

Altman, J., et al., "Propellanes-I Tricyclic Compounds Conjoined in a Carbon-Carbon Single Bond," Tetrahedron, Suppl. 8, Part I, 279-304 (1966).

Dave, P.R., et al., "Facile Preparation of 3,7-Diazabicyclo[3.3.0]octane and 3,7,10-Triheterocyclic [3.3.3]Propellane Ring Systems from 1,5-Diazacyclooctane 3,7-Derivatives," J. Org. Chem., vol. 61 (25), 8897-8903 (1996).

Padwa, A., et al., "Diastereofacial Selectivity in Azomethine Ylide Cycloaddition Reactions Derived from Chiral a-Cyanoaminosilanes," Tetrahedron, vol. 41 (17), 3529-3535 (1985).

Axenborg, J.E., et al., "A PC-based on-line system for physiological in vivo and in vitro experiments," Comput. Methods Programs Biomed., vol. 41, 55-67 (1993).

Weinges, K., et al., "Synthesen von 3.7-Dihetero-bicyclo[3.3.0]octanen," Chem. Ber., vol. 101, 3010-3017 (1968).

* cited by examiner

3,7-DIAZABICYCLO[3.3.0]OCTANES AND THEIR USE IN THE TREATMENT OF CARDIAC ARRHYTHMIAS

CROSS-REFERENCE TO RELATED APPLICATIONS

This application is a national stage filing under 35 U.S.C. 371 of International Application PCT/SE02/00152, filed Jan. 29, 2002, which claims priority from Sweden Application No. 0100326-8, filed Feb. 2, 2001, the specifications of each of which are incorporated by reference herein. International Application PCT/SE02/00152 was published under PCT Article 21(2) in English.

FIELD OF THE INVENTION

This invention relates to novel pharmaceutically useful compounds, in particular compounds which are useful in the treatment of cardiac arrhythmias.

BACKGROUND AND PRIOR ART

Cardiac arrhythmias may be defined as abnormalities in the rate, regularity, or site of origin of the cardiac impulse or as disturbances in conduction which causes an abnormal sequence of activation. Arrhythmias may be classified clinically by means of the presumed site of origin (i.e. as supraventricular, including atrial and atrioventricular, arrhythmias and ventricular arrhythmias) and/or by means of rate (i.e. bradyarrhythmias (slow) and tachyarrhythmias (fast)).

In the treatment of cardiac arrhythmias, the negative outcome in clinical trials (see, for example, the outcome of the Cardiac Arrhythmia Suppression Trial (CAST) reported in *New England Journal of Medicine* 321, 406 (1989)) with "traditional" antiarrhythmic drugs, which act primarily by slowing the conduction velocity (class I antiarrhythmic drugs), has prompted drug development towards compounds which selectively delay cardiac repolarization, thus prolonging the QT interval. Class III antiarrhythimic drugs may be defined as drugs which prolong the trans-membrane action potential duration (which can be caused by a block of outward $K^+$ currents or from an increase of inward ion currents) and refractoriness, without affecting cardiac conduction.

One of the key disadvantages of hitherto known drugs which act by delaying repolarization (class III or otherwise) is that they all are known to exhibit a unique form of proarrhythmia known as torsades de pointes (turning of points), which may, on occasion be fatal. From the point of view of safety, the minimisation of this phenomenon (which has also been shown to be exhibited as a result of administration of non-cardiac drugs such as phenothiazines, tricyclic antidepressants, antihistamines and antibiotics) is a key problem to be solved in the provision of effective antiarrhythmic drugs.

Antiarrhythmic drugs based on bispidines (3,7-diazabicyclo[3.3.1]nonanes), are known from inter alia international patent applications WO 91/07405 and WO 99/31100, European patent applications 306 871, 308 843 and 665 228 and U.S. Pat. Nos. 3,962,449, 4,556,662, 4,550,112, 4,459, 301 and 5,468,858, as well as journal articles including inter alia: *J. Med. Chem.* 39, 2559, (1996); *Pharmacol. Res.* 24, 149 (1991); *Circulation* 90, 2032 (1994); and *Anal. Sci.* 9, 429, (1993). Compounds based on 3,7-diazabicyclo[3.3.0] octane are neither disclosed nor suggested in any of these documents.

Compounds based on 3,7-diazabicyclo[3.3.0]octane are known for use in a variety of medical applications, including, inter alia as: anti-migraine agents (as described in WO 98/06725 and WO 97/11945); antibiotics (as described in WO 97/10223 and WO 96/35691); neuroleptics (as described in WO 95/15327 and WO 95/13279); serotonin reuptake inhibitors (as described in WO 96/07656); thrombin inhibitors (as described in *Helvetica Chim. Acta* 83, 855 (2006), *Chem. & Biol.* 4, 287 (1997) and *Angew. Chem. Int. Ed. Eng.* 34, 1739 (1995)); and anxiolytic agents (as described in *J. Med. Chem.* 32, 1024 (1989)). Further, compounds based on 3,7-diazabicyclo[3.3.0]octane have been used in the treatment of, inter alia, gastrointestinal disorders (as described in DE 39 30 266 A1) and diseases caused by malfunction of the glutaminergic system (as described in WO 01/04107).

Other 3,7-diazabicyclo[3.3.0]octane compounds are known as chemical curiosities from inter alia *J. Heterocyclic. Chem.* 20, 321 (1983), *Chem. Ber.* 101, 3010 (1968), *J. Chem. Soc., Perkin Trans. I* 1475 (1983), *Tetrahedron, Suppl.* 8 Part I, 279 (1966) and *J. Org. Chem.* 61, 8897 (1996). Further, 3,7-bis(1-phenylethyl)-3,7-diazabicyclo [3.3.0]octane is known to be useful in controlling the enantioselectivity of reactions between Grignard reagents and aldehydes (as described in *Tetrahedron* 5, 569 (1994)).

None of the prior art documents mentioned above that relate to 3,7-diazabicyclo[3.3.0]octanes disclose or provide any suggestion that the compounds disclosed therein may be useful in the treatment of cardiac arrhythmias.

We have surprisingly found that a novel group of 3,7-diazabicyclo[3.3.0]-octane-based compounds exhibit electrophysiological activity, preferably class III electrophysiological activity, and are therefore expected to be useful in the treatment of cardiac arrhythmias.

DISCLOSURE OF THE INVENTION

According to the invention there is provided compounds of formula I,

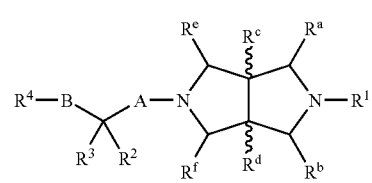

I wherein the wavy lines represent optional relative cis- or trans-stereochemistry;

$R^1$ represents $C_{1-12}$ alkyl (optionally substituted and/or terminated by one or more groups selected from halo, cyano, nitro, aryl, $Het^1$, $-C(O)R^{5a}$, $-OR^{5b}$, $-N(R^6)R^{5c}$, $-C(O)XR^7$, $-C(O)N(R^8)R^{5d}$ and $-S(O)_2R^9$), $Het^2$, $-C(O)R^{5a}$, $-C(O)XR^7$, $-C(O)N(R^8)R^{5d}$ or $-S(O)_2 R^9$; p0 $R^{5a}$ to $R^{5d}$ independently represent, at each occurrence when used herein, H, $C_{1-6}$ alkyl (optionally substituted and/or terminated by one or more substituents selected from $-OH$, $C_{1-6}$ alkoxy, halo, cyano, nitro, aryl, $Het^3$ and $-NHC(O)R^{10}$), aryl or $Het^4$, or $R^{5d}$, together with $R^8$, represents $C_{3-6}$ alkylene (which alkylene group is optionally interrupted by an O atom and/or is optionally substituted by one or more $C_{1-3}$ alkyl groups);

$R^{10}$ represents H, $C_{1-4}$ alkyl (optionally substituted and/or terminated by one or more substituents selected from halo, cyano, aryl and —NHC(O)$R^{11}$) or aryl;

$R^{11}$ represents H, $C_{1-4}$ alkyl or aryl;

$R^6$ represents H, $C_{1-6}$ alkyl (optionally substituted and/or terminated by one or more substituents selected from —OH, halo, cyano, nitro and aryl), aryl, —C(O)$R^{12a}$, —C(O)O$R^{12b}$ or —C(O)N(H)$R^{12c}$;

$R^{12a}$, $R^{12b}$ and $R^{12c}$ represent $C_{1-6}$ alkyl (optionally substituted and/or terminated by one or more substituents selected from —OH, halo, cyano, nitro and aryl) or aryl, or $R^{12a}$ and $R^{12c}$ represent H;

X represents O or S;

$R^7$ represents, at each occurrence when used herein, aryl or $C_{1-12}$ alkyl (which alkyl group is optionally substituted and/or terminated by one or more substituents selected from —OH, halo, cyano, nitro, aryl, $C_{1-6}$ alkoxy, —SO$_2$$R^{13a}$, —C(O)$R^{13b}$ and Het$^5$);

$R^{13a}$ and $R^{13b}$ independently represent $C_{1-6}$ alkyl or aryl;

$R^8$ represents, at each occurrence when used herein, H, $C_{1-12}$ alkyl, $C_{1-6}$ alkoxy (which latter two groups are optionally substituted and/or terminated by one or more substituents selected from —OH, halo, cyano, nitro, $C_{1-4}$ alkyl and $C_{1-4}$ alkoxy), —D-aryl, —D-aryloxy, —D-Het$^6$, —D—N(H)C(O)$R^{14a}$, —D—S(O)$_2$$R^{15a}$, —D—C(O)$R^{14b}$, —D—C(O)O$R^{15b}$, —D—C(O)N($R^{14c}$)$R^{14d}$, or $R^8$, together with $R^{5d}$, represents $C_{3-6}$ alkylene (which alkylene group is optionally interrupted by an O atom and/or is optionally substituted by one or more $C_{1-3}$ alkyl groups);

$R^{14a}$ to $R^{14d}$ independently represent H, $C_{1-6}$ alkyl (optionally substituted and/or terminated by one or more substituents selected from —OH, halo, cyano, nitro and aryl), aryl, or $R^{14c}$ and $R^{14d}$ together represent $C_{3-6}$ alkylene;

$R^{15a}$ and $R^{15b}$ independently represent $C_{1-6}$ alkyl (optionally substituted and/or terminated by one or more substituents selected from —OH, halo, cyano, nitro and aryl) or aryl;

D represents a direct bond or $C_{1-6}$ alkylene;

$R^9$ represents, at each occurrence when used herein, $C_{1-6}$ allyl (optionally substituted and/or terminated by one or more substituents selected from —OH, halo, cyano, nitro and aryl), aryl or Het$^7$;

$R^2$ represents H, halo, $C_{1-6}$ alkyl, —E—O$R^{16}$, —E—N($R^{17}$)$R^{18}$ or, together with $R^3$, represents =O;

$R^3$ represents H, $C_{1-6}$ alkyl or, together with $R^2$, represents =O;

$R^{16}$ represents H, $C_{1-6}$ alkyl, —E-aryl, —E-Het$^8$, —C(O)$R^{19a}$, —C(O)O$R^{19b}$ or —C(O)N($R^{20a}$)$R^{20b}$;

$R^{17}$ represents H, $C_{1-6}$ alkyl, —E-aryl, —E-Het$^8$, —C(O)$R^{19a}$, —C(O)O$R^{19b}$, —S(O)$_2$$R^{19c}$, —[C(O)]$^p$N($R^{20a}$)$R^{20b}$ or —C(NH)NH$_2$;

$R^{18}$ represents H, $C_{1-6}$ alkyl, —E-aryl or —C(O)$R^{19d}$;

$R^{19a}$ to $R^{19d}$ independently represent, at each occurrence when used herein, $C_{1-6}$ alkyl (optionally substituted and/or terminated by one or more substituents selected from halo, aryl and Het$^9$), aryl, Het$^{10}$, or $R^{19a}$ and $R^{19d}$ independently represent H;

$R^{20a}$ and $R^{20b}$ independently represent, at each occurrence when used herein, H or $C_{1-6}$ alkyl (optionally substituted and/or terminated by one or more substituents selected from halo, aryl and Het$^{11}$), aryl, Het$^{12}$, or together represent $C_{3-6}$ alkylene, optionally interrupted by an O atom;

E represents, at each occurrence when used herein, a direct bond or $C_{1-4}$ alkylene;

p represents 1 or 2;

A represents —G—, —J—N($R^{21}$)— or —J—O— (in which latter two groups, N($R^{21}$)— or O— is attached to the carbon atom bearing $R^2$ and $R^3$);

B represents —Z—, —Z—N($R^{22}$)—, —N($R^{22}$)—Z—, —Z—S(O)$_n$—, —Z—O— (in which latter two groups, Z is attached to the carbon atom bearing $R^2$ and $R^3$);

G represents a direct bond or $C_{1-6}$ alkylene;

J represents $C_{2-6}$ alkylene;

Z represents a direct bond or $C_{1-4}$ alkylene;

$R^{21}$ and $R^{22}$ independently represent H or $C_{1-6}$ alkyl;

$R^4$ represents aryl or Het$^{13}$, both of which groups are optionally substituted by one or more substituents selected from —OH, cyano, halo, nitro, $C_{1-6}$ alkyl (optionally terminated by —N(H)C(O)O$R^{23a}$), $C_{1-6}$ alkoxy, Het$^1$, aryl, —N($R^{24a}$)$R^{24b}$, —C(O)$R^{24c}$, —C(O)O$R^{24d}$, —C(O)N($R^{24e}$)$R^{24f}$, —N($R^{24g}$)C(O)$R^{24h}$, —N($R^{24i}$)C(O)N($R^{24j}$)$R^{24k}$, —N($R^{24m}$)S(O)$_2$$R^{23b}$, —S(O)$_n$$R^{23c}$, —OS(O)$_2$$R^{23d}$, —S(O)$_2$N($R^{24n}$)$R^{24p}$ and (in the case of Het$^{13}$ only) oxo;

Het$^{13}$ represents a four- to twelve-membered heterocyclic group containing one or more heteroatoms selected from oxygen, nitrogen and/or sulfur;

Het$^1$ to Het$^{12}$ independently represent, at each occurrence when used herein, four- to twelve-membered heterocyclic groups containing one or more heteroatoms selected from oxygen, nitrogen and/or sulfur, which heterocyclic groups are optionally substituted by one or more substituents including =O, —OH, cyano, halo, nitro, $C_{1-6}$ alkyl (optionally terminated by —N(H)C(O)O$R^{23a}$), $C_{1-6}$ alkoxy, Het$^1$, aryl, —N($R^{24a}$)$R^{24b}$, —C(O)$R^{24c}$, —C(O)O$R^{24d}$, —C(O)N($R^{24e}$)$R^{24f}$, —N($R^{24g}$)C(O)$R^{24h}$, —N($R^{24i}$)C(O)N($R^{24j}$)$R^{24k}$, —N($R^{24m}$)S(O)$_2$$R^{23b}$, —S(O)$_n$$R^{23c}$, —OS(O)$_2$$R^{23d}$ and —S(O)$_2$N($R^{24n}$)$R^{24p}$;

$R^{23a}$ to $R^{23d}$ independently represent, at each occurrence when used herein, $C_{1-6}$ alkyl;

$R^{24a}$ to $R^{24p}$ independently represent, at each occurrence when used herein, H or $C_{1-6}$ alkyl;

n represents, at each occurrence, 0, 1 or 2; and $R^a$ to $R^f$ independently represent H or $C_{1-4}$ alkyl;

wherein each aryl and aryloxy group, unless otherwise specified, is optionally substituted;

or a pharmaceutically acceptable derivative thereof;

provided that:

(a) when $R^3$ represents H or $C_{1-4}$ alkyl; and A represents —J—N($R^{21}$)— or —J—O—; then B does not represent —N($R^{22}$)—, —S(O)$_n$—, —O— or —N($R^{22}$)—Z— (in which latter group —N($R^{22}$) is attached to the carbon atom bearing $R^2$ and $R^3$);

(b) when $R^2$ represents —E—O$R^{16}$ or —E—N($R^{17}$)$R^{18}$ in which E represents a direct bond, then:

(i) A does not represent a direct bond, —J—N($R^{21}$)— or —J—O—; and (ii) B does not represent —N($R^{22}$)—, —S(O)$_n$—, —O— or —N($N^{22}$)—Z— (in which latter group —N($R^{22}$) is attached to the carbon atom bearing $R^2$ and $R^3$);

(c) Het$^1$ and Het$^{13}$ do not represent 9-membered heterocycles that contain a fused benzene or pyridine ring; and (d) the compound is not:

3,7-bis(1-phenylethyl)-3,7-diazabicyclo[3.3.0]octane;

2-{4-(7-benzyl-3,7-diazabicyclo[3.3.0]octan-3-yl)butyl}-1,2-benzisothiazol-3-one-1,1-dioxide;

3-methyl-7-benzyl-3,7-diazabicyclo[3.3.0]octane;

3-cyclohexyl-7-benzyl-3,7-diazabicyclo[3.3.0]octane;

3-(thiazol-2-yl)-7-benzyl-3,7-diazabicyclo[3.3.0]octane;

3-(2-pyrimidyl)-7-benzyl-3,7-diazabicyclo[3.3.0]octane; or 3-(5,5-dimethoxy)pentyl-7-benzyl-3,7-diazabicyclo [3.3.0]octane;

which compounds are referred to hereinafter as "the compounds of the invention".

Unless otherwise specified, alkyl groups and alkoxy groups as defined herein may be straight-chain or, when there is a sufficient number (i.e. a minimum of three) of carbon atoms, be branched-chain and/or cyclic. Further, when there is a sufficient number (i.e. a minimum of four) of carbon atoms, such alkyl and alkoxy groups may also be part cyclic/acyclic. Such allyl and alkoxy groups may also be saturated or, when there is a sufficient number (i.e. a minimum of two) of carbon atoms, be unsaturated and/or interrupted by one or more oxygen and/or sulfur atoms. Unless otherwise specified, alkyl and alkoxy groups may also be substituted by one or more halo, and especially fluoro, atoms.

Unless otherwise specified, alkylene groups as defined herein may be straight-chain or, when there is a sufficient number (i.e. a minimum of two) of carbon atoms, be branched-chain. Such alkylene chains may also be saturated or, when there is a sufficient number (i.e. a minimum of two) of carbon atoms, be unsaturated and/or interrupted by one or more oxygen and/or sulfur atoms. Unless otherwise specified, alkylene groups may also be substituted by one or more halo atoms.

The term "aryl", when used herein, includes $C_{6-10}$ aryl groups such as phenyl, naphthyl and the like. The term "aryloxy", when used herein includes $C_{6-10}$ aryloxy groups such as phenoxy, naphthoxy and the like. For the avoidance of doubt, aryloxy groups referred to herein are attached to the rest of the molecule via the O-atom of the oxy-group. Unless otherwise specified, aryl and aryloxy groups may be substituted by one or more substituents including —OH, cyano, halo, nitro, $C_{1-6}$ alkyl (optionally terminated by —N(H)C(O)OR$^{23a}$), $C_{1-6}$ alkoxy, Het$^1$, aryl (which aryl group may not be substituted with any further aryl groups), —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)$_2$R$^{23d}$ and —S(O)$_2$N(R$^{24n}$)R$^{24p}$ (wherein Het$^1$, R$^{23a}$ to R$^{23d}$, R$^{24a}$ to R$^{24p}$ and n are as hereinbefore defined). When substituted, aryl and aryloxy groups are preferably substituted by between one and three substituents.

The term "halo", when used herein, includes fluoro, chloro, bromo and iodo.

Het (Het$^1$ to Het$^{13}$) groups that may be mentioned include those containing 1 to 4 heteroatoms (selected from the group oxygen, nitrogen and/or sulfur) and in which the total number of atoms in the ring system are between five and twelve. Het (Het$^1$ to Het$^{13}$) groups may be fully saturated, wholly aromatic, partly aromatic and/or bicyclic in character. Heterocyclic groups that may be mentioned include benzodioxanyl, benzodioxepanyl, benzodioxolyl, benzofuranyl, benzofurazanyl, benzimidazolyl, benzomorpholinyl, benzothiophenyl, chromanyl, cinnolnyl, dioxanyl, furanyl, hydantoinyl, imidazolyl, imidazo[1,2-α]pyridinyl, indolyl, isoquinolinyl, isoxazolyl, maleimido, morpholinyl, oxazolyl, phthalazinyl, piperazinyl, piperidinyl, purinyl, pyranyl, pyrazinyl, pyrazolyl, pyridinyl, pyrimindinyl, pyrrolidinonyl, pyrrolidinyl, pyrrolinyl, pyrrolyl, quinazolinyl, quinolinyl, 3-sulfolenyl, tetrahydropyranyl, tetrahydrofuranyl, thiazolyl, thienyl, thiochromanyl, triazolyl and the like. Values of Het$^1$ that may be mentioned include piperazinyl and thiazolyl. Values of Het$^2$ that may be mentioned include thiazolyl. Values of Het$^4$ that may be mentioned include isoxazolyl and tetrahydropyranyl. Values of Het$^5$ that may be mentioned include morpholinyl, piperazinyl and pyridinyl. Values of Het$^6$ that may be mentioned include isoxazolyl and tetrahydropyranyl.

When a Het (Het$^1$ to Het$^{13}$) group is substituted by one or more aryl and/or Het$^1$ group(s), that (those) said aryl and/or Het$^1$ substituent(s) may, not itself (themselves) be substituted by any aryl and/or Het$^1$ group(s). Substituents on Het (Het$^1$ to Het$^{13}$) groups may, where appropriate, be located on any atom in the ring system including a heteroatom. The point of attachment of Het (Het$^1$ to Het$^{13}$) groups may be via any atom in the ring system including (where appropriate) a heteroatom, or an atom on any fused carbocyclic ring that may be present as part of the ring system. Het (Het$^1$ to Het$^{13}$) groups may also be in the N- or S-oxidised form.

Pharmaceutically acceptable derivatives include salts and solvates. Salts which may be mentioned include acid addition salts. Pharmaceutically acceptable derivatives also include, at the 3,8-diazabicyclo[3.2.1]octane or (when a Het (Het$^1$ to Het$^{13}$) group contains a tertiary nitrogen atom) tertiary heterocyclic nitrogens, $C_{1-4}$ alkyl quaternary ammonium salts and N-oxides, provided that when a N-oxide is present:

(a) no Het (Het$^1$ to Het$^{13}$) group contains an unoxidised S-atom; and/or (b) n does not represent 0 when B represents —Z—S(O)$_n$—.

Compounds of formula I may exhibit tautomerism. All tautomeric forms and mixtures thereof are included within the scope of the invention.

Compounds of formula I may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation, or by derivatisation, for example with a homochiral acid followed by separation of the diastereomeric esters by conventional means (e.g. HPLC, chromatography over silica). All stereoisomers are included within the scope of the invention.

Abbreviations are listed at the end of this specification.

Compounds of formula I that may be mentioned include those in which:

$R^1$ represents $C_{1-12}$ alkyl (optionally substituted and/or terminated by one or more groups selected from halo, cyano, nitro, aryl, Het$^1$, —C(O)R$^{5a}$, —OR$^{5b}$, —N(R$^6$)R$^{5c}$, —C(O)XR$^7$, —C(O)N(R$^8$)R$^{5d}$ and —S(O)$_2$R$^9$), —C(O)XR$^7$, —C(O)N(R$^8$)R$^{5d}$ or —S(O)$_2$R$^9$;

$R^{5a}$ to $R^{5d}$ independently represent, at each occurrence when used herein, H, $C_{1-6}$ alkyl (optionally substituted and/or terminated by one or more substituents selected from —OH, $C_{1-6}$ alkoxy, halo, cyano, nitro, aryl, and Het$^3$), aryl or Het$^4$, or R$^{5d}$, together with R$^8$, represents $C_{3-6}$ alkylene (which alkylene group is optionally interrupted by an O atom and/or is optionally substituted by one or more $C_{1-3}$ alkyl groups);

$R^7$ represents, at each occurrence when used herein $C_{1-12}$ alkyl (which group is optionally substituted and/or terminated by one or more substituents selected from —OH, halo, cyano, nitro, aryl, $C_{1-6}$ alkoxy, —SO$_2$R$^{13a}$, —C(O)R$^{13b}$ and Het$^5$);

$R^9$ represents, at each occurrence when used herein, $C_{1-6}$ alkyl (optionally substituted and/or terminated by one or more substituents selected from —OH, halo, cyano, nitro and aryl) or aryl;

$R^2$ represents H, halo, $C_{1-6}$ alkyl, —$OR^{16}$, —E—$N(R^7)R^{18}$ or, together with $R^3$, represents =O;

$R^4$ represents aryl or pyridyl, which groups are optionally substituted by one or more substituents selected from —OH, cyano, halo, nitro; $C_{1-6}$ alkyl (optionally terminated by —N(H)C(O)$OR^{23a}$), $C_{1-6}$ alkoxy, —$N(R^{24a})R^{24b}$, —C(O)$R^{24c}$, —C(O)$OR^{24d}$, —C(O)$N(R^{24e})R^{24f}$, —$N(R^{24g})$C(O)$R^{24h}$, —$N(R^{24i})$C(O)$N(R^{24j})R^{24k}$, —$N(R^{24m})$S(O)$_2R^{23b}$, —S(O)$_nR^{23c}$ and —OS(O)$_2R^{23d}$.

Further compounds that may be mentioned include those in which: $Het^1$ and $Het^{13}$ independently represent 4- to 8-membered heterocyclic groups containing one or more heteroatoms selected from oxygen, nitrogen and/or sulfur, which groups are optionally substituted as hereinbefore defined.

Still further compounds that may be mentioned include those in which:

$R^1$ represents $C_{1-12}$ alkyl (optionally substituted and/or terminated by one or more groups selected from halo, cyano, nitro, aryl, $Het^1$, —$OR^{5b}$, —$N(R^6)R^{5c}$, —C(O)$XR^7$, —C(O)$N(R^8)R^{5d}$ and —S(O)$_2R^9$), $Het^2$, —C(O)$R^{5a}$, —C(O)$XR^7$, —C(O)$N(R^8)R^{5d}$, —S(O)$_2R^9$, —CH$_2$—C(O)-(unsubstituted $C_{1-6}$ alkyl) or —CH$_2$—C(O)-(aryl) (the aryl part of which latter group is optionally substituted by one or more substituents selected from —OH, cyano, halo, nitro, $C_{1-6}$ alkyl (optionally terminated by —N(H)C(O)$OR^{23a}$), $C_{1-6}$ alkoxy, $Het^1$, aryl (which aryl group may not be substituted with any further aryl groups), —N($C_{1-6}$ alkyl)$R^{24b}$, —C(O)$R^{24c}$, —C(O)$OR^{24d}$, —C(O)$N(R^{24e})R^{24f}$, —$N(R^{24g})$C(O)$R^{24h}$, —$N(R^{24i})$C(O)$N(R^{24j})R^{24k}$, —$N(R^{24m})$S(O)$_2R^{23b}$, —S(O)$_nR^{23c}$, —OS(O)$_2R^{23d}$ and —S(O)$_2N(R^{24n})R^{24p}$)

$R^2$ and $R^3$ do not together represent =O;

G does not represent a direct bond; and/or $Het^3$ and $Het^4$ independently represent 4- to 8-membered heterocyclic groups containing one or more heteroatoms selected from oxygen, nitrogen and/or sulfur, which groups are optionally substituted as hereinbefore defined.

Preferred compounds of the invention include those in which:

the wavy lines represent relative cis-stereochemistry;

$R^1$ represents $C_{1-8}$ alkyl (optionally substituted and/or terminated by one or more groups selected from halo, optionally substituted phenyl, $Het^1$, —C(O)$R^{5a}$, —$OR^{5b}$, —C(O)$OR^7$, —C(O)N(H)$R^8$ and —S(O)$_2$—$C_{1-6}$ alkyl), $Het^2$, —C(O)$OR^7$, —C(O)N(H)$R^8$ or —S(O)$_2R^9$;

$R^{5a}$ and $R^{5b}$ independently represent, at each occurrence when used herein, H, $C_{1-6}$ alkyl (optionally substituted and/or terminated by one or more substituents selected from —OH, $C_{1-4}$ alkoxy and halo), optionally substituted phenyl or $Het^4$;

$R^7$ represents, at each occurrence when used herein, $C_{1-8}$ alkyl (which group is optionally substituted and/or terminated by one or more substituents selected from —OH, halo, cyano, optionally substituted phenyl, $C_{1-4}$ alkoxy, —SO$_2R^{13a}$, —C(O)$R^{13b}$ and $Het^5$);

$R^{13a}$ and $R^{13b}$ independently represent $C_{1-6}$ alkyl;

$R^8$ represents, at each occurrence when used herein, $C_{1-8}$ alkyl (which group is optionally substituted and/or terminated by one or more substituents selected from —OH, halo, cyano and $C_{1-4}$ alkoxy), —D-(optionally substituted phenyl), —D-$Het^6$, —D—S(O)$_2R^{15a}$, —D—C(O)—$C_{1-6}$ alkyl or —D—C(O)$OR^{15b}$;

$R^{15a}$ and $R^{15b}$ independently represent $C_{1-6}$ alkyl (optionally substituted and/or terminated by one or more substituents selected from halo, cyano and optionally substituted phenyl) or optionally substituted phenyl;

D represents a direct bond or $C_{1-3}$ alkylene;

$R^9$ represents, at each occurrence when used herein, $C_{1-5}$ alkyl (optionally substituted and/or terminated by one or more substituents selected from halo, cyano and optionally substituted phenyl) or optionally substituted phenyl;

$R^2$ represents H, $C_{1-2}$ alkyl, —$OR^{16}$, —N(H)$R^{17}$ or, together with $R^3$, represents =O;

$R^3$ represents H, $C_{1-12}$ alkyl or, together with $R^2$, represents =O;

$R^{16}$ represents H, $C_{1-4}$ alkyl, —E-optionally substituted phenyl, —C(O)$R^{19a}$ or —C(O)N(H)$R^{20a}$;

$R^{17}$ represents H, $C_{1-4}$ alkyl, —E-optionally substituted phenyl, —C(O)$R^{19a}$ or —C(O)$OR^{19b}$;

$R^{19a}$ and $R^{19b}$ independently represent, at each occurrence when used herein, $C_{1-6}$ alkyl, optionally substituted phenyl or $Het^{10}$;

$R^{20a}$ represents H or $C_{1-4}$ alkyl;

E represents, at each occurrence when used herein, a direct bond or $C_{1-2}$ alkylene;

A represents —G—;

B represents —Z—, —Z—N(H)—, —Z—S(O)$_n$—, —Z—O— (in which latter three groups, Z is attached to the carbon atom bearing $R^2$ and $R^3$);

G represents a direct bond or $C_{1-5}$ alkylene;

Z represents a direct bond or $C_{1-3}$ alkylene;

$R^4$ represents phenyl or $Het^{13}$, both of which groups are optionally substituted by one or more substituents selected from cyano, halo, nitro, $C_{1-4}$ alkyl (optionally terminated by —N(H)C(O)$OR^{23a}$), $C_{1-4}$ alkoxy, optionally substituted phenyl, —C(O)N(H)$R^{24e}$, —N(H)C(O)$R^{24h}$, —N(H)C(O)N(H)$R^{24j}$, —N(H)S(O)$_2R^{23b}$, —S(O)$_2R^{23c}$ and —S(O)$_2N(R^{24n})R^{24p}$;

$Het^{13}$ represents a five- to ten-membered heterocyclic group containing one or more heteroatoms selected from oxygen, nitrogen and/or sulfur; $Het^1$ to $Het^{12}$ independently represent, at each occurrence when used herein, five- to ten-membered heterocyclic groups containing one or more heteroatoms selected from oxygen, nitrogen and/or sulfur, which heterocyclic groups are optionally substituted by one or more substituents including =O, —OH, cyano, halo, nitro, $C_{1-4}$ alkyl, $C_{1-4}$ alkoxy, optionally substituted phenyl, —NH$_2$, —C(O)$R^{24c}$, —C(O)$OR^{24d}$, —C(O)N(H)$R^{24e}$, —N(H)C(O)$R^{24h}$ and —S(O)$_nR^{23c}$;

$R^a$ to $R^f$ independently represent H or $C_{1-2}$ alkyl; optional substituents on phenyl groups are one or more groups selected from —OH, cyano, halo, nitro, $C_{1-4}$ alkyl (optionally terminated by —N(H)C(O)$OR^{23a}$), $C_{1-4}$ alkoxy, —NH$_2$, —C(O)$R^{24c}$, —C(O)$OR^{24d}$, —C(O)N(H)$R^{24e}$, —N(H)C(O)$R^{24h}$, —N(H)C(O)N(H)$R^{24j}$, —N(H)S(O)$_2R^{23b}$, —S(O)$_nR^{23c}$ and —S(O)$_2N(R^{24n})R^{24p}$;

$R^{23a}$ to $R^{23c}$, $R^{24c}$, $R^{24d}$, $R^{24e}$, $R^{24h}$, $R^{24j}$, $R^{24n}$ and $R^{24p}$ independently represent, at each occurrence herein, $C_{1-4}$ alkyl;

n represents 0 or 2;

alkyl groups and alkoxy groups may be, unless otherwise specified:

(i) straight- or branched-chain or cyclic or part cyclic/acyclic;

(ii) saturated or unsaturated;

(iii) interrupted by one or more oxygen atoms; and/or (iv) substituted by one or more fluoro or chloro atoms.

More preferred compounds of the invention include those in which:

$R^1$ represents $C_{1-6}$ alkyl (optionally substituted and/or terminated by one or more groups selected from halo, phenyl (optionally substituted by one or more of halo, cyano and $C_{1-2}$ alkoxy), Het$^1$, —C(O)R$^{5a}$, —OR$^{5b}$, —C(O)N(H)—$C_{1-4}$ alkyl and —S(O)$_2$—$C_{1-4}$ alkyl), Het$^2$, —C(O)OR$^7$, —C(O)N(H)R$^8$ or —S(O)$_2$—$C_{1-5}$ alkyl;

Het$^2$ represents a 5-membered heterocyclic group containing between one and four heteroatoms selected from oxygen, nitrogen and/or sulfur, which heterocyclic group is optionally substituted by one or more substituents selected from cyano, halo, nitro, $C_{1-4}$ alkyl and $C_{1-4}$ alkoxy;

$R^{5a}$ and $R^{5b}$ independently represent, at each occurrence when used herein, H, $C_{1-5}$ alkyl (optionally substituted and/or terminated by one or more substituents selected from $C_{1-2}$ alkoxy and halo) or phenyl (optionally substituted by one or more of halo, cyano and $C_{1-2}$ alkoxy);

$R^7$ represents $C_{1-6}$ alkyl (which group is optionally substituted and/or terminated by one or more substituents selected from —OH, halo, cyano, $C_{1-2}$ alkoxy, —SO$_2$—$C_{1-4}$ alkyl, —C(O)—$C_{1-5}$ alkyl and Het$^5$);

Het$^1$ and Het$^5$ independently represent 5- to 7-membered heterocyclic groups, which groups contain between one and four heteroatoms selected from oxygen, nitrogen and/or sulfur, and which heterocyclic groups are optionally substituted by one or more substituents selected from cyano, halo, nitro, $C_{1-4}$ alkyl, $C_{1-4}$ alkoxy and —C(O)—$C_{1-4}$ alkyl;

$R^8$ represents, at each occurrence when used herein, $C_{1-6}$ alkyl (which group is optionally substituted and/or terminated by one or more substituents selected from halo and $C_{1-3}$ alkoxy), phenyl (which group is optionally substituted by one or more of —OH, cyano, halo, nitro, $C_{1-4}$ alkyl, $C_{1-4}$ alkoxy, and —S—($C_{1-4}$ alkyl)), Het$^6$ or —S(O)$_2$ R$^{15a}$;

Het$^6$ represents a 5- to 7-membered heterocyclic group, which group contains between one and four heteroatoms selected from oxygen, nitrogen and/or sulfur, and which heterocyclic group is optionally substituted by one or more substituents selected from cyano, halo, nitro, $C_{1-4}$ alkyl and $C_{1-4}$ alkoxy;

$R^{15a}$ represents $C_{1-4}$ alkyl or phenyl (which group is optionally substituted by one or more of —OH, cyano, halo, nitro, $C_{1-4}$ alkyl and $C_{1-4}$ alkoxy);

$R^2$ represents H, —OR$^a$ or —N(H)R$^{17}$;

$R^3$ represents H or methyl;

$R^{16}$ represents H, $C_{1-2}$ alkyl or phenyl (which group is optionally substituted by one or more of —OH, cyano, halo, nitro, $C_{1-4}$ alkyl and $C_{1-4}$ alkoxy);

$R^{17}$ represents H, $C_{1-2}$ alkyl, —(CH$_2$)$_{0-1}$-phenyl (which group is optionally substituted by one or more of —OH, cyano, halo, nitro, $C_{1-4}$ alkyl and $C_{1-4}$ alkoxy), or —C(O)O—($C_{1-4}$ alkyl);

A represents $C_{1-4}$ alkylene;

B represents —Z—, —Z—N(H)—, —Z—S(O)$_2$—, —Z—O— (in which latter three groups, Z is attached to the carbon atom bearing $R^2$ and $R^3$);

Z represents a direct bond or $C_{1-2}$ alkylene;

$R^4$ represents phenyl, which group is optionally substituted by one or more substituents selected from cyano, halo, nitro, $C_{1-4}$ alkyl and $C_{1-4}$ alkoxy;

$R^a$ to $R^f$ all represent H;

alkyl groups and alkoxy groups may be, unless otherwise specified:

(i) straight- or branched-chain or cyclic or part cyclic/acyclic;

(ii) saturated or unsaturated;

(iii) interrupted by an oxygen atom; and/or (iv) substituted by one or more fluoro atoms.

Particularly preferred compounds of the invention include those in which:

$R^1$ represents $C_{1-5}$ alkyl (which alkyl group is optionally part cyclic/acyclic, interrupted by oxygen and/or substituted or terminated by one of phenyl (optionally substituted by one or more of fluoro and methoxy), Het$^1$, —C(O)R$^{5a}$, —OR$^{5b}$, —C(O)N(H)—$C_{1-3}$ alkyl and —S(O)$_2$—$C_{1-3}$ alkyl), Het$^2$, —C(O)OR$^7$, —C(O)N(H)R$^8$ or —S(O)$_2$—$C_{1-5}$ alkyl;

Het$^2$ represents a 5-membered heterocyclic group containing one or two heteroatoms selected from oxygen, nitrogen and/or sulfur, which heterocyclic group is optionally substituted by one or more substituents selected from halo, $C_{1-2}$ alkyl and $C_{1-2}$ alkoxy;

$R^{5a}$ and $R^{5b}$ independently represent, at each occurrence when used herein, H, $C_{1-4}$ alkyl (optionally substituted or terminated by methoxy) or phenyl (optionally substituted by one or more of fluoro and methoxy);

$R^7$ represents $C_{1-5}$ alkyl (which group is optionally unsaturated and/or substituted or terminated by one of —OH, cyano, methoxy, —SO$_2$—$C_{1-2}$ alkyl, —C(O)—$C_{1-4}$ alkyl and Het$^5$);

Het$^1$ and Het$^5$ independently represent 5- to 7-membered heterocyclic groups, which groups contain between one and three heteroatoms selected from oxygen, nitrogen and/or sulfur, and which heterocyclic groups are optionally substituted by one or more substituents selected from $C_{1-2}$ alkyl, $C_{1-2}$ alkoxy and —C(O)—$C_{1-2}$ alkyl;

$R^8$ represents, at each occurrence when used herein, $C_{1-5}$ alkyl (which group is optionally unsaturated, part cyclic/acyclic, interrupted by oxygen and/or substituted or terminated by methoxy), phenyl (which group is optionally substituted by one or more of fluoro, $C_{1-2}$ alkyl, $C_{1-2}$ alkoxy, and —S—($C_{1-2}$ alkyl) (the alkyl part of which latter group is optionally substituted by one or more fluoro atoms)), Het$^6$ or —S(O)$_2$R$^{15}$a;

Het$^6$ represents a 5- to 7-membered heterocyclic group, which group contains between one and three heteroatoms selected from oxygen, nitrogen and/or sulfur, and which heterocyclic group is optionally substituted by one or more substituents selected from $C_{1-2}$ alkyl and $C_{1-12}$ alkoxy;

$R^{15a}$ represents phenyl (which group is optionally substituted by one or more of $C_{1-2}$ alkyl and $C_{1-2}$ alkoxy);

$R^2$ represents H, —OR$^{16}$ or —NH$_2$;

$R^3$ represents H;

$R^{16}$ represents H or phenyl (which group is optionally substituted by one or more cyano or $C_{1-2}$ alkoxy groups);

A represents $C_{1-3}$ alkylene;

B represents —Z—, —Z—N(H)—, —Z—S(O)$_2$—, —Z—O— (in which latter three groups, Z is attached to the carbon atom bearing $R^2$ and $R^3$);

Z represents a direct bond or CH$_2$;

$R^4$ represents phenyl, which group is substituted by at least one cyano group and which group is optionally substituted by one or two further substituents selected from cyano, halo and nitro alkyl groups and alkoxy groups may be, unless otherwise specified, straight- or branched-chain.

Especially preferred compounds of the invention include those in which:

$R^{16}$ represents H or phenyl (which group is substituted by one to three methoxy groups);

A represents C$_{1-3}$ alkylene;

B represents —Z—, —Z—N(H)—, —Z—S(O)$_2$—, —Z—O— (in which latter three groups, Z is attached to the carbon atom bearing R$^2$ and R$^3$);

Z represents a direct bond or, when R$^2$ represents OH or NH$_2$, Z represents CH$_2$;

R$^4$ represents phenyl substituted in the 4-position (relative to the group B) by cyano, and optionally substituted in the 2-position (relative to the group B) by a further cyano group.

According to a further aspect of the invention there is provided compounds of formula I which are compounds of formula Ia,

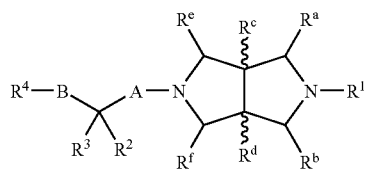

Ia wherein the wavy lines represent optional relative cis- or trans-stereochemistry;

R$^1$ represents C$_{1-12}$ alkyl (optionally substituted and/or terminated by one or more groups selected from halo, cyano, nitro, aryl, Het$^{1a}$, —C(O)R$^{5a1}$, —OR$^{5b}$, —N(R$^6$)R$^{5c}$, —C(O)XR$^7$, —C(O)N(R$^8$)R$^{5d}$ and —S(O)$_2$R$^9$), Het$^2$, —C(O)R$^{5a2}$, —C(O)XR$^7$, —C(O)N(R$^8$)R$^{5d}$, —S(O)R$^9$ or —CH$_2$C(O)-(unsubstituted C$_{1-6}$ alkyl);

R$^{5a1}$ represents aryl (which latter group is optionally substituted by one or more substituents selected from —OH, cyano, halo, nitro, C$_{1-6}$ alkyl (optionally terminated by —N(H)C(O)OR$^{23a}$), C$_{1-6}$ alkoxy, Het$^1$, aryl (which aryl group may not be substituted with any further aryl groups), —N(C$_{1-6}$ alkyl)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, N(R$^{24m}$)S(O)$_2$R$^{23b}$, —S(O)$_n$R$^{23c}$, —OS(O)$_2$R$^{23d}$ and —S(O)$_2$N(R$^{24n}$)R$^{24}$p) or Het$^{4a}$;

R$^{5a2}$ represents H, C$_{1-6}$ alkyl (optionally substituted and/or terminated by one or more substituents selected from —OH, C$_{1-6}$ alkoxy, halo, cyano, nitro, aryl, Het$^{3a}$ and —NHC(O)R$^{10}$), aryl or Het$^{4a}$;

R$^{5b}$ to R$^{5d}$ independently represent, at each occurrence when used herein, H, C$_{1-6}$ alkyl (optionally substituted and/or terminated by one or more substituents selected from —OH, C$_{1-6}$ alkoxy, halo, cyano, nitro, aryl, Het$^3$ and —NHC(O)R$^{10}$), aryl or Het$^4$, or R$^{5d}$, together with R$^8$, represents C$_{3-6}$ alkylene (which alkylene group is optionally interrupted by an O atom and/or is optionally substituted by one or more C$_{1-3}$ alkyl groups);

R$^{10}$ represents H, C$_{1-4}$ alkyl (optionally substituted and/or terminated by one or more substituents selected from halo, cyano, aryl and —NHC(O)R$^{11}$) or aryl;

R$^{11}$ represents H, C$_{1-4}$ alkyl or aryl;

R$^6$ represents H, C$_{1-6}$ alkyl (optionally substituted and/or terminated by one or more substituents selected from —OH, halo, cyano, nitro and aryl), aryl, —C(O)R$^{12a}$, —C(O)OR$^{12b}$ or —C(O)N(H)R$^{12c}$;

R$^{12a}$, R$^{12b}$ and R$^{12c}$ represent C$_{1-6}$ alkyl (optionally substituted and or terminated by one or more substituents selected from —OH, halo, cyano, nitro and aryl) or aryl, or R$^{12a}$ and R$^{12c}$ represent H;

X represents O or S;

R$^7$ represents, at each occurrence when used herein, aryl or C$_{1-12}$ alkyl (which alkyl group is optionally substituted and/or terminated by one or more substituents selected from —OH, halo, cyano, nitro, aryl, C$_{1-6}$ alkoxy, —SO$_2$R$^{13a}$, —C(O)R$_{13b}$ and Het$^5$);

R$^{13a}$ and R$^{13b}$ independently represent C$_{1-6}$ alkyl or aryl;

R$^8$ represents, at each occurrence when used herein, H, C$_{1-12}$ alkyl, C$_{1-6}$ alkoxy (which latter two groups are optionally substituted and/or terminated by one or more substituents selected from —OH, halo, cyano, nitro, C$_{1-4}$ alkyl and C$_{1-4}$ alkoxy), —D-aryl, —D-aryloxy, —D-Het$^6$, —D—N(H)C(O)R$^{14a}$, —D—S(O)$_2$R$^{15a}$, —D—C(O)R$^{14b}$, —D—C(O)OR$^{15b}$, —D—C(O)N(R$^{14c}$)R$^{14d}$, or R$^8$, together with R$^{5d}$, represents C$_{3-6}$ alkylene (which alkylene group is optionally interrupted by an O atom and/or is optionally substituted by one or more C$_{1-3}$ alkyl groups);

R$^{14a}$ to R$^{14d}$ independently represent H, C$_{1-6}$ alkyl (optionally substituted and/or terminated by one or more substituents selected from —OH, halo, cyano, nitro and aryl), aryl, or R$^{14c}$ and R$^{14d}$ together represent C$_{3-6}$ alkylene;

R$^{15a}$ and R$^{15b}$ independently represent C$_{1-6}$ alkyl (optionally substituted and/or terminated by one or more substituents selected from —OH, halo, cyano, nitro and aryl) or aryl;

D represents a direct bond or C$_{1-6}$ alkylene;

R$^9$ represents, at each occurrence when used herein, C$_{1-6}$ alkyl (optionally substituted and/or terminated by one or more substituents selected from —OH, halo, cyano, nitro and aryl), aryl or Het$^7$;

R$^2$ represents H, halo, C$_{1-6}$ alkyl, —E—OR$^{16}$ or —E—N(R$^{17}$)R$^{18}$;

R$^3$ represents H or C$_{1-6}$ alkyl;

R$^{16}$ represents H, C$_{1-6}$ alkyl, —E-aryl, —E-Het$^1$, —C(O)R$^{19a}$, —C(O)OR$^{19b}$ or —C(O)N(R$^{20a}$)R$^{20b}$;

R$^{17}$ represents H, C$_{1-6}$ alkyl, —E-aryl, —E-Het$^8$, —C(O)R$^{19a}$, C(O)OR$^{19b}$, —S(O)$_2$R$^{19c}$, [C(O)]$_p$N(R$^{20a}$)R$^{20b}$ or —C(NH)NH$_2$;

R$^{18}$ represents H, C$_{1-6}$ alkyl, —E-aryl or —C(O)R$^{19d}$;

R$^{19a}$ to R$^{19d}$ independently represent, at each occurrence when used herein, C$_{1-6}$ alkyl (optionally substituted and/or terminated by one or more substituents selected from halo, aryl and Het$^9$), aryl, Het$^{10}$, or R$^{19a}$ and R$^{19d}$ independently represent H;

R$^{20a}$ and R$^{20b}$ independently represent, at each occurrence when used herein, H or C$_{1-6}$ alkyl (optionally substituted and/or terminated by one or more substituents selected from halo, aryl and Het$^{11}$), aryl, Het$^{12}$, or together represent C$_{3-6}$ alkylene, optionally interrupted by an O atom;

E represents, at each occurrence when used herein, a direct bond or C$_{1-4}$ alkylene;

p represents 1 or 2;

A represents —G—, —J—N(R$^{21}$)— or —J—O— (in which latter two groups, N(R$^{21}$)— or O— is attached to the carbon atom bearing R$^2$ and R$^3$);

B represents —Z—, —Z—N(R$^{22}$)—, —N(R$^{22}$)—Z—, —Z—S(O)$_n$—, —Z—O— (in which latter two groups, Z is attached to the carbon atom bearing R$^2$ and R$^3$);

G represents C$_{1-6}$ alkylene;

J represents C$_{2-6}$ alkylene;

Z represents a direct bond or C$_{1-4}$ alkylene;

R$^{21}$ and R$^{22}$ independently represent H or C$_{1-6}$ alkyl;

R$^4$ represents aryl or Het$^{13}$, both of which groups are optionally substituted by one or more substituents selected from —OH, cyano, halo, nitro, C$_{1-6}$ alkyl (optionally terminated by —N(H)C(O)OR$^{23a}$), C$_{1-6}$ alkoxy, Het$^1$, aryl, —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)$_2$R$^{23d}$, —S(O)$_2$N(R$^{24n}$)R$^{24p}$ and (in the case of Het$^{13}$ only) oxo;

Het$^{13}$ represents a four- to eight-membered heterocyclic group containing one or more heteroatoms selected from oxygen, nitrogen and/or sulfur;

Het$^1$ to Het$^{12}$ independently represent, at each occurrence when used herein, four- to twelve-membered heterocyclic groups containing one or more heteroatoms selected from oxygen, nitrogen and/or sulfur, which heterocyclic groups are optionally substituted by one or more substituents including =O, —OH, cyano, halo, nitro, $C_{1-6}$ alkyl (optionally terminated by —N(H)C(O)OR$^{23a}$), $C_{1-6}$ alkoxy, Het$^1$, aryl, —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)$_2$R$^{23d}$ and —S(O)$_2$N(R$_{24n}$)R$^{24p}$;

Het$^{1a}$, Het$^{3a}$ and Het$^{4a}$ independently represent, at each occurrence when used herein, four- to eight-membered heterocyclic groups containing one or more heteroatoms selected from oxygen, nitrogen and/or sulfur, which heterocyclic groups are optionally substituted by one or more substituents including =O, —OH, cyano, halo, nitro, $C_{1-6}$ alkyl (optionally terminated by —N(H)C(O)OR$^{23a}$), $C_{1-6}$ alkoxy, Het$^1$, aryl, —N($^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)$_2$R$^{23d}$ and —S(O)$_2$N(R$^{24n}$)R$^{24p}$;

R$^{23a}$ to R$_{23d}$ independently represent, at each occurrence when used herein, $C_{1-6}$ alkyl;

R$^{24a}$ to R$^{24p}$ independently represent, at each occurrence when used herein, H or $C_{1-6}$ alkyl;

n represents, at each occurrence, 0, 1 or 2; and

R$^a$ to R$^f$ independently represent H or $C_{1-4}$ alkyl;

wherein each aryl and aryloxy group, unless otherwise specified, is optionally substituted;

or a pharmaceutically acceptable derivative thereof;

provided that:
(a) when R$^3$ represents H or $C_{1-4}$ alkyl; and
   A represents —J—N(R$^{21}$)— or —J—O—;
   then B does not represent —N(R$^{22}$)—, —S(O)$_n$—, —O— or —N(R$^{22}$)—Z— (in which latter group —N(R$^{22}$) is attached to the carbon atom bearing R$^2$ and R$^3$); and
(b) when R$^2$ represents —E—OR$^{16}$ or —E—N(R$^{17}$)R$^{18}$ in which E represents a direct bond, then:
   (i) A does not represent —J—N(R$^{21}$)— or —J—O—; and
   (ii) B does not represent —N(R$^{22}$)—, —S(O)$_n$—, —O— or —N(R$^{22}$)—Z— (in which latter group —N(R$^{22}$) is attached to the carbon atom bearing R$^2$ and R$^3$);

which compounds are also referred to hereinafter as "the compounds of the invention".

Preferred compounds of formula Ia include (where appropriate) the preferred compounds of formula I, as defined above.

Preferred compounds of formula Ia also include those in which:

R$^1$ represents $C_{1-2}$ alkyl (substituted or terminated by a Het$^{1a}$ or —C(O)R$^{5a1}$ group) —C(O)R$^{5a2}$, or —CH$_2$C(O)-(unsubstituted $C_{1-4}$ alkyl);

R$^{5a1}$ represents phenyl (which latter group is substituted by one or two substituents selected from halo and $C_{1-2}$ alkoxy)

R$^{5a2}$ represents H, $C_{1-6}$ alkyl (optionally substituted and/or terminated by one or more substituents selected from $C_{1-3}$ alkoxy and halo) or Het$^{4a}$;

G represents $C_{1-4}$ alkylene;

Het$^{13}$ represents a five- or six-membered heterocyclic group containing one or more heteroatoms selected from oxygen, nitrogen and/or sulfur, Het$^{1a}$, Het$^{3a}$ and Het$^{4a}$ independently represent, at each occurrence when used herein, five- or six-membered heterocyclic groups containing one or more heteroatoms selected from oxygen, nitrogen and/or sulfur, which heterocyclic groups are optionally substituted by one to three substituents selected from =O, -cyano, halo, nitro, $C_{1-4}$ alkyl, $C_{1-4}$ alkoxy, aryl, —N(H)R$^{24a}$, —C(O)R$^{24c}$, —C(O)OR$^{24d}$, —C(O)N(H)R$^{24e}$, N(R$^{24g}$)C(O)R$^{24h}$ and —S(O)$_n$R$^{23c}$.

Preferred compounds of the invention include the compounds of the Examples disclosed hereinafter.

Preparation

According to the invention there is also provided a process for the preparation of compounds of formula I which comprises:

(a) reaction of a compound of formula II,

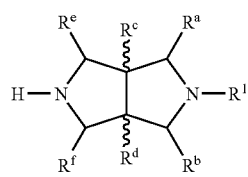

wherein R$^1$ and R$^a$ to R$^f$ are as hereinbefore defined, with a compound of formula III,

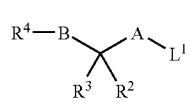

wherein L$^1$ represents a leaving group (e.g. mesylate, tosylate or halo) and R$^2$, R$^3$, R$^4$, A and B are as hereinbefore defined, for example at between –10° C. and reflux temperature in the presence of a suitable base (e.g. triethylamine or K$_2$CO$_3$) and an appropriate organic solvent (e.g. dichloromethane, acetonitrile or DMSO);

(b) for compounds of formula I in which A represents C$_2$ alkylene and R$^2$ and R$^3$ together represent =O, reaction of a corresponding compound of formula II, as hereinbefore defined, with a compound of formula IV,

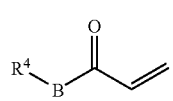

wherein R$^4$ and B are as hereinbefore defined, for example at room temperature in the presence of a suitable organic solvent (e.g. ethanol);

(c) for compounds of formula I in which A represents CH$_2$ and R$^2$ represents —OH or —N(H)R$^{17}$, reaction of a corresponding compound of formula II, as hereinbefore defined, with a compound of formula V,

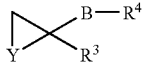

V wherein Y represents O or $N(R^{17})$ and $R^3$, $R^4$, $R^{17}$ and B are as hereinbefore defined, for example at elevated temperature (e.g. 60° C. to reflux) in the presence of a suitable solvent (e.g. a lower alkyl alcohol (e.g. IPA), acetonitrile, or a mixture of a lower alkyl alcohol and water);

(d) for compounds of formula I in which A represents $C_{1-6}$ alkylene, B represents $C_{1-4}$ alkylene and $R^2$ and $R^3$ both represent H, reduction of a corresponding compound of formula I in which $R^2$ and $R^3$ together represent =O, in the presence of a suitable reducing agent and under appropriate reaction conditions, for example by activating the relevant C=O group using an appropriate agent (such as tosylhydrazine) in the presence of a suitable reducing agent (e.g. sodium borohydride or sodium cyanoborohydride) and an appropriate organic solvent (e.g. a lower (e.g. $C_{1-6}$) alkyl alcohol);

(e) for compounds of formula I in which $R^2$ and $R^3$ both represent H and (1) A represents a single bond or —J—N($R^{21}$) and B represents $C_{1-4}$ alkylene, or (2) A represents $C_{1-6}$ alkylene and B represents $N(R^{22})$ or —N($R^{22}$)—Z— (in which latter group —N($R^{22}$) is attached to the carbon atom bearing $R^2$ and $R^3$), reduction of a corresponding compound of formula I in which $R^2$ and $R^3$ together represent =O, in the presence of a suitable reducing agent (e.g. LiAlH$_4$) and an appropriate solvent (e.g. THF);

(f) for compounds of formula I in which A represents $C_{1-6}$ alkylene, B represents a direct bond, $C_{1-4}$ alkylene, —Z—N($R^{22}$)—, —Z—S(O)$_n$— or —Z—O— (in which latter three groups Z represents $C_{1-4}$ alkylene), $R^2$ represents OH and $R^3$ represents H, reduction of a corresponding compound of formula I in which $R^2$ and $R^3$ together represent =O, in the presence of a suitable reducing agent (e.g. NaBH$_4$) and an appropriate organic solvent (e.g. THF);

(g) for compounds of formula I in which B represents —Z—O—, reaction of a compound of formula VI,

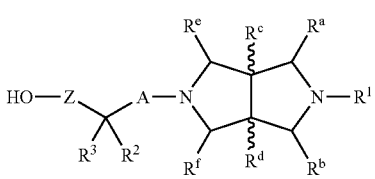

VI wherein $R^1$, $R^2$, $R^3$, $R^a$ to $R^f$, A and Z are as hereinbefore defined, with a compound of formula VII,

 VII in which $R^4$ is as hereinbefore defined, for example under Mitsunobu-type conditions e.g. at between ambient (e.g. 25° C.) and reflux temperature in the presence of a tertiary phosphine (e.g. tributylphosphine or triphenylphosphine), an azodicarboxylate derivative (e.g. diethylazodicarboxylate or 1,1′-(azodicarbonyl)dipiperidine) and an appropriate organic solvent (e.g. dichloromethane or toluene);

(h) for compounds of formula I in which B represents —Z—O—, reaction of a compound of formula VI, as hereinbefore defined, with a compound of formula VIII,

 VIII wherein $L^2$ represents a leaving group such as halo, alkanesulfonate, perfluoroalkanesulfonate or arenesulfonate, and $R^4$ is as hereinbefore defined, for example under conditions known to those skilled in the art (e.g. when $R^4$ represents 2- or 4pyridyl, reaction at between 10° C. and reflux temperature in the presence of a suitable base (such as sodium hydride) and an appropriate solvent (such as N,N-dimethylformamide));

(i) for compounds of formula I in which A represents $C_{1-6}$ alkylene and B represents —N($R^{22}$)—Z— (wherein the group —N($R^{22}$)— is attached to the carbon atom bearing $R^2$ and $R^2$), reaction of a compound of formula IX,

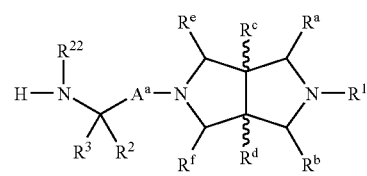

IX wherein $A^a$ represents $C_{1-6}$ alkylene and $R^1$, $R^2$, $R^3$, $R^{22}$ and $R^a$ to $R^f$ are as hereinbefore defined with a compound of formula X,

 X wherein $L^2$, $R^4$ and Z are as hereinbefore defined, for example at 40° C. in the presence of a suitable organic solvent (e.g. acetonitrile);

(j) for compounds of formula I in which $R^2$ represents —E—NH$_2$, reduction of a corresponding compound of formula XI,

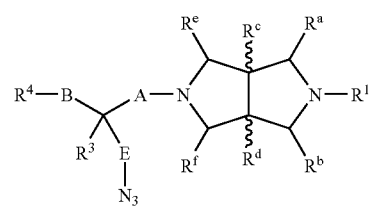

XI wherein $R^1$, $R^3$, $R^4$, $R^a$ to $R^f$, A, B and E are as hereinbefore defined, for example by hydrogenation at a suitable pressure in the presence of a suitable catalyst (e.g. palladium on carbon) and an appropriate solvent (e.g. a water-ethanol mixture);

(k) for compounds of formula I in which $R^2$ represents —E—N($R^{18}$)C(O)N(H)$R^{20a}$, reaction of a corresponding compound of formula I in which $R^2$ represents —E—N($R^{18}$)H with a compound of formula XII,

 XII wherein $R^{20a}$ is as hereinbefore defined, for example at ambient temperature. (e.g. 25° C.) in the presence of a suitable solvent (e.g. benzene);

(l) for compounds of formula I in which $R^2$ represents —E—N(H)[C(O)]$_2$NH$_2$, reaction of a corresponding compound of formula I in which $R^2$ represents —E—NH$_2$ with oxalic acid diamide, for example at between −10 and 25° C. in the presence of a suitable coupling agent (e.g. 1-(3-dimethylaminopropyl)-3-ethylcarbodiimide), an appropriate activating agent (e.g. 1-hydroxybenzotriazole), a suitable base (e.g. triethylamine) and a reaction-inert organic solvent (e.g. DMF);

(m) for compounds of formula I in which $R^2$ represents —E—N($R^{17}$)$R^{18}$, wherein $R^{17}$ and $R^{18}$ are as hereinbefore defined, provided that $R^{17}$ does not represent H, reaction of a corresponding compound of formula I, in which $R^2$ represents —D—N(H)$R^{18}$ with a compound of formula XIII,

$$R^{17a}—L^3 \qquad \text{XIII}$$

wherein $R^{17a}$ represents $R^{17}$ as hereinbefore defined except that it does not represent H, and $L^3$ represents a leaving group such as halo (e.g. chloro or bromo), p-nitrophenolate, $C_{1-4}$ alkoxide, $C_{1-4}$ alkylthiolate, —OC(O)$R^{19a}$, —OC(O)O$R^{19b}$, or —OS(O)$_2R^{19c}$, wherein $R^{19a}$ to $R^{19c}$ are as hereinbefore defined, for example under conditions that are well known to those skilled in the art;

(n) for compounds of formula I in which $R^2$ represents —E—OR$^{16}$ in which $R^{16}$ represents $C_{1-6}$ alkyl, —E-aryl or —E-Het$^8$, reaction of a corresponding compound of formula I in which $R^2$ represents —E—OH with a compound of formula XIV, $$R^{16a}OH \qquad \text{XIV}$$

wherein $R^{16a}$ represents $C_{1-6}$ alkyl, —E-aryl or —E-Het$^8$, wherein Het$^8$ is as hereinbefore defined, for example at between ambient (e.g. 25° C.) and reflux temperature, under Mitsunobu-type conditions (i.e. in the presence of e.g. triphenylphosphine, an azodicarboxylate derivative (e.g. 1,1'-(azodicarbonyl)dipiperidine) and a suitable organic solvent (e.g. dichloromethane));

(o) for compounds of formula I in which $R^2$ represents —E—OR$^{16}$ (in which $R^{16}$ represents $C_{1-6}$ alkyl, —E-aryl or —E-Het$^8$), reaction of a corresponding compound of formula XV,

XV

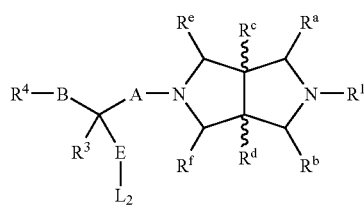

wherein $L^2$, $R^1$, $R^3$, $R^4$, $R^a$ to $R^f$, A, B and E are as hereinbefore defined with a compound of formula XIV as hereinbefore defined, for example at between ambient (e.g. 25° C.) and reflux temperature, under Williamson-type conditions (i.e. in the presence of an appropriate base (e.g. KOH or NaH) and a suitable organic solvent (e.g. dimethylsulfoxide or DMF));

(p) for compounds of formula I in which $R^2$ represents —E—OR$^{16}$, wherein $R^{16}$ is as hereinbefore defined, provided that it does not represent H, reaction of a corresponding compound of formula I in which $R^2$ represents —E—OH with a compound of formula XVI,

$$R^{16b}—L^4 \qquad \text{XVI}$$

wherein $R^{16b}$ represents $R^{16}$ as hereinbefore defined, except that it does not represent H, and $L^4$ represents a leaving group such as OH, halo, alkanesulfonate, arenesulfonate or —OC(O)$R^{19a}$, wherein $R^{19a}$ is as hereinbefore defined, for example at between room and reflux temperature, optionally in the presence of a reaction-inert organic solvent (e.g. THF or CH$_2$Cl$_2$), a suitable base (e.g. triethylamine or K$_2$CO$_3$) and/or an appropriate coupling agent (e.g. 1,3-dicyclohexylcarbodiimide or 1-(3-dimethylaminopropyl)-3-ethylcarbodiimide, optionally combined with a suitable catalyst such as 4-dimethylaminopyridine) (for example, when $R^{16b}$ represents —C(O)$R^{19a}$ and $L^4$ represents OH, this reaction may be performed at ambient temperature (e.g. 25° C.) in the presence of a coupling agent such as 1-(3-dimethylaminopropyl)-3-ethylcarbodiimide, an appropriate catalyst such as 4-(dimethylamino)pyridine and a solvent such as THF);

(q) for compounds of formula I in which $R^2$ represents halo, substitution of a corresponding compound of formula I in which $R^2$ represents —OH, using an appropriate halogenating agent (e.g., for compounds in which $R^2$ represents fluoro, reaction with (diethylamino)sulfur trifluoride);

(r) reaction of a corresponding compound of formula XVII,

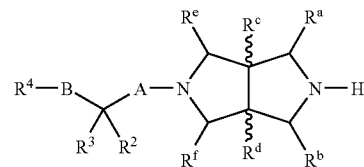

XVII wherein $R^2$, $R^3$, $R^4$, $R^a$ to $R^f$, A and B are as hereinbefore defined, with a compound of formula XVIII,

$$R^1—L^5 \qquad \text{XVIII}$$

wherein $L^5$ represents a leaving group such as halo, OH, alkanesulfonate, perfluoroalkanesulfonate, arenesulfonate, imidazole, $R^{25}$O— (wherein $R^{25}$ represents, for example, $C_{1-10}$ alkyl or aryl, which groups are optionally substituted by one or more halo or nitro groups) —OC(O)$R^{5a}$, —OC(O)OR$^7$ or —OS(O)$_2R^9$, and $R^1$, $R^{5a}$, $R^7$ and $R^9$ are as hereinbefore defined, for example at between −10° C. and reflux temperature, optionally in the presence of a suitable solvent (e.g. CHCl$_3$, CH$_3$CN, 2-propanol, diethyl ether, CH$_2$C$_2$, DMSO, DMF, THF; toluene, or mixtures thereof) and/or an appropriate base (e.g. K$_2$CO$_3$, pyridine or triethylamine);

(s) for compounds of formula I in which $R^1$ represents —C(O)XR$^7$ or —C(O)N($R^8$)$R^{5d}$, reaction of a compound of formula XIX,

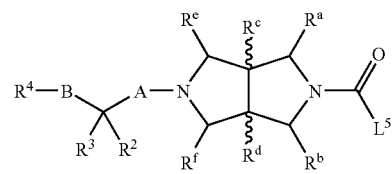

XIX wherein $R^2$, $R^3$, $R^4$, $R^a$ to $R^f$, A, B and $L^5$ are as hereinbefore defined, with a compound of formula XX,

   XX wherein $R^{26}$ represents —$XR^7$ or —$N(R^8)R^{5d}$ and $R^{5d}$, $R^7$, $R^8$ and X are as hereinbefore defined, for example under conditions described hereinbefore (process step (r));

(t) for compounds of formula I in which $R^1$ represents —C(O)N(H)$R^8$, reaction of a corresponding compound of formula XVII, as hereinbefore defined, with a compound of formula XXI,

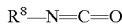   XXI wherein $R^8$ is as hereinbefore defined, for example at between 0° C. and reflux temperature in the presence of an appropriate organic solvent (e.g. dichloromethane), or via solid phase synthesis under conditions known to those skilled in the art;

(u) for compounds of formula I in which $R^1$ represent $C_{1-12}$ alkyl, which alkyl group is substituted at the C-2 carbon (relative to the bispidine nitrogen) with OH or —N(H)$R^6$, and is otherwise optionally substituted with one or more further substituents as specified hereinbefore for $R^1$, reaction of a corresponding compound of formula XVII, as hereinbefore defined, with a compound of formula XXII,

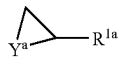   XXII wherein $Y^a$ represents O or N($R^6$), $R^{1a}$ represents $C_{1-10}$ alkyl, optionally substituted with one or more substituents as specified hereinbefore for $R^1$ and $R^6$ is as hereinbefore defined, for example as described hereinbefore for preparation of compounds of formula I (process step (c));

(v) for compounds of formula I in which $R^1$ represents —C(O)$OR^7$ and $R^a$ and/or $R^b$ represent $C_{1-4}$ alkyl, reaction of a corresponding compound of formula I in which $R^1$ represents —C(O)$OR^7$ and $R^a$ and $R^b$ represent H with one or more equivalents of a compound of formula XXIII,

   XXIII wherein $R^{27}$ represents $C_{1-4}$ alkyl and $L^2$ is as hereinbefore defined, in the presence of an appropriate strong base (i.e. a base capable of deprotonating the 3,7-diazabicyclo[3.3.0]octane ring at the position α-to the nitrogen bearing the —C(O)$OR^7$ group (e.g. butyllithium)), for example at between −80° C. and room temperature in the presence of a suitable solvent (e.g. N,N,N',N'-tetramethylethylenediamine, THF or mixtures thereof);

(w) for compounds of formula I which are 3,7-diazabicyclo [3.3.0]octane-nitrogen N-oxide derivatives, oxidation of the corresponding 3,7-diazabicyclo[3.3.0]octane nitrogen of a corresponding compound of formula I, in the presence of a suitable oxidising agent (e.g. mCPBA), for example at 0° C. in the presence of a suitable organic solvent (e.g. DCM);

(x) for compounds of formula I which are $C_{1-4}$ alkyl quaternary ammonium salt derivatives, in which the alkyl group is attached to a 3,7-diazabicyclo- [3.3.0]octane nitrogen, reaction, at the 3,7-diazabicyclo[3.3.0]octane nitrogen, of a corresponding compound of formula I with a compound of formula XXIII, as hereinbefore defined, for example at room temperature in the presence of an appropriate organic solvent (e.g. DMF), followed by purification (using e.g. HPLC) in the presence of a suitable counter-ion provider (e.g. $NH_4OAc$);

(y) conversion of one substituent on $R^4$ to another using techniques well known to those skilled in the art; or (z) conversion of one $R^1$ group to another using techniques well known to those skilled in the art.

Compounds of formula II may be prepared by reaction of a corresponding compound of formula XXIV,

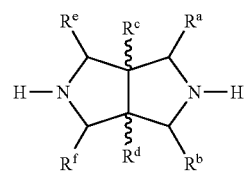   XXIV wherein $R^a$ to $R^f$ are as hereinbefore defined, with a compound of formula XVIII as hereinbefore defined, for example as described hereinbefore for synthesis of compounds of formula I (process step (r)).

Compounds of formula III may be prepared by standard techniques. For example, compounds of formula III in which:

(1) B represents —Z—O— may be prepared by coupling a compound of formula VII, as hereinbefore defined, to a compound of formula XXV,

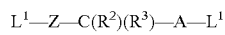   XXV wherein $R^2$, $R^3$, A, Z and $L^1$ are as hereinbefore defined, and the two $L^1$ groups may be the same or different; or (2) B represents —N($R^{22}$)—Z— (wherein N($R^{22}$) is attached to the carbon atom bearing $R^2$ and $R^3$) and $R^2$ and $R^3$ together represent =O may be prepared by coupling a compound of formula XXVI

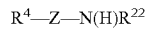   XXVI wherein $R^4$, $R^{22}$ and Z are as hereinbefore defined, to a compound of formula XXVII,

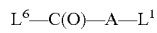   XXVII wherein $L^6$ represents a suitable leaving group (e.g. —OH or halo) and A and $L^1$ are as hereinbefore defined;

in both cases, under conditions which are well known to those skilled in the art.

Compounds of formula III in which A represents $C_2$ alkylene and $R^2$ represents —$OR^{16}$, in which $R^{16}$ represents $C_{1-6}$ alkyl, —E-aryl or —E-$Het^8$ may alternatively be prepared by reaction of a compound of formula XIV, as hereinbefore defined, with a compound of formula XXVIII,

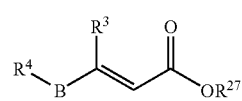   XXVIII wherein $R^3$, $R^4$, $R^{27}$ and B are as hereinbefore defined, for example at between ambient temperature (e.g. 25° C.) and reflux temperature in the presence of a suitable base (e.g. potassium carbonate) and an appropriate organic solvent (e.g. acetonitrile), followed by conversion of the ester functionality to a —CH$_2$—L$^1$ group (in which L$^1$ is as hereinbefore defined), under conditions that are well known to those skilled in the art.

Compounds of formula III in which A represents C$_{2-6}$ alkylene may be prepared by reduction of a corresponding compound of formula XXIX,

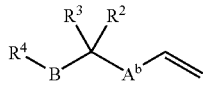

XXIX wherein A$^b$ represents a direct bond or C$_{1-4}$ alkylene, and R$^2$, R$^3$, R$^4$ and B are as hereinbefore defined, with a suitable borane or borane-Lewis base complex (e.g. borane-dimethyl sulfide) in the presence of an appropriate solvent (e.g. diethyl ether, THF, or a mixture thereof), followed by oxidation of the resulting borane adduct with a suitable oxidising agent (e.g. sodium perborate) and then conversion of the resulting OH group to an L$^1$ group under conditions known to those skilled in the art.

Compounds of formula III in which A represents C$_{1-6}$ alkylene and B represents —Z—N(R$^{22}$)— (in which latter case Z is attached to the carbon atom bearing R$^2$ and R$^3$) may be prepared by coupling a compound of formula VIII, as hereinbefore defined, with a compound of formula XXX,

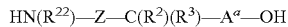
HN(R$^{22}$)—Z—C(R$^2$)(R$^3$)—A$^a$—OH    XXX wherein A$^a$, Z, R$^2$, R$^3$ and R$^{22}$ are as hereinbefore defined, for example at between room and reflux temperature, optionally in the presence of a suitable solvent and/or an appropriate base, followed by conversion of the OH group to an L$^1$ group under conditions known to those skilled in the art.

Compounds of formula III in which B represents —Z—S(O)— or —Z—S(O)$_2$— may be prepared by oxidation of corresponding compounds of formula III in which B represents —Z—S—, wherein Z is as hereinbefore defined, in the presence of an appropriate amount of a suitable oxidising agent (e.g. mCPBA) and an appropriate organic solvent.

Compounds of formula V may be prepared in accordance with techniques that are known to those skilled in the art. For example, compounds of formula V in which:

(1) B represents —CH$_2$O— and Y represents O may be prepared by reaction of a compound of formula VII, as hereinbefore defined, with a compound of formula XXXI

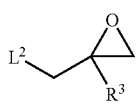

XXXI wherein R$^3$ and L$^2$ are as hereinbefore defined, for example at elevated temperature (e.g. between 60° C. and reflux temperature) in the presence of a suitable base (e.g. potassium carbonate or NaOH) and an appropriate organic solvent (e.g. acetonitrile or toluene/water), or as otherwise described in the prior art;

(2) R$^3$ represents H, B represents a direct bond, C$_{1-4}$ alkylene, —Z—N(R$^{22}$)—, —Z—S(O)$_n$— or —Z—O— (in which, in each case, the group Z represents C$_{1-4}$ alkylene attached to the carbon atom bearing R$^3$) and Y represents O may be prepared by reduction of a compound of formula XXXIIA or XXXIIB,

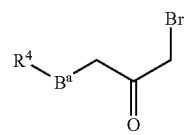

XXXIIA

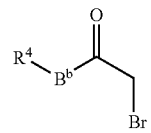

XXXIIB wherein B$^a$ represents —Z$^a$—N(R$^{22}$), —Z$^a$—S(O)$_n$— or —Z$^a$—O— (in which, in each case, the group Z$^a$ represents a direct bond or C$_{1-3}$ alkylene attached to the carbon atom bearing R$^3$), B$^b$ represents a direct bond or C$_{1-4}$ alkylene, and R$^4$, R$^{22}$ and n are as hereinbefore defined, for example at between −15° C. and room temperature in the presence of a suitable reducing agent (e.g. NaBH$_4$) and an appropriate organic solvent (e.g. THF), followed by an internal displacement reaction in the resultant intermediate, for example at room temperature in the presence of a suitable base (e.g. potassium carbonate) and an appropriate organic solvent (e.g. acetonitrile);

(3) B represents a direct bond, C$_{1-4}$ alkylene, —Z—N(R$^{22}$)—, —Z—S(O)$_2$— or —Z—O— (in which, in each case, the group Z represents C$_{1-4}$ alkylene attached to the carbon atom bearing R$^3$) and Y represents O may be prepared by oxidation of a compound of formula XXXIIIA or XXXIIIB,

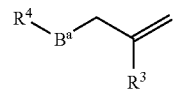

XXXIIIA

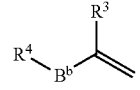

XXXIIIB wherein R$^3$, R$^4$ and B$^b$ are as hereinbefore defined, and B$^a$ is as hereinbefore defined except that n represents 2, in the presence of a suitable oxidising agent (e.g. mCPBA), for example by refluxing in the presence of a suitable organic solvent (e.g. dichloromethane); or (4) B represents —Z—O—, in which group Z represents C$_{1-4}$ alkylene attached to the carbon atom bearing R$^3$, and Y represents —N(R$^{17}$), wherein R$^{17}$ represents —C(O)OR$^{19b}$ or —S(O)$_2$R$^{19c}$, may be prepared by cyclisation of a compound of formula XXXIV,

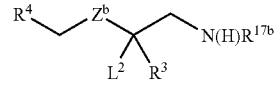

XXXIV wherein R$^{17b}$ represents —C(O)OR$^{19b}$ or —S(O)$_2$R$^{19c}$, Z$^b$ represents C$_{1-4}$ alkylene and R$^3$, R$^4$, R$^{19b}$, R$^{19c}$ and L$^2$ are as hereinbefore defined, for example at between 0° C. and reflux temperature in the presence of a suitable base (e.g. sodium hydroxide), an appropriate solvent (e.g. dichloromethane, water, or a mixture thereof) and, if necessary, a phase transfer catalyst (such as tetrabutylammonium hydrogensulfate).

Compounds of formula VI, IX, XI and XV may be prepared in a similar fashion to compounds of formula I (see, for example process steps (a) to (c)).

Compounds of formula XI may alternatively be prepared by reaction of corresponding compounds of formula I in which $R^2$ represents —E—OH with a compound of formula XXXV,

   XXXV wherein $R^{28}$ represents $C_{1-4}$ alkyl or aryl (which two groups are optionally substituted by one or more substituents selected from $C_{1-4}$ alkyl, halo and nitro), for example at between −10 and 25° C. in the presence of a suitable solvent (e.g. dichloromethane), followed by reaction with a suitable source of the azide ion (e.g. sodium azide), for example at between ambient and reflux temperature in the presence of an appropriate solvent (e.g. N,N-dimethylformamide) and a suitable base (e.g. sodium hydrogencarbonate).

Compounds of formula XI may also be prepared by reaction of a compound of formula II, as hereinbefore defined, with a compound of formula XXXVI,

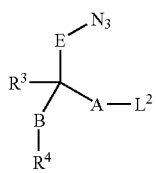   XXXVI wherein $R^3$, $R^4$, A, B, E and $L^2$ are as hereinbefore defined, for example under analogous conditions to those described hereinbefore for the synthesis of compounds of formula I (process step (a)).

Compounds of formula XV may alternatively be prepared by replacement of the —OH group of a corresponding compound of formula I in which $R^2$ represents —E—OH with an $L^2$ group under conditions that are known to those skilled in the art.

Compounds of formula XVII may be prepared by reaction of a corresponding compound of formula XXIV, as hereinbefore defined, with a compound of formula III, as hereinbefore defined, for example under analogous conditions to those described hereinbefore for the synthesis of compounds of formula I (process step (a)).

Compounds of formula XVII in which A represents $C_2$ alkylene and $R^2$ and $R^3$ together represent =O may be prepared by reaction of a corresponding compound of formula XXIV, as hereinbefore defined, with a compound of formula IV, as hereinbefore defined, for example as described hereinbefore for synthesis of compounds of formula I (process step (b)).

Compounds of formula XVII in which A represents $CH_2$ and $R^2$ represents —OH or —N(H)$R^{17}$ may be prepared by reaction of a corresponding compound of formula XXIV, as hereinbefore defined, with a compound of formula V as hereinbefore defined, for example as described hereinbefore for synthesis of compounds of formula I (process step (c)).

Compounds of formula XIX may be prepared by reaction of a corresponding compound of formula II, as hereinbefore defined, with a compound of formula XXXVII,

   XXXVII wherein $L^5$ is as hereinbefore defined, and in which the two $L^5$ groups may be the same or different, for example at between 0° C. and reflux temperature in the presence of a suitable base (e.g. triethylamine or potassium carbonate) and an appropriate organic solvent (e.g. toluene or dichloromethane).

Compounds of formula XXIV in which $R^a$ and $R^b$ both represent H may be prepared by reduction of a corresponding compound of formula XXXVIII,

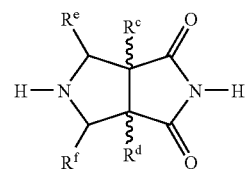   XXXVIII or an N-protected derivative thereof, wherein $R^c$ to $R^f$ are as hereinbefore defined, for example at between room and reflux temperature in the presence of a suitable reducing agent (e.g. LiAlH$_4$) and an appropriate organic solvent (e.g. THF).

Compounds of formula XXIV in which $R^a$ and $R^b$ both represent H may alternatively be prepared by reaction of a corresponding compound of formula XXXIX,

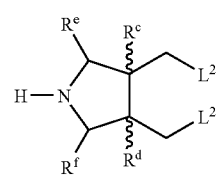   XXXIX or an N-protected derivative thereof, wherein $R^c$ to $R^f$ and $L^2$ are as hereinbefore defined, with ammonia or a protected derivative thereof (e.g. benzylamine), for example under conditions as described in International Patent Application WO 96/07656, the disclosures in which document are hereby incorporated by reference (e.g. at between room and reflux temperature in the presence of a suitable solvent (e.g. a lower alkyl alcohol (such as methanol) or DMF)).

The compound of formula XXIV in which $R^c$ and $R^d$ both represent methyl and $R^a$, $R^b$, $R^e$ and $R^f$ all represent H may alternatively be prepared according to the procedure described in *J. Org. Chem.* 61, 8897 (1996), the disclosures of which document are hereby incorporated by reference.

Compounds of formula XXIX in which B represents $C_{1-4}$ alkylene may be prepared by coupling a compound of formula XL,

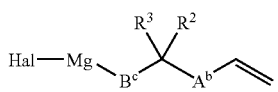

XL wherein $B^c$ represents $C_{1-4}$ alkylene, Hal represents chloro, bromo or iodo, and $A^b$, $R^2$ and $R^3$ are as hereinbefore defined, with a compound of formula VIII, as hereinbefore defined, for example at between −25° C. and room temperature in the presence of a suitable zinc(II) salt (e.g. anhydrous $ZnBr_2$), an appropriate catalyst (e.g. $Pd(PPh_3)_4$ or $Ni(PPh_3)_4$) and a reaction-inert organic solvent (e.g. THF, toluene or diethyl ether).

Compounds of formula XXXVI may be prepared in analogous fashion to compounds of formula XI (i.e. from the corresponding alcohol).

Compounds of formula XXXVIII in which $R^c$ and $R^d$ both represent H may be prepared by reduction of corresponding compound of formula XLI,

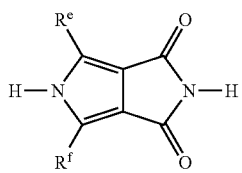

XLI or an N-protected or N,N'-diprotected derivative thereof, for example as described in *J. Heterocyclic Chem.* 20, 321 (1983), the disclosures in which document are hereby incorporated by reference (e.g. hydrogenation at elevated pressure (e.g. 25 to 35 kPa) in the presence of a suitable catalyst (e.g. palladium on carbon) and a suitable solvent (e.g. glacial acetic acid)).

Compounds of formula XXXVIII may alternatively be prepared by coupling a compound of formula XLIIA or XLIIB,

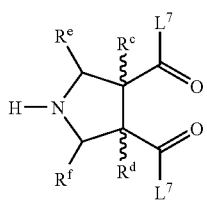

XLIIA

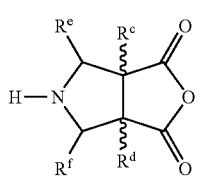

XLIIB or an N-protected derivative thereof, wherein $L^7$ represents a leaving group (such as halo or —OH) and $R^c$ to $R^f$ are as hereinbefore defined, with ammonia or a protected derivative thereof (e.g. benzylamine), for example under conditions that are well known to those skilled in the art (e.g.

where the reactant is a compound of formula XLIIB, reaction may be performed at between room and reflux temperature in the presence of a suitable solvent (such as THF)), followed by cyclisation of the resultant amide intermediate under conditions that are well known to those skilled in the art (e.g. by reaction with a dehydrating agent such as $SOCl_2$).

Compounds of formula XXXVIII may also be prepared by reaction of a compound of formula XLIII,

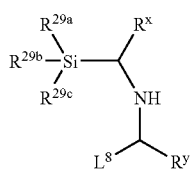

XLIII or an N-protected (e.g. N-benzyl) derivative thereof, wherein $L^8$ represents a suitable leaving group (such as lower alkoxy (e.g. methoxy) or cyano), $R^{29a}$ to $R^{29c}$ independently represent $C_{1-6}$ alkyl or phenyl, $R^x$ represents $R^e$ or $R^f$, $R^y$ represents $R^f$ or $R^e$ (as appropriate), and $R^e$ and $R^f$ are as hereinbefore defined, with a compound of formula XLIV,

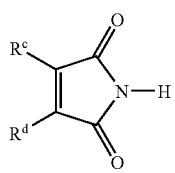

XLIV or an N-protected (e.g. N-benzyl) derivative thereof, wherein $R^c$ and $R^d$ are as hereinbefore defined, for example under conditions identical or analogous to those described in International Patent Application WO 97/11945 and *Tetrahedron* 41(17), 3529 (1985), the disclosures in which documents are hereby incorporated by reference (e.g. at between room and reflux temperature in the presence of a suitable solvent (e.g. dichloromethane) and an appropriate catalyst (e.g. an acid such as trifluoroacetic acid or a source of the fluoride ion such as tetrabutylammonium fluoride or silver fluoride)).

Compounds of formula XXXIX may be prepared by reaction of a diester of a maleic acid, such as a compound of formula XLV,

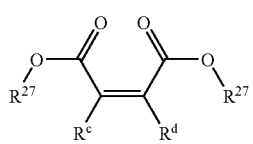

XLV wherein $R^{27}$, $R^c$ and $R^d$ are as hereinbefore defined, with a compound of formula XLVI,

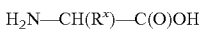

$H_2N$—$CH(R^x)$—$C(O)OH$          XLVI wherein $R^x$ is as hereinbefore defined, in the presence of a compound of formula XLVII, $$R^yCHO \quad XLVII$$

wherein $R^y$ is as hereinbefore defined, for example under conditions identical or analogous to those described in International Patent Applications WO 96/07656 and WO 95/15327, the disclosures in which documents are hereby incorporated by reference, followed by conversion of the two —C(O)OR$^{27}$ groups in the resultant intermediate to —CH$^2$—L$^2$ groups under conditions that are well known to those skilled in the art.

Compounds of formula XLI may be prepared by coupling of a compound of formula XLVIIIA or XLVIIIB,

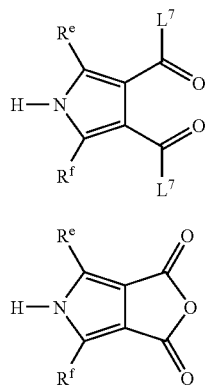

or an N-protected (e.g. N-benzyl) derivative thereof, wherein $R^e$, $R^f$ and $L^7$ are as hereinbefore defined, with ammonia or a protected derivative thereof (e.g. benzylamine), for example under conditions as described herein in respect of the preparation of compounds of formula XVIII, followed by cyclisation of the resultant amide intermediate under conditions known to those skilled in the art.

Compounds of formula XLIIA may be prepared by reaction of a corresponding compound of formula XLV with either:

(1) a compound of formula XLIII, as hereinbefore defined, or an N-protected (e.g. N-benzyl) derivative thereof, for example under conditions as described hereinbefore in respect of the preparation of compounds of formula XXXVIII, followed by conversion of the two —C(O)OR$^{27}$ groups in the resultant intermediate to —C(O)L$^7$ groups under conditions well known to those skilled in the art (e.g. for compounds of formula XLIIA in which $L^7$ represents OH, hydrolysis in the presence of an alkali metal base (such as KOH) and a suitable solvent (e.g. ethanol, water or mixtures thereof)); or (2) a compound of formula XLVI, as hereinbefore defined, in the presence of a compound of formula XLVII, as hereinbefore defined, for example under conditions as described hereinbefore in respect of the preparation of compounds of formula XXXIX, followed by conversion of the two —C(O)OR$^{27}$ groups in the resultant intermediate to —C(O)L$^7$ groups under conditions well known to those skilled in the art.

Compounds of formula XLIIB may be prepared by reaction of a corresponding compound of formula XLIX,

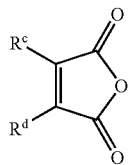

wherein $R^c$ and $R^d$ are as hereinbefore defined, with either:

(1) a compound of formula XLIII, as hereinbefore defined, or an N-protected (e.g. N-benzyl) derivative thereof, for example under conditions as described hereinbefore in respect of the preparation of compounds of formula XXXVIII; or (2) a compound of formula XLVI, as hereinbefore defined, in the presence of a compound of formula XLVII, as hereinbefore defined, for example under conditions as described hereinbefore in respect of the preparation of compounds of formula XXXIX.

Compounds of formula XLIIB may alternatively be prepared by cyclisation of a corresponding compound of formula XLIIA in which $L^7$ represents OH, for example under conditions well known to those skilled in the art (e.g. by reaction with a dehydrating agent (such as N,N'-dicyclohexylcarbodiimide) in the presence of a suitable solvent (such as THF)).

Compounds of formula XLIII may be prepared by reaction of a corresponding compound of formula L,

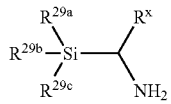

or an N-protected (e.g. N-benzyl) derivative thereof, wherein $R^x$, and $R^{29a}$ to $R^{29c}$ are as hereinbefore defined, with a compound of formula XLVII, as hereinbefore defined, in the presence of either a lower alkyl alcohol such as methanol (to produce a compound of formula XLIII in which $L^8$ represents lower alkoxy; for example under conditions identical or analogous to those described in International Patent Application WO 97/11945 (e.g. at between 0° C. and room temperature in the presence of water)) or a source of the cyanide ion such as potassium cyanide (to produce a compound of formula XLIII in which $L^8$ represents cyano, for example under conditions identical or analogous to those described in *Tetrahedron* 41(17), 3529 (1985)).

Compounds of formulae XLVIIIA and XLVIIIB may be prepared by known techniques, for example according to the procedures described in *J. Heterocyclic Chem.* 20, 321 (1983).

Compounds of formula L may be prepared by known techniques, for example according to the procedures described in International Patent Application WO 97/11945.

Compounds of formulae IV, VII, VIII, X, XII, XIII, XIV, XVI, XVIII, XX, XXI, XXII, XXIII, XXV, XXVI, XXVII, XXVIII, XXX, XXXI, XXXIIA, XXXIIB, XXXIIIA, XXXIIIB, XXXIV, XXXV, XXXVII, XL, XLIV, XLV, XLVI, XLVII, XLIX and derivatives thereof, are either commercially available, are known in the literature, or may be obtained either by analogy with the processes described herein, or by conventional synthetic procedures, in accordance with standard techniques, from readily available starting materials using appropriate reagents and reaction conditions. For example, transformations giving compounds of formula I (e.g. process steps (d), (e), (f), (j), (k), (l), (m), (n), (o), (p), (q), (v), (y) and (z)) may, where appropriate, be performed on intermediate compounds disclosed herein (e.g. compounds of formulae II, VI, IX, XI, XV, XVII and XIX) to give other intermediates that are useful in the synthesis of compounds of formula I.

Substituents on the aryl (e.g. phenyl), and (if appropriate) heterocyclic, group(s) in compounds defined herein may be converted to other claimed substituents using techniques well known to those skilled in the art. For example, hydroxy may be converted to alkoxy, phenyl may be halogenated to give halophenyl, nitro may be reduced to give amino, halo may be displaced by cyano, etc.

The skilled person will also appreciate that various standard substituent or functional group interconversions and transformations within certain compounds of formula I will provide other compounds of formula I. For example, carbonyl may be reduced to hydroxy or alkylene, and hydroxy may be converted to halo.

The compounds of the invention may be isolated from their reaction mixtures using conventional techniques.

It will be appreciated by those skilled in the art that, in the process described above, the functional groups of intermediate compounds may be, or may need to be, protected by protecting groups.

Functional groups which it is desirable to protect include hydroxy, amino and carboxylic acid. Suitable protecting groups for hydroxy include trialkylsilyl and diarylalkylsilyl groups (e.g. tert-butyldimethylsilyl, tert-butyldiphenylsilyl or trimethylsilyl), tetrahydropyranyl and alkylcarbonyl groups (e.g. methyl- and ethylcarbonyl groups). Suitable protecting groups for amino include benzyl, sulfonamido (e.g. benzenesulfonamido), tert-butyloxycarbonyl, 9-fluorenylmethoxycarbonyl or benzyloxycarbonyl. Suitable protecting groups for amidino and guanidino include benzyloxycarbonyl. Suitable protecting groups for carboxylic acid include $C_{1-6}$ allyl or benzyl esters.

The protection and deprotection of functional groups may take place before or after any of the reaction steps described hereinbefore.

Protecting groups may be removed in accordance with techniques which are well known to those skilled in the art and as described hereinafter;

The use of protecting groups is fully described in "Protective Groups in Organic Chemistry", edited by J. W. F. McOmie, Plenum Press (1973), and "Protective Groups in Organic Synthesis", 3$^{rd}$ edition, T. W. Greene & P. G. M. Wutz, Wiley-Interscience (1999).

Persons skilled in the art will appreciate that, in order to obtain compounds of the invention in an alternative, and, on some occasions, more convenient, manner, the individual process steps mentioned herein may be performed in a is different order, and/or the individual reactions may be performed at a different stage in the overall route (i.e. substituents may be added to and/or chemical transformations performed upon, different intermediates to those associated hereinbefore with a particular reaction). This will depend inter alia on factors such as the nature of other functional groups present in a particular substrate, the availability of key intermediates and the protecting group strategy (if any) to be adopted. Clearly, the type of chemistry involved will influence the choice of reagent that is used in the said synthetic steps, the need, and type, of protecting groups that are employed, and the sequence for accomplishing the synthesis.

It will also be appreciated by those skilled in the art that, although certain protected derivatives of compounds of formula I, which may be made prior to a final deprotection stage, may not possess pharmacological activity as such, they may be administered parenterally or orally and thereafter metabolised in the body to form compounds of the invention which are pharmacologically active. Such derivatives may therefore be described as "prodrugs". Moreover, certain compounds of formula I may act as prodrugs of other compounds of formula I.

All prodrugs of compounds of formula I are included within the scope of the invention.

Those skilled in the art will also appreciate that certain compounds of formula I will be useful as intermediates in the synthesis of certain other compounds of formula I.

Some of the intermediates referred to hereinbefore are novel. According to a further aspect of the invention there is thus provided: (a) a compound of formula II, as hereinbefore defined (provided that when $R^a$ to $R^f$ all represent H, then $R^1$ does not represent (i) $C_{1-12}$ alkyl optionally substituted by aryl or Het$^1$,(ii) —C(O)-(optionally substituted aryl), or (iii) tert-butyloxycarbonyl), or a protected derivative thereof; (b) a compound of formula VI, as hereinbefore defined, or a protected derivative thereof; (c) a compound of formula IX, as hereinbefore defined, or a protected derivative thereof; (d) a compound of formula XI, as hereinbefore defined, or a protected derivative thereof; (e) a compound of formula XV, as hereinbefore defined, or a protected derivative thereof; (f) a compound of formula XVII, as hereinbefore defined (provided that when B represents Z, then $R^2$ represents —E—O-(optionally substituted aryl)), or a protected derivative thereof; and (g) a compound of formula XIX, as hereinbefore defined, or a protected derivative thereof Compounds of formula II that may be mentioned include those in which:

(a) when $R^1$ represents —C(O)XR$^7$, then:
    $R^7$ does not represent unsubstituted $C_{1-12}$ alkyl;
    $R^7$ represents aryl;.
    X represents S;
(b) when $R^a$ to $R^f$ all represent H, then $R^1$ does not represent:
    (i) —C(O)XR$^7$;
    (ii) unsubstituted, straight-chain or branched $C_{1-4}$ alkyl;
    (iii) unsubstituted straight-chain or branched $C_{1-5}$ alkyl;
    (iv) straight-chain or branched $C_{1-4}$ alkyl substituted by phenyl (which latter group is mono- or di-substituted by one of fluoro, chloro, bromo, methyl or methoxy);
    (v) straight-chain or branched $C_{1-4}$ alkyl substituted by one of fluoro, chloro, bromo, methyl or phenyl (which latter group is substituted by one or two methoxy groups);
    (vi) straight-chain or branched $C_{1-4}$ alkyl substituted by one of fluoro, chloro, bromo, methyl, methoxy or phenyl;
    (vii) straight-chain or branched $C_{1-4}$ alkyl substituted by halo, methyl, methoxy or aryl;
(c) $R^1$ represents:
    (i) Het$^2$, —C(O)R$^{5a}$, —C(O)XR$^7$, —C(O)N(R$^8$)R$^{5d}$, —S(O)$_2$R$^9$, unsubstituted, cyclic or part-cyclic/acyclic $C_{4-12}$ alkyl, or $C_{1-4}$ alkyl substituted or terminated by, or $C_{5-12}$ alkyl optionally substituted and/or terminated by, one or more groups selected from
    halo,
    cyano,
    nitro, phenyl (which latter group is optionally substituted by —OH, cyano, nitro, $C_{2-6}$ alkyl (optionally terminated by —N(H)C(O)OR$^{23a}$), $C_{2-6}$ alkoxy, Het$^1$, aryl (which aryl group may not be substituted with any further aryl groups), —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)$_2$R$^{23d}$ and —S(O)$_2$N(R$^{24n}$)R$^{24p}$), naphthyl (which latter group is optionally substituted by one or more groups selected from —OH, cyano, halo, nitro, $C_{1-6}$ alkyl (optionally terminated by —N(H)C(O)OR$^{23a}$), $C_{1-6}$ alkoxy, Het$^1$, aryl (which aryl group may not be substituted with any further aryl groups), —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)$_2$R$^{23d}$ and —S(O)$_2$N(R$^{24n}$)R$^{24p}$)

Het$^1$,
—C(O)R$^{5a}$,
—OR$^{5b}$,
—N(R$^6$)R$^{5c}$,
—C(O)XR$^7$,
—C(O)N(R$^8$)R$^{5d}$ and
—S(O)$_2$R$^9$;

(ii) Het$^2$, —C(O)R$^{5a}$, —C(O)XR$^7$, —C(O)N(R$^8$)R$^{5d}$, —S(O)$_2$R$^9$, unsubstituted, cyclic or part-cyclic/acyclic $C_{4-12}$ alkyl, or $C_{1-5}$ alkyl substituted or terminated by, or $C_{6-12}$ alkyl optionally substituted and/or terminated by, one or more groups selected from
cyano,
nitro,
phenyl (which latter group is optionally substituted by —OH, halo, cyano, nitro, $C_{1-6}$ alkyl (optionally terminated by —N(H)C(O)OR$^{23a}$), $C_{2-6}$ alkoxy, Het$^1$, aryl (which aryl group may not be substituted with any further aryl groups), —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)R$_{23d}$ and —S(O)$_2$N(R$^{24n}$)R$^{24p}$), naphthyl (which latter group is optionally substituted by one or more groups selected from —OH, cyano, halo, nitro, $C_{1-6}$ alkyl (optionally terminated by —N(H)C(O)OR$^{23a}$), $C_{1-6}$ alkoxy, Het$^1$, aryl (which aryl group may not be substituted with any further aryl groups), —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)$_2$R$^{23d}$ and —S(O)$_2$N(R$^{24n}$)R$^{24p}$)

Het$^1$,
—C(O)R$^{5a}$,
—OR$^{5b}$,
—N(R$^6$)R$^{5c}$,
—C(O)XR$^7$,
—C(O)N(R)R$^{5d}$ and
—S(O)$_2$R$^9$;

(iii) Het$^2$, —C(O)R$^{5a}$, —C(O)X$^7$, —C(O)N(R$^8$)R$^{5d}$, —S(O)$_2$R$^9$, unsubstituted, cyclic or part-cyclic/acyclic $C_{4-12}$ alkyl, or $C_{1-4}$ alkyl substituted or terminated by, or $C_{5-12}$ alkyl optionally substituted and/or terminated by, one or more groups selected from, halo, cyano, nitro, Het$^1$, —C(O)R$^{5a}$, —OR$^{5b}$, —N(R$^6$)R$^{5c}$, —C(O)XR$^7$, —C(O)N(R$^8$)R$^{5d}$ and —S(O)$_2$R$^9$;

(iv) Het$^2$, —C(O)R$^{5a}$, —C(O)XR$^7$, —C(O)N(R$^8$)R$^{5d}$, —S(O)$_2$R$^9$, unsubstituted, cyclic or part-cyclic/acyclic $C_{4-12}$ alkyl, or $C_{1-5}$ alkyl substituted or terminated by, or $C_{6-12}$ alkyl optionally substituted and/or terminated by, one or more groups selected from, cyano, nitro, Het$^1$; —C(O)R$^{5a}$, —N(R$^6$)R$^{5c}$, —C(O)XR$^7$, —C(O)N(R$^8$)R$^{5d}$, —S(O)$_2$R$^9$ and —OR$^{5b}$(wherein R$^{5b}$ represents H, $C_{2-6}$ alkyl (optionally substituted and/or terminated by one or more substituents selected from —OH, $C_{1-6}$ alkoxy, halo, cyano, nitro, aryl, Het$^3$ and —NHC(O)R$^{10}$), aryl or Het$^4$).

Compounds of formula XVII that may be mentioned include those in which:

(a) when R$^a$ to R$^f$ all represent H and the group —A—C(R$^2$)(R$^3$)—B— represents $C_{1-4}$ alkylene, then R$^4$ does not represent a phenyl group that is mono- or di-substituted by one of fluoro, chloro, bromo, methyl or methoxy;

(b) when R$^a$ to R$^f$ all represent H and the group —A—C(R$^2$)(R$^3$)—B— represents $C_{1-5}$ alkylene, or $C_{1-4}$ alkylene substituted by halo, then R$^4$ does not represent a phenyl group that is mono- or di-substituted by methoxy;

(c) R$^4$ represents naphthyl or Het$^{13}$, both of which groups are optionally substituted by one or more substituents selected from —OH, cyano, halo, nitro, $C_{1-6}$ alkyl (optionally terminated by —N(H)C(O)OR$^{23a}$), $C_{1-6}$ alkoxy, Het$^1$, aryl, —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)$_2$R$^{23d}$, —S(O)$_2$N(R$^{24n}$)R$^{24p}$ and (in the case of Het$^{13}$ only) oxo, or R$^4$ represents phenyl substituted by or more substituents selected from —OH, cyano, nitro, $C_{2-6}$ alkyl (optionally terminated by —N(H)C(O)OR$^{23a}$), $C_{2-6}$ alkoxy, Het$^1$, aryl, —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)$_2$R$^{23d}$ and —S(O)$_2$N(R$^{24n}$)R$^{24p}$.

Medical and Pharmaceutical Use

Compounds of the invention are useful because they possess pharmacological activity. They are therefore indicated as pharmaceuticals.

Thus, according to a further aspect of the invention there is provided the compounds of the invention for use as pharmaceuticals.

In particular, the compounds of the invention exhibit myocardial electrophysiological activity, for example as demonstrated in the tests described below.

The compounds of the invention are thus expected to be useful in both the prophylaxis and the treatment of arrhythmias, and in particular atrial and ventricular arrhythmias.

The compounds of the invention are thus indicated in the treatment or prophylaxis of cardiac diseases, or in indications related to cardiac diseases, in which arrhythmias are believed to play a major role, including ischaemic heart disease, sudden heart attack, myocardial infarction, heart failure, cardiac surgery and thromboembolic events.

In the treatment of arrhythmias, compounds of the invention have been found to selectively delay cardiac repolarization, thus prolonging the QT interval, and, in particular, to exhibit class III activity. Although compounds of the invention have been found to exhibit class III activity in particular, in the treatment of arrhythmias, their mode(s) of activity is/are not necessarily restricted to this class.

According to a further aspect of the invention, there is provided a method of treatment of an arrhythmia which method comprises administration of a therapeutically effective amount of a compound of the invention to a person suffering from, or susceptible to, such a condition.

Pharmaceutical Preparations

The compounds of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

The compounds of the invention may also be combined with any other drugs useful in the treatment of arrhythmias and/or other cardiovascular disorders.

According to a further aspect of the invention there is thus provided a pharmaceutical formulation including a compound of the invention in admixture with a pharmaceutically acceptable adjuvant, diluent or carrier.

Suitable daily doses of the compounds of the invention in therapeutic treatment of humans are about 0.005 to 25.0 mg/kg body weight at oral administration and about 0.005 to 10.0 mg/kg body weight at parenteral administration. Preferable ranges of daily doses of the compounds of the invention in therapeutic treatment of humans are about 0.005 to 10.0 mg/kg body weight at oral administration and about 0.005 to 5.0 mg/kg body weight at parenteral administration.

The compounds of the invention have the advantage that they are effective against cardiac arrhythmias.

Compounds of the invention may also have the advantage that they may be more efficacious than, be less toxic than, have a broader range of activity (including exhibiting any combination of class I, class II, class III and/or class IV activity (especially class I and/or class IV activity in addition to class III activity)) than, be more potent than, be longer acting than, produce fewer side effects (including a lower incidence of proarrhythmias such as torsades de pointes) than, be more easily absorbed than, or that they may have other useful pharmacological properties over, compounds known in the prior art.

Biological Tests

Test A

Primary Electrophysiological Effects in Anaesthetised Guinea Pigs

Guinea pigs weighing between 660 and 1100 g were used. The animals were housed for at least one week before the experiment and had free access to food and tap water during that period.

Anaesthesia was induced by an intraperitoneal injection of pentobarbital (40 to 50 mg/kg) and catheters were introduced into one carotid artery (for blood pressure recording and blood sampling) and into one jugular vein (for drug infusions). Needle electrodes were placed on the limbs for recording of ECGs (lead II). A thermistor was placed in the rectum and the animal was placed on a heating pad, set to a rectal temperature of between 37.5 and 38.5° C.

A tracheotomy was performed and the animal was artificially ventilated with room air by use of a small animal ventilator, set to keep blood gases within the normal range for the species. In order to reduce autonomic influences both vagi were cut in the neck, and 0.5 mg/kg of propranolol was given intravenously, 15 minutes before the start of the experiment.

The left ventricular epicardium was exposed by a left-sided thoracotomy, and a custom-designed suction electrode for recording of the monophasic action potential (MAP) was applied to the left ventricular free wall. The electrode was kept in position as long as an acceptable signal could be recorded, otherwise it was moved to a new position. A bipolar electrode for pacing was clipped to the left atrium. Pacing (2 ms duration, twice the diastolic threshold) was performed with a custom-made constant current stimulator. The heart was paced at a frequency just above the normal sinus rate during 1 minute every fifth minute throughout the study.

The blood pressure, the MAP signal and the lead II ECG were recorded on a Mingograph ink-jet recorder (Siemens-Elema, Sweden). All signals were collected (sampling frequency 1000 Hz) on a PC during the last 10 seconds of each pacing sequence and the last 10 seconds of the following minute of sinus rhythm. The signals were processed using a custom-made program developed for acquisition and analysis of physiological signals measured in experimental animals (see Axenborg and Hirsch, Comput. Methods Programs Biomed. 41, 55 (1993)).

The test procedure consisted of taking two basal control recordings, 5 minutes apart, during both pacing and sinus rhythm. After the second control recording, the first dose of the test substance was infused in a volume of 0.2 mL into the jugular vein catheter for 30 seconds. Three minutes later, pacing was started and a new recording was made. Five minutes after the previous dose, the next dose of test substance was administered. Six to ten consecutive doses were given during each experiment.

Data Analysis

Of the numerous variables measured in this analysis, three were selected as the most important for comparison and selection of active compounds. The three variables selected were the MAP duration at 75 percent repolarization during pacing, the atrio-ventricular (AV) conduction time (defined as the interval between the atrial pace pulse and the start of the ventricular MAP) during pacing, and the heart rate (defined as the RR interval during sinus rhythm). Systolic and diastolic blood pressure were measured in order to judge the haemodynamic status of the anaesthetised animal. Further, the ECG was checked for arrhythmias and/or morphological changes.

The mean of the two control recordings was set to zero and the effects recorded after consecutive doses of test substance were expressed as percentage changes from this value. By plotting these percentage values against the cumulative dose administered before each recording, it was possible to construct dose-response curves. In this way, each experiment generated three dose-response curves, one for MAP duration, one for AV-conduction time and one for the sinus frequency (RR interval). A mean curve of all experiments performed with a test substance was calculated, and potency values were derived from the mean curve. All dose-response curves in these experiments were constructed by linear connection of the data points obtained. The cumulative dose prolonging the MAP duration by 10% from the baseline was used as an index to assess the class III electrophysiological potency of the agent under investigation ($D_{10}$).

Test B

Glucocorticoid-Treated Mouse Fibroblasts as a Model to Detect Blockers of the Delayed Rectifier K Current IC50 for K channel blockade was determined using a microtitre plate based screen method, based on membrane potential changes of glucocorticoid-treated mouse fibroblasts. The membrane potential of glucocorticoid-treated mouse fibroblasts was measured using fluorescence of the bisoxonol dye DiBac$_{4(3)}$, which could be reliably detected using a fluorescence laser imaging plate reader (FLIPR). Expression of a delayed rectifier potassium channel was induced in mouse fibroblasts by 24 hours exposure to the glucocorticoide dexamehasone (5 μM). Blockade of these potassium channels depolarised the fibroblasts, resulting in increased fluorescence of DiBac$_{4(3)}$.

Mouse 1tk fibroblasts (L-cells) were purchased from American Type Culture Collection (ATCC, Manassa, Va.), and were cultured in Dulbeccos modified eagle medium supplemented with fetal calf serum (5% vol/vol), penicillin (500 units/mL), streptomycin (500 μg/mL) and L-alanine-L-glutamine (0.862 mg/mL). The cells were passaged every 3–4 days using trypsin (0.5 mg/mL in calcium-free phosphate buffered saline, Gibco BRL). Three days prior to experiments, cell-suspension was pipetted out into clear-bottom, black plastic, 96-well plates (Costar) at 25 000 cells/well.

The fluorescence probe DiBac$_{4(3)}$ (DiBac Molecular probes) was used to measure membrane potential. DiBac$_{4(3)}$ maximally absorbs at 488 nM and emits at 513 nM. DiBac$_{4(3)}$ is a bisoxonol, and thus is negatively charged at pH 7. Due to its negative charge, the distribution of DiBac$_{4(3)}$ across the membrane is dependent upon the transmembrane potential: if the cell depolarizes (i.e. the cell interior becomes less negative relative to cell exterior), the DiBac$_{4(3)}$ concentration inside the cell increases, due to electrostatic forces. Once inside the cell, DiBac$_{4(3)}$ molecules can bind to lipids and proteins, which causes an increase in fluorescence emission. Thus, a depolarization will be reflected by an increase in DiBac$_{4(3)}$ fluorescence. The change in DiBac$_{4(3)}$ fluorescence was detected by a FLIPR.

Prior to each experiment, the cells were washed 4 times in phosphate-buffered saline (PBS) to remove all culture media. The cells were then treated with 5 μM DiBac$_{4(3)}$ (in 180 μL of PBS) at 35° C. Once a stable fluorescence was reached (usually after 10 min), 20 μL of the test substance was added, using FLIPR's internal 96 well pipetting system. Fluorescence measurements were then taken every 20 sec for a further 10 min. All experiments were carried out at 35° C., due to the high temperature sensitivity of both delayed rectifier potassium channel conductance and DiBac$_{4(3)}$ fluorescence. Test substances were prepared in a second 96 well plate, in PBS containing 5 μM DiBac$_{4(3)}$. The concentration of substance prepared was 10 times that of the desired concentration in the experiment as an additional 1:10 dilution occurred during addition of substance during the experiment. Dofetilide (10 μM) was used as a positive control, i.e. to determine the maximum increase in fluorescence.

Curve-fitting, used to determine the IC50 values, was performed with the Graphpad Prism program (Graphpad Software Inc., San Diego, Calif.).

Test C

Metabolic Stability of Test Compounds

An in vitro screen was set up to determine the metabolic stability of the compounds of formula I.

The hepatic S-9 fraction from dog, man, rabbit and rat with NADPH as co-factor was used. The assay conditions were as follows: S-9 (3 mg/mL), NADPH (0.83 mM), Tris-HCl buffer (50 mM) at pH 7.4 and 10 μM of test compound.

The reaction was started by addition of test compound and terminated after 0, 1, 5, 15 and 30 minutes by raising the pH in the sample to above 10 (NaOH; 1 mM). After solvent extraction, the concentration of test compound was measured against an internal standard by LC (fluorescence/UV detection).

The percentage of test compound remaining after 30 minutes (and thus $t_{1/2}$) was calculated and used as a measure for metabolic stability.

The invention is illustrated by way of the following examples.

EXAMPLES

General Experimental Procedures

Mass spectra were recorded on one of the following instruments: a Perkin-Elmer SciX API 150ex spectrometer; a VG Quattro II triple quadrupole; a VG Platform II single quadrupole; or a Micromass Platform LCZ single quadrupole mass spectrometer (the latter three instruments were equipped with a pneumatically assisted electrospray interface (LC-MS)). $^1$H NMR and $^{13}$C NMR measurements were performed on a BRUKER ACP 300 and Varian 300, 400 and 500 spectrometers, operating at $^1$H frequencies of 300, 400 and 500 MHz respectively, and at $^{13}$C frequencies of 75.5, 100.6 and 125.7 MHz respectively. Alternatively, $^{13}$C NMR measurements were performed on a BRUKER ACE 200 spectrometer at a frequency of 50.3 MHz.

Rotamers may or may not be denoted in spectra depending upon ease of interpretation of spectra. Unless otherwise stated, chemical shifts are given in ppm with the solvent as internal standard.

Synthesis of Intermediates

The following intermediates were not commercially available, and were therefore prepared by the methods described below.

Preparation A tert-Butyl hexahydropyrrolo[3,4-c]pyrrole-2(1H)-carboxylate (a) 3,7-Dibenzyl-cis-3,7-diazabicyclo[3.3.0]octan-2,4-dione Trifluoroacetic acid (1–3 mL) was added dropwise to a solution of N-(methoxymethyl)-N-trimethylsilylmethyl) benzylamine (137.0 g, 580 mmol) and N-benzylmaleimide (95.0 g, 500 mmol) in CH$_2$Cl$_2$ (1 L) until a vigorous exothermic reaction ensued. After the exothermic reaction subsided (approximately 10 min) the mixture was heated at reflux for 3 h. The reaction was cooled and then quenched with 1 N NaOH (200 mL). The organic layer was separated, washed with brine, dried with Na$_2$SO$_4$, filtered and concentrated in vacuo to afford 170.0 g of crude product. Crystallisation from isopropyl ether afforded 109.0 g (67%) of the sub-title compound.

$^1$H NMR (300 MHz, CDCl$_3$) δ 7.4–7.0 (m, 10H), 4.65 (s, 2H), 3.55 (s, 2H), 3.30 (d, 2H, J=12 Hz), 3.15 (d, 2H, J=6 Hz), 2.35 (m, 2H).

(b) 3-Benzyl-cis-3,7-diazabicyclo[3.3.0]octan-2,4-dione hydrochloride

Concentrated hydrochloric acid (28.4 mL, 341 mmol) was added to a suspension of 3,7-dibenzyl-3,7-diazabicyclo [3.3.0]octan-2,4-dione (109.0 g, 341 mmol; from step (a) above) in CH$_3$OH under a N$_2$ atmosphere. To the resulting solution there was added 10% Pd/C (w/w; 5 g). The N$_2$ atmosphere was exchanged for H$_2$ (1 atm of pressure) and the reaction was stirred for 12 h. The reaction was diluted with H$_2$O (160 mL), filtered through a pad of cellulose to remove the catalyst and the filtrate concentrated in vacuo to afford a solid. Triturating with absolute EtOH afforded 74.6 g (82%) of the sub-title compound as an off-white solid after drying in a vacuum oven at 50° C./66.5 Pa (0.5 mm Hg).

$^1$H NMR (300 MHz, CDCl$_3$) δ 7.4–7.2 (m, 5H), 4.6 (s, 2H), 3.5 (d, 2H, J=12.5 Hz), 3.25 (d, 2H, J=7.5 Hz), 3.0 (dd, 2H, J=7.5, 12.5).

(c) 3-Benzyl-cis-3,7-diazabicyclo[3.3.0]octane

3-Benzyl-3,7-diazabicyclo[3.3.0]octan-2,4-dione hydrochloride (73.8 g, 275 mmol; from step (b) above) was added in portions to a suspension of LiAlH$_4$ (83.5 g, 2.26 mol) in THF at 0° C. The reaction was slowly warmed to reflux. After refluxing for 16 h the reaction was cooled to 0° C. To the cold reaction there was added dropwise sequentially H$_2$O (84 mL), 3 M NaOH (84 mL) and H$_2$O (250 mL). The reaction was then stirred for an additional 15 minutes and filtered through a pad of Celite® to remove the inorganic salts. The filtrate was concentrated in vacuo to afford the crude product. Kugelrohr distillation (95–115° C./66.5 Pa (0.5 mm Hg)) provided 46.8 g (84%) of the sub-title compound as a colourless oil.

$^1$H NMR (300 MHz, CDCl$_3$) δ 7.3–7.2 (m, 5H), 3.51 (s, 2H), 2.9 (dd, 2H, J=6.6, 12 Hz), 2.75 (d, 12 Hz), 2.7–2.5 (m, 4H), 2.3 (d, 2H, J=7.5 Hz), 2.0 (bs, 2H).

(d) 3-Benzyl-7-(tert-butoxycarbonyl)-cis-3,7-diazabicyclo[3.3.0]octane hydrochloride A solution of di-tert-butyl-dicarbonate (65.3 g, 299 mmol) in THF (100 mL) was added dropwise to a stirred solution of 3-benzyl-3,7-diazabicyclo[3.3.0]octane (55 g, 272 mmol; from step (c) above) in THF (650 mL) at 0° C. After the addition was completed the reaction was stirred for 12 h at room temperature. The reaction was diluted with EtOAc (300 mL) and brine (300 mL). The organic layer was separated and set aside, the aqueous layer was extracted with EtOAc (5×200 mL). The combined organics were dried with Na$_2$SO$_4$, filtered and concentrated in vacuo to afford a colourless oil. The oil was dissolved in EtOAc (750 mL), cooled to 0° C. and a 1 M solution of HCl in Et$_2$O (275 mL) was added slowly. The precipitated HCl salt was collected and dried in a vacuum oven to afford 91.1 g (99%) of the sub-title compound as a off-white solid.

$^1$H NMR (300 MHz, CD$_3$OD) δ 7.6–7.4 (m, 5H), 4.4 (s, 2H), 3.8–3.6 (bs, 2H), 3.5–3.3 (bs, 4H), 3.3–3.0 (bs, 2H), 1.45 (s, 9H).

(e) tert-Butyl hexahydropyrrolo[3,4-c]pyrrole-2(1H)-carboxylate hydrochloride

To a solution of 3-benzyl-7-(tert-butoxycarbonyl)-3,7-diazabicyclo[3.3.0]-octane hydrochloride (91.1 g, 269 mmol; from step (d) above) in methanol (250 mL) under a N$_2$ atmosphere there was added 10% Pd/C (w/w; 9.8 g). The N$_2$ atmosphere was exchanged for H$_2$ (1 atm of pressure) and the reaction was stirred for 18 h. The reaction was filtered through a pad of cellulose to remove the catalyst. The filtrate was concentrated in vacuo to afford an off-white solid. The solid was slurried in EtOAc and collected. After drying in a vacuum oven for 18 h at 60° C./66.5 Pa (0.5 mm Hg) there was obtained 58.0 g (87%) of the title compound as an off-white solid.

Mp: 175–178° C.

R$_f$=0.45 (50:40:9:1, CH$_2$Cl$_2$:CHCl$_3$:MeOH:conc. NH$_4$OH).

MS (CI): m/z=213 (M+H).

$^1$H NMR (300 MHz, CD$_3$OD) δ 3.6 (m, 4H), 3.35 (dd, 2H), 3.14 (m, 4H), 1.48 (s, 9H).

$^{13}$C NMR (75 MHz, CD$_3$OD) δ156, 81.5, 50.5, 51.2, 43.0, 28.5

The corresponding free base was obtained by the following procedure:

The hydrochloride salt was dissolved in CH$_3$CN. Four equivalents of K$_2$CO$_3$ were added, along with a small amount of water. The mixture was stirred for 2 h, and then filtration and evaporation gave the base in quantitative yield.

Preparation B tert-Butyl (1S)-2-(4-cyanophenoxy)-1-(hexahydropyrrolo[3,4-c]pyrrol-2(1H)-ylmethyl)ethylcarbamate (a) 4-(2-Oxiranylmethoxy)benzonitrile The sub-title compound was prepared in 75% yield according to the procedure described International Patent Application WO 99/31100 (i.e. by reaction between p-cyanophenol and epichlorohydrin).

(b) 4-[(3-Amino-2-hydroxypropyl)oxy]benzonitrile 4-(2-Oxiranylmethoxy)benzonitrile (100 g, 0.57 mol; see step (a) above) was added to a mixture of concentrated aqueous ammonium hydroxide (500 mL) and iso-propanol (300 mL). The resulting slurry was stirred at room temperature for 3 days. The reaction mixture was filtered to remove the insoluble by product, and the filtrate was concentrated in vacuo to give a crude product, which was crystallised from acetonitrile to yield 50 g (46%) of the sub-title compound.

(c) tert-Butyl 3-(4-cyanophenoxy)-2-hydroxypropylcarbamate

A cooled (0° C.) solution of 4-[(3-amino-2-hydroxypropyl)oxy]benzonitrile (from step (b) above; 44.6 g, 0.23 mol) in THF:H$_2$O (1.5 L of 1:1) was treated with di-tert-butyl dicarbonate (53 g, 0.24 mol). The mixture was stirred at rt overnight, after which NaCl was added and the resulting organic layer separated. The water layer was extracted with ether and the combined organics were dried and concentrated in vacuo. The resulting oil (70 g) was filtered through a plug of silica, and then crystallised from diethyl ether:di-iso-propyl ether to yield 50 g of the sub-title compound.

(d) 2-[(tert-Butoxycarbonyl)amino]-1-[(4-cyanophenoxy)methyl]ethyl methanesulfonate Methanesulfonyl chloride (22.3 g 0.195 mol) was added over the course of 1.5 hours to a cooled (0° C.) solution of tert-butyl 3-(4-cyanophenoxy)-2-hydroxypropylcarbamate (from step (c) above; 51.2 g, 0.177 mol) and 4-(dimethylamino)pyridine (1.3 g, 10.6 mmol) in pyridine (250 mL), kept under an inert atmosphere. The reaction mixture was stirred for 2 h at rt before water and DCM were added. The organic layer was separated, washed with water, dried (MgSO$_4$) and concentrated in vacuo to yield 68.1 g (100%) of the sub-title compound.

(e) tert-Butyl 2-[(4-cyanophenoxy)methyl]-1-aziridinecarboxylate

A cooled (0° C.) solution of 2-[(tert-butoxycarbonyl) amino]-1-[(4-cyano-phenoxy)methyl]ethyl methanesulfonate (from step (d) above; 30.6 g, 82.6 mmol) and tetrabutylammonium hydrogensulfate (3 g, 8.8 mmol) in DCM (100 mL) was treated with 50 wt. % aqueous NaOH (60 mL) under an inert atmosphere. The resulting mixture was stirred, and the temperature was slowly allowed to rise to rt over for 4 h, and then extracted with ether. The organic layer was washed with water and concentrated in vacuo to give a residue that was purified by column chromatography (dichloromethane eluent). Crystallisation from diethyl ether: di-iso-propyl ether gave the sub-title compound in quantitative yield.

(f) tert-Butyl (2S)-2-[(4-cyanophenoxy)methyl]-1-aziridinecarboxylate

The sub-title compound was prepared according to the procedures described in steps (a) to (e) above for the synthesis of tert-butyl 2-[(4-cyanophenoxy)-methyl]-1-aziridinecarboxylate, but using (S)-(+)-epichlorohydrin in place of epichlorohydrin in step (a).

(g) Benzyl tert-butyl tetrahydropyrrolo[3,4-c]pyrrole-2,5(1H,3H)-dicarboxylate tert-Butyl hexahydropyrrolo[3,4-c]pyrrole-2(1H)-carboxylate hydrochloride (10 g, 0.04 mol; see Preparation A above) and triethylamine (14 mL, 0.1 mol) were mixed in CHCl$_3$ (100 mL). N-benzyloxy-carbonyloxy succinimide (11 g, 0.044 mol), dissolved in CHCl$_3$ (100 mL), was added at 0–5° C. The mixture was allowed to slowly reach room temperature and was stirred at rt for 5 h. The reaction mixture was washed with water, dried (Na$_2$SO$_4$) and evaporated, giving the sub-title compound in quantitative yield.

$^{13}$C NMR (CD$_3$Cl$_3$) δ 155.01, 155.64, 136.99, 128.71, 128.22, 128.13, 79.80, 67.12, 50.30, 49.88, 41.76, 28.71.

(h) Benzyl hexahydropyrrolo[3,4-c]pyrrole-2(1H)-carboxylate

Benzyl tert-butyl tetrahydropyrrolo[3,4-c]pyrrole-2,5(1H, 3H)-dicarboxylate (40 mmol; from step (a) above) was dissolved in ethyl acetate. Ethyl acetate saturated with HCl (g) (500 mL) was added at 0° C. and stirred while reaching room temperature. The solvent was evaporated and the product was dissolved in CH$_3$CN. K$_2$CO$_3$ (4 eq.) and water (2 mL) were added. The mixture was stirred for 2 h, before being filtered and evaporated to give 8 g (82%) of the subtitle compound which was used without further purification in the next step.

(i) Benzyl 5-[(2S)-2-[(tert-butoxycarbonyl)amino]-3-(4-cyanophenoxy)-propyl]hexahydropyrrolo[3,4-c]pyrrole-2(1H)-carboxylate tert-Butyl (2S)-2-[(4-cyanophenoxy)methyl]aziridine-1-carboxylate (2.5 g, 9.1 mmol; see step (f) above) and benzyl hexahydropyrrolo[3,4-c]pyrrole-2(1H)-carboxylate (2.24 g, 9.1 mmol; see step (h) above) was dissolved in isopropanol (30 mL) and was stirred at 56° C. for 24 h. The solvent was then evaporated. The product was purified by chromatography on silica (ethyl acetate, 0–5% MeOH eluant), giving 3.8 g (80%) of the sub-title compound.

MS (ES): m/z=521 (M+H)$^+$.

(j) tert-Butyl (1S)-2-(4-cyanophenoxy)-1-(hexahydropyrrolo[3,4-c]pyrrol-2(1H)-ylmethyl)ethylcarbamate Benzyl 5-[(2S)-2-[(tert-butoxycarbonyl)amino]-3-(4-cyanophenoxy)-propyl]hexahydropyrrolo[3,4-c]pyrrole-2 (1H)-carboxylate (3.6 g, 6.9 mmol; from step (i) above) was dissolved in ethanol (300 mL of 95%) and hydrogenated over 5% Pd/C (w/w). The reaction was stopped when the theoretical amount of H$_2$ (173 mL) was consumed. The mixture was filtered (through Celite®) and then evaporated. Purification by chromatography on silica (DCM, 5% MeOH eluant) gave 1.7 g (63.6%) of the title compound.

$^{13}$C NMR (CD$_3$Cl$_3$) δ 161.86, 155.48, 154.42, 136.81, 133.91, 128.36, 127.84, 127.73, 118.99, 115.21, 104.22, 79.69, 68.14, 66.64, 60.28, 55.20, 51.72, 48.72, 42.04, 41.06, 28.41.

MS (ES): m/z=387 (M+H)$^+$.

Preparation C

4-[1-(3,4-Dimethoxyphenoxy)-4-hexahydropyrrolo[3,4-c]pyrrol-2(1H)-ylbutyl]benzonitrile

(a) 4-[1-(3,4-Dimethoxyphenoxy)-3-butenyl]benzonitrile

A cooled (0° C.) mixture of 4-(1-hydroxy-3-butenyl) benzonitrile (14.6 g, 84.3 mmol) and 3,4-dimethoxyphenol (19.5 g, 125.4 mmol) in toluene (500 mL) was treated with tributylphosphine (32.14 mL of 97% purity, 25.6 g, 126.4 mmol), followed by 1,1'-(azodicarbonyl)dipiperidine (31.8 g, 126.4 mmol). After addition was complete, the reaction mixture thickened and the temperature rose to 15° C. Additional toluene was added (500 mL), and the mixture stirred at rt overnight. The precipitate of tributylphosphine oxide was then removed by filtration and the filtrate concentrated in vacuo to give 65.8 g of crude product. This was purified by chromatography on silica gel, eluting with toluene: methanol (98:2), to yield 17.9 g of the sub-title compound.

(b) 4-[1-(3,4-Dimethoxyphenoxy)-4-hydroxybutyl]benzonitrile

Borane-methyl sulfide complex (2 M in ether, 11 mL, 22 mmol) was added dropwise to a cooled (−5° C.) solution of 4-[1-(3,4-dimethoxy-phenoxy)-3-butenyl]benzonitrile (from step (a) above; 17.6 g, 56.8 mmol) in dry THF (15 mL) over a period of 15 minutes (during which time the reaction temperature rose to 0° C.). The resulting mixture was stirred at between 0 and 10° C. for 1.5 h, before being allowed to warm to rt. Stirring was continued for a further 3.5 h at this temperature before water (22 mL) and sodium perborate tetrahydrate (11 g, 66 mmol) were added. The biphasic mixture was stirred for 2 h at rt before the water layer was separated and extracted with ether. The combined organic layers were washed with brine, dried and concentrated in vacuo. The resulting residue was purified by chromatography on silica gel, eluting with IPA:ethyl acetate: heptane (5:25:76) to yield 14.5 g (77%) of the sub-title compound.

(c) 4-(4-Cyanophenyl)-4-(3,4-dimethoxyphenoxy) butyl methanesulfonate

A solution of methanesulfonyl chloride (3.4 mL, 5.0 g, 44 mmol) in DCM (15 mL) was added slowly to a cooled (−5° C.) mixture of 4-[1-(3,4-dimethoxyphenoxy)-4-hydroxybutyl]benzonitrile (from step (b) above; 11 g, 34 mmol) and triethylamine (7 mL, 5.2 g, 50.6 mmol) in DCM (50 mL), during which addition the temperature did not rise above 2° C. Stirring was continued at between 0 and 5° C. for a further 2 h before water was added. The resulting organic layer was separated, and washed with water, separated again and then dried to give the sub-title compound in 100% yield.

(d) tert-Butyl 5-[4-(4-cyanophenyl)-4-(3,4-dimethoxyphenoxy)butyl]-hexahydropyrrolo[3,4-c]pyrrole-2(1H)-carboxylate 4-(4-Cyanophenyl)-4-(3,4-dimethoxyphenoxy)butyl methanesulfonate (1.12 g, 2.8 mmol; see step (c) above), tert-butyl hexahydropyrrolo[3,4-c]-pyrrole-2(1H)-carboxylate (0.59 g, 2.8 mmol; see Preparation A above) and $Cs_2CO_3$ were mixed in $CH_3CN$ (30 mL) and stirred at rt for 3 days. The mixture was then filtered and evaporated. Purification on silica (ethyl acetate:MeOH (9:1) eluant) gave 0.9 g (60%) of the sub-title compound.

MS (ES): m/z=522 $(M+H)^+$

(e) 4-[1-(3,4-Dimethoxyphenoxy)-4-hexahydropyrrolo[3,4-c]pyrrol-2(1H)-ylbutyl]benzonitrile tert-Butyl 5-[4-(4-cyanophenyl)-4-(3,4-dimethoxyphenoxy)butyl]hexahydropyrrolo[3,4-c]pyrrole-2(1H)-carboxylate (0.9 g, 1.7 mmol; from step (d) above) was dissolved in ethyl acetate (25 mL). The solution was cooled to 0° C. Ethyl acetate (25 mL) saturated with gaseous HCl was added and the mixture was stirred at rt for 4 h. The mixture was evaporated and then dissolved in $CH_3CN$. $K_2CO_3$ (1 g) and water (0.05 mL) were added and the mixture was stirred for 2 h. The salts were filtered of and the solvent was evaporated, giving 0.71 g (100%) of the title compound.

MS (ES): m/z=421 $(M+H)^+$

Preparation D

4-{[(2)-3-Hexahydropyrrolo[3,4-c]pyrrol-2(1H)-yl-2-hydroxypropyl]-oxy}benzonitrile

(a) tert-Butyl 5-[(2S)-3-(4-cyanophenoxy)-2-hydroxypropyl]hexahydropyrrolo[3,4-c]pyrrole-2(1H)-carboxylate 4-[(2S)-Oxiranylmethoxy]benzonitrile (4.36 g, 0.025 mol; prepared as described in International Patent Application WO 99/31100) and tert-butyl hexahydropyrrolo[3,4-c]pyrrole-2(1H)-carboxylate (6.2 g, 0.025 mol; see Preparation A above) were mixed in isopropanol and stirred at 60° C. overnight. The solvent was evaporated and the product was purified by flash chromatography on silica, eluting with ethyl acetate, 10% MeOH. This gave 1.2 g (88%) of the sub-title compound.

(b) 4-{[(2S)-3-Hexahydropyrrolo[3,4-c]pyrrol-2(1H)-yl-2-hydroxypropyl]-oxy}benzonitrile The title compound was prepared in 90% yield according to the procedure described in Preparation C, step (e) above, using tert-butyl 5-[(2S)-3-(4-cyanophenoxy)-2-hydroxypropyl]hexahydropyrrolo[3,4-c]pyrrole-2(1H)-carboxylate (0.9 g, 2.3 mmol; see step (a) above) in place of tert-butyl 5-[4-(4-cyanophenyl)-4-(3,4-dimethoxyphenoxy)butyl] hexahydropyrrolo[3,4-c]-pyrrole-2(1H)-carboxylate.

Preparation E

4-[(3-Hexahydropyrrolo[3,4-c]pyrrol-2(1H)-ylpropyl)amino]benzonitrile

(a) 4-[(3-Hydroxypropyl)amino]benzonitrile

A mixture of 4-fluorobenzonitrile (12.0 g, 99.1 mmol) and 3-amino-1-propanol (59.6 g, 793 mmol) was stirred at 80° C. under an inert atmosphere for 3 hours before water (150 mL) was added. The mixture was allowed to cool to rt, and was then extracted with diethyl ether. The organic layer was separated, dried ($Na_2SO_4$), filtered and concentrated in vacuo to yield 17 g (97%) of the title compound as an oil that crystallised upon standing.

(b) 3-(4-Cyanoanilino)propyl 4-methylbenzenesulfonate

A cooled (0° C.) solution of 4-[(3-hydroxypropyl)amino]benzonitrile (from step (a) above; 17 g, 96.5 mmol) in dry MeCN (195 mL) was treated with triethylamine (9.8 g, 96.5 mmol) and then p-toluenesulfonyl chloride (20.2 g, 106 mmol). The mixture was stirred at 0° C. for 90 minutes before being concentrated in vacuo. Water (200 mL) was added to the residue, and the aqueous solution was extracted with DCM. The organic phase was dried ($Na_2SO_4$), filtered and concentrated in vacuo. The resulting residue was purified by crystallisation from iso-propanol to yield 24.6 g (77%) of the sub-title compound.

(c) tert-Butyl 5-{3-[(4-cyanophenyl)amino]propyl}hexahydropyrrolo[3,4-c]pyrrole-2(1H)-carboxylate 3-(4-Cyanoanilino)propyl 4-methylbenzenesulfonate (1.98 g, 6 mmol; see step (b) above), and tert-butyl hexahydropyrrolo[3,4-c]pyrrole-2(1H)-carboxylate (1.49 g, 6 mmol; see Preparation A above) was mixed with $K_2CO_3$ (1.93 g, 14 mmol) and $CH_3CN$ (100 mL) and then stirred at 50° C. overnight. The solvent was evaporated and the product was purified by chromatography on silica (DCM:MeOH (20:1)) to give 1.83 g (82%) of the sub-title compound.

(d) 4-[(3-Hexahydropyrrolo[3,4-c]pyrrol-2(1H)-ylpropyl)amino]benzonitrile

The title compound was prepared in quantitative yield according to the procedure described in Preparation C, step (e) above, using tert-butyl 5-{3-[(4-cyanophenyl)amino]propyl}hexahydropyrrolo[3,4-c]pyrrole-2(1H)-carboxylate (see step (c) above) in place of tert-butyl 5-[4-(4-cyanophenyl)-4-(3,4-dimethoxyphenoxy)butyl]hexahydropyrrolo[3,4-c]pyrrole-2(1H)-carboxylate.

Preparation F 4-(2-Hexahydropyrrolo[3,4-c]pyrrol-2(1H)-ylethoxy)benzonitrile (a) 4-(2-Bromoethoxy)benzonitrile A mixture of 4-cyanophenol (35.7 g, 0.3 mol), $K_2CO_3$ (41.4 g, 0.3 mol) and 1,2-dibromoethane (561 g, 3.0 mol) in MeCN (450 mL) was stirred under reflux overnight. The mixture was filtered and evaporated to give 30.2 g (45%) of the sub-title compound, which was used without further purification.

(b) tert-Butyl 5-[2-(4-cyanophenoxy)ethyl]hexahydropyrrolo[3,4-c]pyrrole-2(1H1)-carboxylate The sub-title compound was made in 91% yield according to the procedure described in Preparation E, step (c) above, using 4-(2-bromoethoxy)-benzonitrile (see step (a) above) in place of 3-(4-cyanoanilino)propyl 4-methylbenzenesulfonate.

(c) 4-(2-Hexahydropyrrolo[3,4-c]pyrrol-2(1H)-ylethoxy)benzonitrile

The title compound was made in 100% yield according to the procedure described in Preparation C, step (e) above, using tert-butyl 5-[2-(4-cyanophenoxy)ethyl]hexahydropyrrolo[3,4-c]pyrrole-2(1H)-carboxylate (see step (b) above) in place of tert-butyl 5-[4-(4-cyanophenyl)-4-(3,4-dimethoxyphenoxy)butyl]hexahydropyrrolo[3,4-c]pyrrole-2(1H)-carboxylate.

Preparation G

4-[(3-Hexahydropyrrolo[3,4-c]pyrrol-2(1H)-ylpropyl)sulfonyl]benzonitrile (a) 4-[(3-Bromopropyl)sulfanyl]benzonitrile A mixture of 4-cyanothiophenol (20.8 g, 154 mmol), 1,3-dibromopropane (155 g, 0.77 mol) and $K_2CO_3$ (21.3 g, 154 mmol) in MeCN (300 mL) was refluxed overnight. Filtration and evaporation of the solvent gave a brown oil that crystallised when treated with EtOH. The crystals were isolated by filtration to give the sub-title compound (24.5 g, 62%).

(b) 4-[(3-Bromopropyl)sulfonyl]benzonitrile

3-Chloroperoxybenzoic acid (44.9 g of 70%, 182 mmol) was added slowly to a cooled (0° C.) solution of 4-[(3-bromopropyl)sulfanyl]benzonitrile (from step (a) above; 23.4 g, 91 mmol) in DCM (250 mL). The mixture was then stirred at rt overnight, and the resulting precipitate filtered off. The filtrate was concentrated in vacuo to give a residue that was shown (by NMR analysis) to contain 25% sulfoxide in addition to the desired product. The residue was redissolved in DCM (250 mL), additional 3-chloroperoxybenzoic acid (5.6 g of 70%, 23 mmol) added, and the mixture stirred for 30 min. Dimethylsulfoxide (20 mmol) was added to destroy excess mCPBA before the DCM solution was washed with aqueous $NaHCO_3$, separated, dried and concentrated in vacuo. This gave the sub-title compound in 76% yield.

(c) tert-Butyl 5-{3-[(4-cyanophenyl)sulfonyl]propyl}hexahydropyrrolo[3,4-c]pyrrole-2(1H)-carboxylate The sub-title compound was prepared in 75% yield according to the procedure described in Preparation E, step (c) above, using 4-[(3-bromopropyl)sulfonyl]benzonitrile (see step (b) above) in place of 3-(4-cyanoanilino)propyl 4-methylbenzenesulfonate.

(d) 4-[(3-Hexahydropyrrolo[3,4-c]pyrrol-2(1H)-ylpropyl)sulfonyl]benzonitrile

The title compound was made in 100% yield according to the procedure described in Preparation C, step (e) above, using tert-butyl 5-{3-[(4-cyanophenyl)sulfonyl]propyl}hexahydropyrrolo[3,4-c]pyrrole-2(1H)-carboxylate (see step (c) above) in place of tert-butyl 5-[4-(4-cyanophenyl)-4-(3,4-dimethoxyphenoxy)butyl]hexahydropyrrolo[3,4-c]pyrrole-2(1H)-carboxylate.

Preparation H 4-(2-Hexahydropyrrolo[3,4-c]pyrrol-2(1H)-ylethoxy)isophthalonitrile (a) 4-(2-Bromoethoxy)isophthalonitrile The sub-title compound was prepared in 64% yield according to the procedure described in Preparation F, step (a) above, using 4-hydroxyisophthalonitrile in place of 4-cyanophenol.

(b) tert-Butyl 5-[2-(2,4-dicyanophenoxy)ethyl]hexahydropyrrolo[3,4-c]-pyrrole-2(1)-carboxylate The sub-title compound was made in 75% yield according to the procedure described in Preparation E, step (c) above, using 4-(2-bromoethoxy)-isophthalonitrile (see step (a) above) in place of 3-(4-cyanoanilino)propyl 4-methylbenzenesulfonate.

(c) 4-(2-Hexahydropyrrolo[3,4-c]pyrrol-2(1H)-ylethoxy)isophthalonitrile

The title compound was made in 80% yield according to the procedure described in Preparation C, step (e) above, above using tert-butyl 5-[2-(2,4-dicyanophenoxy)ethyl]hexahydropyrrolo[3,4-c]pyrrole-2(1H)-carboxylate (see step (b) above) in place of tert-butyl 5-[4-(4-cyanophenyl)-4-(3,4-di-methoxyphenoxy)butyl]hexahydropyrrolo[3,4-c]pyrrole-2(1H)-carboxylate.

Preparation I 2-(Acetyloxy)-1,1-dimethylethyl 1H-imidazole-1-carboxylate

A mixture of 2-hydroxy-2-methylpropyl acetate (3.35 g, 25.3 mmol) and 1,1'-carbonyldiimidazole (4.11 g, 25.3 mmol) in DCM was stirred for 8 h at rt. The mixture was then transferred to a closed vessel and heated to 100° C. overnight. The mixture was concentrated in vacuo before ether and water were added. The organic phase was separated, dried and concentrated in vacuo. The resulting residue was purified by chromatography on silica gel, eluting with THF:heptane (1:1), to give the title compound in 20% yield.

Preparation J

1-Cyano-1-methylethyl 1H-imidazole-1-carboxylate

A mixture of 1,1'-carbonyldiimidazole (5 g, 31 mmol) and 2-hydroxy-2-methylpropanenitrile (2.6 g, 31 mmol) in DCM was stirred at rt overnight. Water was added and the organic layer was separated, dried ($Na_2SO_4$) and concentrated in vacuo. The resulting residue was purified by chromatography on silica gel, eluting with ethyl acetate, to give 2.7 g (50%) of the title compound.

Preparation K

2-(4-Morpholinyl)ethyl 1H-imidazole-1-carboxylate

A mixture of 1,1'-carbonyldiimidazole (6.5 g, 40 mmol) and 2-(4-morpholinyl)-1-ethanol (5.0 g, 38.1 mmol) in DCM (200 mL) was stirred for 22 h at rt. Ether (400 mL) was added and the mixture was washed with water. The water layer was then extracted with DCM. The combined organic layers were dried over $Na_2SO_4$ and evaporated to give 6.0 g (70%) of the title compound.

Preparation L

2-(4-Pyridinyl)ethyl 1H-imidazole-1-carboxylate

The title compound was prepared in 100% yield according to the procedure described in Preparation K above, using 2-(4-pyridinyl)-1-ethanol in place of 2-(4-morpholinyl)-1-ethanol.

Preparation M

N-[2-(2-Methoxyethoxy)ethyl]-1H-imidazole-1-carboxamide

The title compound was prepared in 40% yield according to the procedure described in Preparation K above, using 2-(2-methoxyethoxy)ethylamine in place of 2-(4-morpholinyl)-1-ethanol.

Preparation N

2-(4-Acetyl-1-piperazinyl)ethyl 1H-imidazole-1-carboxylate (i) 1-[4-(2-Hydroxyethyl)-1-piperazinyl]-1-ethanone A solution of 2-(1-piperazinyl)-1-ethanol (6.5 g, 0.05 mol) in DCM (5 mL) was treated with acetic acid anhydride (5.1 g, 0.05 mol), added dropwise. During addition, the reaction temperature rose from 22 to 60° C. The reaction mixture was evaporated several times with toluene to yield 5.6 g (65%) of the sub-title compound.

(ii) 2-(4-Acetyl-1-piperazinyl)ethyl 1H-imidazole-1-carboxylate

A solution of 1,1'-carbonyldiimidazole (5 g, 31 mmol) in DCM (200 mL) was treated with a solution of 1-[4-(2-hydroxyethyl)-1-piperazinyl]-1-ethanone (see step (i) above; 5 g, 29 mmol) in DCM (50 mL). The reaction mixture was stirred at rt overnight before water was added. The layers were separated, and the organic layer was washed with water, dried and concentrated in vacuo to yield 7.4 g (96%) of the title compound.

Preparation O

1-[4-(3-Bromopropyl)-1-piperazinyl]-1-ethanone

A mixture of 1-(1-piperazinyl)-1-ethanone (6.7 g, 0.052 mol), dibromopropane (330 mL, excess) and $K_2CO_3$ (10.2 g, 0.079 mol) was stirred at rt for 4 h. The mixture was washed with 4×100 mL of water, and the organic phase (diluted with DCM) was acidified with aqueous hydrobromic acid (7 mL of 62% HBr dissolved in 150 mL of water). The organic layer was separated and washed with water (2×50 mL). The combined water layers were extracted with ether, neutralised (to pH 7) with 13 mL of 10 M NaOH, and, then extracted with DCM. The combined organic layers were dried and concentrated in vacuo to give 4.1 g (32%) of the title compound.

Preparation P

3-(Ethylsulfonyl)propyl 4-methylbenzenesulfonate (i) 3-(Ethylsulfonyl)-1-propanol A solution of 3-(ethylthio)-1-propanol (13 g, 0.11 mol) in acetic acid (40 mL) was treated with $H_2O_2$ (30% in water, 12.2 g, 0.11 mol), added dropwise. The mixture was stirred for 2 h at rt, before being concentrated in vacuo. NMR analysis showed that the resulting residue consisted of 40% of the desired product and 60% of the corresponding O-acetate. The acetate was hydrolysed by dissolving the reaction mixture in 200 mL of methanol and adding 3 g of NaOH (dissolved in a small amount of water). This mixture was stirred overnight at rt, then concentrated in vacuo. The resulting crude product was dissolved in DCM, and insoluble material was filtered off. The DCM was removed by evaporation to give 13.4 g (88%) of the sub-title compound.

(ii) 3-(Ethylsulfonyl)propyl 4-methylbenzenesulfonate

A mixture of 3-(ethylsulfonyl)-1-propanol (see step (i) above; 13.4 g, 88 mmol) and p-toluenesulfonyl chloride (16.8 g, 88 mmol) in DCM (150 mL) was treated with TEA (13.4 g, 132 mmol), added dropwise. The resulting mixture was stirred at rt for 3 h before being washed with aqueous ammonium chloride solution. The organic layer was then separated, dried and concentrated in vacuo. The product was crystallised from ether containing a small amount of DCM to yield 17.9 g (66%) of the title compound.

Synthesis of Compounds of Formula I

Example 1

General Description of Preparation of the Compounds in Example 2 Below:

One of the products of Preparations B to H above (0.25 mmol) was dissolved in $CHCl_3$ (0.5 mL). The appropriate electrophile (0.25 mmol) dissolved in $CH_3CN$ (2 mL) was added, followed by $K_2CO_3$ or triethylamine (0.375 mmol) (such bases are not needed when the electrophile is an isocyanate).

Reaction mixtures were stirred at between rt and 50° C. for 2 to 5 days. The reactions were monitored by LC-MS. When reactions were complete, the reaction mixtures were filtered, the solvents Were evaporated, and then the residues were dissolved in MeCN or CH₂Cl₂ (2 mL). The resulting solutions were added to ion-exchange solid phase extraction plugs (2 g CBA). The plugs were then eluted with DCM:MeCN (4:1, fraction 1), followed by DCM:MeOH:TEA (8.1:1, 4×2 mL). The fractions were evaporated. HPLC and MS analysis then enabled identification of the fraction(s) in which product resided.

Example 2

The following compounds were prepared from appropriate intermediates (such as those described hereinbefore) according to or by analogy with methods described herein (e.g. the procedure described above) and/or by standard solution phase chemistry techniques (mass spectra of the compounds, where recorded, are in brackets):

tert-butyl 5-[3-(4-cyanophenoxy)-2-hydroxypropyl]hexahydropyrrolo[3,4-c]pyrrole-2(1H)-carboxylate (m/z=388);

tert-butyl 5-[2-(4-cyanophenyl)ethyl]hexahydropyrrolo[3,4-c]pyrrole-2(1H)-carboxylate (m/z=342);

tert-butyl 5-[(2S)-3-(4-cyanophenoxy)-2-hydroxypropyl]hexahydropyrrolo-[3,4-c]pyrrole-2(1H)-carboxylate (m/z=388);

tert-butyl 5-{3-[(4-cyanophenyl)amino]propyl}hexahydropyrrolo[3,4-c]-pyrrole-2(1H)-carboxylate (m/z=371);

tert-butyl 5-[2-(4-cyanophenoxy)ethyl]hexahydropyrrolo[3,4-c]pyrrole-2(1H)-carboxylate (m/z=358);

5-[(2S)-3-(4-cyanophenoxy)-2-hydroxypropyl]-N-ethylhexahydropyrrolo-[3,4-c]pyrrole-2(1H)-carboxamide (m/z=359);

4-({(2R)-3-[5-[2-(3,4-dimethoxyphenyl)ethyl]hexahydropyrrolo[3,4-c]-pyrrol-2(1H)-yl]-2-hydroxypropyl}oxy)benzonitrile (m/z=452);

4-({3-[5-(butylsulfonyl)hexahydropyrrolo[3,4-c]pyrrol-2(1H)-yl]propyl}-amino)benzonitrile (m/z=391);

4-({3-[5-(3,3-dimethyl-2-oxobutyl)hexahydropyrrolo[3,4-c]pyrrol-2(1H)-yl]propyl}amino)benzonitrile (m/z=369);

4-({3-[5-[2-(3,4-dimethoxyphenyl)ethyl]hexahydropyrrolo[3,4-c]pyrrol-2(1H)-yl]propyl}amino)benzonitrile (m/z=435);

5-[2-(4-cyanophenoxy)ethyl]-N-ethylhexahydropyrrolo[3,4-c]pyrrole-2(1H)-carboxamide (m/z=329);

5-[4-(4-cyanophenyl)-4-(3,4-dimethoxyphenoxy)butyl]-N-ethylhexahydropyrrolo[3,4-c]pyrrole-2(1H)-carboxamide (m/z=493);

4-{2-[5-(butylsulfonyl)hexahydropyrrolo[3,4-c]pyrrol-2(1H)-yl]ethoxy}-benzonitrile (m/z=378);

4-[4-[5-(butylsulfonyl)hexahydropyrrolo[3,4-c]pyrrol-2(1H)-yl]-1-(3,4-dimethoxyphenoxy)butyl]benzonitrile (m/z=542);

4-{2-[5-(3,3-dimethyl-2-oxobutyl)hexahydropyrrolo[3,4-c]pyrrol-2(1H)-yl]ethoxy}benzonitrile (m/z=356);

4-{1-(3,4-dimethoxyphenoxy)-4-[5-(3,3-dimethyl-2-oxobutyl)hexahydropyrrolo[3,4-c]pyrrol-2(1H)-yl]butyl}benzonitrile (m/z=520);

4-{2-[5-[2-(3,4-dimethoxyphenyl)ethyl]hexahydropyrrolo[3,4-c]pyrrol-2(1H)-yl]ethoxy}benzonitrile (m/z=422);

4-{1-(3,4-dimethoxyphenoxy)-4-[5-[2-(3,4-dimethoxyphenyl)ethyl]hexahydropyrrolo[3,4-c]pyrrol-2(1H)-yl]butyl}benzonitrile (m/z=586);

4-({(2S)-3-[5-(butylsulfonyl)hexahydropyrrolo[3,4-c]pyrrol-2(1H)-yl]-2-hydroxypropyl}oxy)benzonitrile;

4-({(2S)-3-[5-(3,3-dimethyl-2-oxobutyl)hexahydropyrrolo[3,4-c]pyrrol-2(1H)-yl]-2-hydroxypropyl}oxy)benzonitrile (m/z=386);

5-{3-[(4-cyanophenyl)amino]propyl}-N-ethylhexahydropyrrolo[3,4-c]-pyrrole-2(1H)-carboxamide (m/z=342);

tert-butyl 5-[4-(4-cyanophenyl)-4-(3,4-dimethoxyphenoxy)butyl]hexahydropyrrolo[3,4-c]pyrrole-2(1H)-carboxylate (m/z=522);

tert-butyl 5-{3-[(4-cyanophenyl)sulfonyl]propyl}hexahydropyrrolo[3,4-c]-pyrrole-2(1H)-carboxylate (m/z=420);

5-[(2S)-3-(4-cyanophenoxy)-2-hydroxypropyl]-N-(3,5-dimethylisoxazol-4-yl)hexahydropyrrolo[3,4-c]pyrrole-2(1H)-carboxamide;

N-{[5-[(2S)-3-(4-cyanophenoxy)-2-hydroxypropyl]hexahydropyrrolo[3,4-c]pyrrol-2(1H)-yl]carbonyl}-4-methylbenzenesulfonamide;

5-[(2S)-3-(4-cyanophenoxy)-2-hydroxypropyl]-N-(4-methoxyphenyl)-hexahydropyrrolo[3,4-c]pyrrole-2(1H)-carboxamide;

5-[(2S)-3-(4-cyanophenoxy)-2-hydroxypropyl]-N-{4-[(trifluoromethyl)-thio]phenyl}hexahydropyrrolo[3,4-c]pyrrole-2(1H)-carboxamide (m/z=507);

5-[(2S)-3-(4-cyanophenoxy)-2-hydroxypropyl]-N-tetrahydro-2H-pyran-2-ylhexahydropyrrolo[3,4-c]pyrrole-2(1H)-carboxamide;

5-[(2S)-3-(4-cyanophenoxy)-2-hydroxypropyl]-N-(cyclopropylmethyl)-hexahydropyrrolo[3,4-c]pyrrole-2(1H)-carboxamide (m/z=385);

5-[(2S)-3-(4-cyanophenoxy)-2-hydroxypropyl]-N-isopropylhexahydropyrrolo[3,4-c]pyrrole-2(1H)-carboxamide;

5-[(2S)-3-(4-cyanophenoxy)-2-hydroxypropyl]-N-(3,4-difluorophenyl)-hexahydropyrrolo[3,4-c]pyrrole-2(1H)-carboxamide (m/z=443);

N-butyl-5-[(2S)-3-(4-cyanophenoxy)-2-hydroxypropyl]hexahydropyrrolo-[3,4-c]pyrrole-2(1H)-carboxamide (m/z=387);

5-{3-[(4-cyanophenyl)amino]propyl}-N-(3,5-dimethylisoxazol-4-yl)hexahydropyrrolo[3,4-c]pyrrole-2(1H)-carboxamide;

5-{3-[(4-cyanophenyl)amino]propyl}-N-(4-methoxyphenyl)hexahydropyrrolo[3,4-c]pyrrole-2(1H)-carboxamide;

5-{3-[(4-cyanophenyl)amino]propyl}-N-{4-[(trifluoromethyl)thio]phenyl}-hexahydropyrrolo[3,4-c]pyrrole-2(1H)-carboxamide (m/z=490);

5-{3-[(4-cyanophenyl)amino]propyl}-N-tetrahydro-2H-pyran-2-ylhexahydropyrrolo[3,4-c]pyrrole-2(1H)-carboxamide;

5-{3-[(4-cyanophenyl)amino]propyl}-N-(cyclopropylmethyl)hexahydropyrrolo[3,4-c]pyrrole-2(1H)-carboxamide (m/z=490);

5-{3-[(4-cyanophenyl)amino]propyl}-N-isopropylhexahydropyrrolo[3,4-c]-pyrrole-2(1H)-carboxamide (m/z=356);

5-{3-[(4-cyanophenyl)amino]propyl}-N-(3,4-difluorophenyl)hexahydropyrrolo[3,4-c]pyrrole-2(1H)-carboxamide (m/z=426);

N-butyl-5-{3-[(4-cyanophenyl)amino]propyl}hexahydropyrrolo[3,4-c]-pyrrole-2(1H)-carboxamide;

5-[2-(4-cyanophenoxy)ethyl]-N-(3,5-dimethylisoxazol-4-yl)hexahydropyrrolo[3,4-c]pyrrole-2(1H)-carboxamide;

N-{[5-[2-(4-cyanophenoxy)ethyl]hexahydropyrrolo[3,4-c]pyrrol-2(1H)-yl]carbonyl}-4-methylbenzenesulfonamide;

5-[2-(4-cyanophenoxy)ethyl]-N-(4-methoxyphenyl)hexahydropyrrolo[3,4-c]pyrrole-2(1H)-carboxamide (m/z=407);

5-[2-(4-cyanophenoxy)ethyl]-N-{4-[(trifluoromethyl)thio]phenyl}hexahydropyrrolo[3,4-c]pyrrole-2(1H)-carboxamide (m/z=477);

5-[2-(4-cyanophenoxy)ethyl]-N-tetrahydro-2H-pyran-2-yl-hexahydropyrrolo[3,4-c]pyrrole-2(1H)-carboxamide;

5-[2-(4-cyanophenoxy)ethyl]-N-(cyclopropylmethyl) hexahydropyrrolo[3,4-c]pyrrole-2(1H)-carboxamide (m/z=355);

5-[2-(4-cyanophenoxy)ethyl]-N-isopropylhexahydropyrrolo[3,4-c]pyrrole-2(1H)-carboxamide (m/z=343);

5-[2-(4-cyanophenoxy)ethyl]-N-(3,4-difluorophenyl) hexahydropyrrolo[3,4-c]pyrrole-2(1H)-carboxamide (m/z=413);

N-butyl-5-[2-(4-cyanophenoxy)ethyl]hexahydropyrrolo[3,4-c]pyrrole-2(1H)-carboxamide (m/z=357);

5-{3-[(4-cyanophenyl)sulfonyl]propyl}-N-ethylhexahydro-pyrrolo[3,4-c]-pyrrole-2(1H)-carboxamide;

5-{3-[(4-cyanophenyl)sulfonyl]propyl}-N-(3,5-dimethyl-isoxazol-4-yl)hexahydropyrrolo[3,4-c]pyrrole-2(1H)-carboxamide;

N-{[5-{3-[(4-cyanophenyl)sulfonyl]propyl}hexahydropyrrolo[3,4-c]pyrrol-2(1H-yl]carbonyl}-4-methylbenzenesulfonamide;

5-{3-[(4-cyanophenyl)sulfonyl]propyl}-N-(4-methoxyphenyl)hexahydropyrrolo[3,4-c]pyrrole-2(1H)-carboxamide;

5-{3-[(4-cyanophenyl)sulfonyl]propyl}-N-{4-[(trifluoromethyl)thio]-phenyl}hexahydropyrrolo[3,4-c]pyrrole-2(1H)-carboxamide (m/z=539);

5-{3-[(4-cyanophenyl)sulfonyl]propyl}-N-tetrahydro-2H-pyran-2-ylhexahydropyrrolo[3,4-c]pyrrole-2(1H)-carboxamide;

5-{3-[(4-cyanophenyl)sulfonyl]propyl}-N-(cyclopropylmethyl)hexahydropyrrolo[3,4-c]pyrrole-2(1H)-carboxamide (m/z=417);

5-{3-[(4-cyanophenyl)sulfonyl]propyl}-N-isopropyl-hexahydropyrrolo[3,4-c]pyrrole-2(1H)-carboxamide;

5-{3-[(4-cyanophenyl)sulfonyl]propyl}-N-(3,4-difluorophenyl)hexahydropyrrolo[3,4-c]pyrrole-2(1H)-carboxamide (m/z=475);

N-butyl-5-{3-[(4-cyanophenyl)sulfonyl]propyl}hexahydropyrrolo[3,4-c]-pyrrole-2(1H)-carboxamide (m/z=419);

5-[(2S)-2-amino-3-(4-cyanophenoxy)propyl]-N-ethyl-hexahydropyrrolo[3,4-c]pyrrole-2(1H)-carboxamide (m/z=358);

5-[(2S)-2-amino-3-(4-cyanophenoxy)propyl]-N-(3,5-dimethylisoxazol-4-yl)hexahydropyrrolo[3,4-c]pyrrole-2(1H)-carboxamide;

N-{[5-[(2S)-2-amino-3-(4-cyanophenoxy)propyl]hexahydropyrrolo[3,4-c]-pyrrol-2(1H)-yl]carbonyl}-4-methylbenzenesulfonamide;

5-[(2S)-2-amino-3-(4-cyanophenoxy)propyl]-N-(4-methoxyphenyl)hexahydropyrrolo[3,4-c]pyrrole-2(1H)-carboxamide (m/z=436);

5-[(2S)-2-amino-3-(4-cyanophenoxy)propyl]-N-{4-[(trifluoromethyl)thio]-phenyl}hexahydropyrrolo[3,4-c]pyrrole-2(1H)-carboxamide (m/z=506);

5-[(2S)-2-amino-3-(4-cyanophenoxy)propyl]-N-(cyclopropylmethyl)hexahydropyrrolo[3,4-c]pyrrole-2(1H)-carboxamide (m/z=384);

5-[(2S)-2-amino-3-(4-cyanophenoxy)propyl]-N-isopropyl-hexahydropyrrolo-[3,4-c]pyrrole-2(1H)-carboxamide (m/z=372);

5-[(2S)-2-amino-3-(4-cyanophenoxy)propyl]-N-(3,4-difluorophenyl)hexahydropyrrolo[3,4-c]pyrrole-2(1H)-carboxamide (m/z=442);

5-[(2S)-2-amino-3-(4-cyanophenoxy)propyl]-N-butyl-hexahydropyrrolo[3,4-c]pyrrole-2(1H)-carboxamide (m/z 386);

5-[2-(2,4-dicyanophenoxy)ethyl]-N-ethylhexahydropyrrolo[3,4-c]pyrrole-2(1H)-carboxamide;

5-[2-(2,4-dicyanophenoxy)ethyl]-N-(3,5-dimethylisoxazol-4-yl)hexahydropyrrolo[3,4-c]pyrrole-2(1H)-carboxamide;

N-{[5-[2-(2,4-dicyanophenoxy)ethyl]hexahydropyrrolo[3,4-c]pyrrol-2(1H)-yl]carbonyl}-4-methylbenzenesulfonamide;

5-[2-(2,4-dicyanophenoxy)ethyl]-N-(4-methoxyphenyl) hexahydropyrrolo-[3,4-c]pyrrole-2(1H)-carboxamide (m/z=432);

5-[2-(2,4-dicyanophenoxy)ethyl]-N-{4-[(trifluoromethyl)thio]phenyl}hexahydropyrrolo[3,4-c]pyrrole-2(1H)-carboxamide (m/z=502);

5-[2-(2,4-dicyanophenoxy)ethyl]-N-tetrahydro-2H-pyran-2-ylhexahydropyrrolo[3,4-c]pyrrole-2(1H)-carboxamide (m/z=410);

N-(cyclopropylmethyl)-5-[2-(2,4-dicyanophenoxy)ethyl] hexahydropyrrolo-[3,4-c]pyrrole-2(1H)-carboxamide (m/z=380);

5-[2-(2,4-dicyanophenoxy)ethyl]-N-isopropylhexahydropyrrolo[3,4-c]-pyrrole-2(1H)-carboxamide (m/z=368);

5-[2-(2,4-dicyanophenoxy)ethyl]-N-(3,4-difluorophenyl) hexahydropyrrolo-[3,4-c]pyrrole-2(1H)-carboxamide;

N-butyl-5-[2-(2,4-dicyanophenoxy)ethyl]hexahydropyrrolo[3,4-c]pyrrole-2(1H)-carboxamide (m/z=382);

ethyl 5-[(2S)-3-(4-cyanophenoxy)-2-hydroxypropyl] hexahydropyrrolo[3,4-c]pyrrole-2(1H)-carboxylate (m/z=360);

2-hydroxy-1,1-dimethylethyl 5-[(2S)-3-(4-cyanophenoxy)-2-hydroxy-propyl]hexahydropyrrolo[3,4-c]pyrrole-2(1H)-carboxylate (m/z=404);

1-cyano-1-methylethyl 5-[(2S)-3-(4-cyanophenoxy)-2-hydroxypropyl]hexahydropyrrolo[3,4-c]pyrrole-2(1H)-carboxylate;

but-2-ynyl 5-[(2S)-3-(4-cyanophenoxy)-2-hydroxypropyl] hexahydropyrrolo[3,4-c]pyrrole-2(1H)-carboxylate (m/z=384);

2-methoxyethyl 5-[(2S)-3-(4-cyanophenoxy)-2-hydroxypropyl]hexahydropyrrolo[3,4-c]pyrrole-2(1H)-carboxylate;

3-(methylsulfonyl)propyl 5-[(2S)-3-(4-cyanophenoxy)-2-hydroxypropyl]-hexahydropyrrolo[3,4-c]pyrrole-2(1H)-carboxylate;

2-morpholin-4-ylethyl 5-[(2S)-3-(4-cyanophenoxy)-2-hydroxypropyl]hexahydropyrrolo[3,4-c]pyrrole-2(1H)-carboxylate;

2-pyridin-4-ylethyl 5-[(2S)-3-(4-cyanophenoxy)-2-hydroxypropyl]hexahydropyrrolo[3,4-c]pyrrole-2(1H)-carboxylate (m/z=437);

2-(4-acetylpiperazin-1-yl)ethyl 5-[(2S)-3-(4-cyanophenoxy)-2-hydroxypropyl]hexahydropyrrolo[3,4-c]pyrrole-2(1H)-carboxylate;

5-[(2S)-3-(4-cyanophenoxy)-2-hydroxypropyl]-N-[2-(2-methoxyethoxy)-ethyl]hexahydropyrrolo[3,4-c]pyrrole-2(1H)-carboxamide;

ethyl 5-{3-[(4-cyanophenyl)amino] propyl}hexahydropyrrolo[3,4-c]pyrrole-2(1H)-carboxylate (m/z 343);

2-hydroxy-1,1-dimethylethyl 5-{3-[(4-cyanophenyl)amino] propyl}hexahydropyrrolo[3,4-c]pyrrole-2(1H)-carboxylate (m/z=387);

1-cyano-1-methylethyl 5-{3-[(4-cyanophenyl)amino] propyl}hexahydropyrrolo[3,4-c]pyrrole-2(1H)-carboxylate (m/z=382);

but-2-ynyl 5-{3-[(4-cyanophenyl)amino]propyl}hexahydropyrrolo[3,4-c]-pyrrole-2(1H)-carboxylate (m/z=367);

2-methoxyethyl 5-{3-[(4-cyanophenyl)amino]propyl}hexahydropyrrolo-[3,4-c]pyrrole-2(1H)-carboxylate (m/z=373); 3-(methylsulfonyl)propyl 5-{3-[(4-cyanophenyl)amino]propyl}hexahydropyrrolo[3,4-c]pyrrole-2(1H)-carboxylate;

2-morpholin-4-ylethyl 5-{3-[(4-cyanophenyl)amino]propyl}hexahydropyrrolo[3,4-c]pyrrole-2(1H)-carboxylate;

2-pyridin-4-ylethyl 5-{3-[(4-cyanophenyl)amino]propyl}hexahydropyrrolo-[3,4-c]pyrrole-2(1H)-carboxylate (m/z=420);

2-(4-acetylpiperazin-1-yl)ethyl 5-{3-[(4-cyanophenyl)amino]propyl}hexahydropyrrolo[3,4-c]pyrrole-2(1H)-carboxylate;

5-{3-[(4-cyanophenyl)amino]propyl}-N-[2-(2-methoxyethoxy)ethyl]hexahydropyrrolo[3,4-c]pyrrole-2(1H)-carboxamide; ethyl 5-[2-(4-cyanophenoxy)ethyl]hexahydropyrrolo[3,4-c]pyrrole-2(1H)-carboxylate (m/z=330);

2-hydroxy-1,1-dimethylethyl 5-[2-(4-cyanophenoxy)ethyl]hexahydropyrrolo[3,4-c]pyrrole-2(1H)-carboxylate (m/z=374);

1-cyano-1-methylethyl 5-[2-(4-cyanophenoxy)ethyl]hexahydropyrrolo[3,4-c]pyrrole-2(1H)-carboxylate (m/z=369);

but-2-ynyl 5-[2-(4-cyanophenoxy)ethyl]hexahydropyrrolo[3,4-c]pyrrole-2(1H)-carboxylate (m/z=354);

2-methoxyethyl 5-[2-(4-cyanophenoxy)ethyl]hexahydropyrrolo[3,4-c]-pyrrole-2(1H)-carboxylate (m/z=359);

3-(methylsulfonyl)propyl 5-[2-(4-cyanophenoxy)ethyl]hexahydropyrrolo-[3,4-c]-pyrrole-2(1H)-carboxylate (m/z=422);

2-morpholin-4-ylethyl 5-[2-(4-cyanophenoxy)ethyl]hexahydropyrrolo[3,4-c]pyrrole-2(1H)-carboxylate (m/z=415);

2-pyridin-4-ylethyl 5-[2-(4-cyanophenoxy)ethyl]hexahydropyrrolo[3,4-c]-pyrrole-2(1)-carboxylate (m/z=407);

2-(4-acetylpiperazin-1-yl)ethyl 5-[2-(4-cyanophenoxy)ethyl]hexahydropyrrolo[3,4-c]pyrrole-2(1H)-carboxylate (m/z=456);

5-[2-(4-cyanophenoxy)ethyl]-N-[2-(2-methoxyethoxy)ethyl]hexahydropyrrolo[3,4-c]pyrrole-2(1H)-carboxamide (m/z=403);

ethyl 5-{3-[(4-cyanophenyl)sulfonyl]propyl}hexahydropyrrolo[3,4-c]pyrrole-2(1H)-carboxylate (m/z=392);

2-hydroxy-1,1-dimethylethyl 5-{3-[(4-cyanophenyl)sulfonyl]propyl}hexahydropyrrolo[3,4-c]pyrrole-2(1H)-carboxylate (m/z=436);

1-cyano-1-methylethyl 5-{3-[(4-cyanophenyl)sulfonyl]propyl}hexahydropyrrolo[3,4-c]pyrrole-2(1H)-carboxylate (m/z=431);

but-2-ynyl 5-{3-[(4-cyanophenyl)sulfonyl]propyl}hexahydropyrrolo[3,4-c]pyrrole-2(1H)-carboxylate (m/z 416);

2-methoxyethyl 5-{3-[(4-cyanophenyl)sulfonyl]propyl}hexahydropyrrolo-[3,4-c]pyrrole-2(1H)-carboxylate (m/z=422);

3-(methylsulfonyl)propyl 5-{3-[(4-cyanophenyl)sulfonyl]propyl}hexahydropyrrolo[3,4-c]pyrrole-2(1H)-carboxylate (m/z=484);

2-morpholin-4-ylethyl 5-{3-[(4-cyanophenyl)sulfonyl]propyl}hexahydropyrrolo[3,4-c]pyrrole-2(1H)-carboxylate (m/z=477);

2-pyridin-4-ylethyl 5-{3-[(4-cyanophenyl)sulfonyl]propyl}hexahydropyrrolo[3,4-c]pyrrole-2(1H)-carboxylate (m/z=469);

2-(4-acetylpiperazin-1-yl)ethyl 5-{3-[(4-cyanophenyl)sulfonyl]propyl}-hexahydropyrrolo[3,4-c]pyrrole-2(1)-carboxylate (m/z=518);

5-{3-[(4-cyanophenyl)sulfonyl]propyl}-N-[2-(2-methoxyethoxy)ethyl]-hexahydropyrrolo[3,4-c]pyrrole-2(1H)-carboxamide (m/z=465);

4-({(2S)-3-[5-(cyclopropylmethyl)hexahydropyrrolo[3,4-c]pyrrol-2(1H)-yl]-2-hydroxypropyl}oxy)benzonitrile (m/z=342);

4-({(2S)-3-[5-[3-(4-acetylpiperazin-1-yl)propyl]hexahydropyrrolo[3,4-c]-pyrrol-2(1H)-yl]-2-hydroxypropyl}oxy)benzonitrile (m/z=456);

2-[5-[(2S)-3-(4-cyanophenoxy)-2-hydroxypropyl]hexahydropyrrolo[3,4-c]-pyrrol-2(1H)-yl]-N-isopropylacetamide (m/z=387);

4-({(2S)-3-[5-[3-(ethylsulfonyl)propyl]hexahydropyrrolo[3,4-c]pyrrol-2(1H)-yl]-2-hydroxypropyl}oxy)benzonitrile (m/z=422);

4-({(2S)-2-hydroxy-3-[5-[2-(2-methoxyethoxy)ethyl]hexahydropyrrolo[3,4-c]pyrrol-2(1H)-yl]propyl}oxy)benzonitrile (m/z=390);

4-({3-[5-(cyclopropylmethyl)hexahydropyrrolo[3,4-c]pyrrol-2(1H)-yl]-propyl}amino)benzonitrile (m/z=325);

4-({3-[5-[3-(4-acetylpiperazin-1-yl)propyl]hexahydropyrrolo[3,4-c]pyrrol-2(1H)-yl]propyl}amino)benzonitrile (m/z=439);

2-[5-{3-[(4-cyanophenyl)amino]propyl}hexahydropyrrolo[3,4-c]pyrrol-2(1H)-yl]-N-isopropylacetamide (m/z=370);

4-({3-[5-[3-(ethylsulfonyl)propyl]hexahydropyrrolo[3,4-c]pyrrol-2(1H)-yl]-propyl}amino)benzonitrile (m/z=404 (M-1));

4-({3-[5-[2-(2-methoxyethoxy)ethyl]hexahydropyrrolo[3,4-c]pyrrol-2(1H)-yl]propyl}amino)benzonitrile (m/z=373);

4-{2-[5-[3-(4-acetylpiperazin-1-yl)propyl]hexahydropyrrolo[3,4-c]pyrrol-2(1H)-yl]ethoxy}benzonitrile (m/z=426);

2-[5-[2-(4-cyanophenoxy)ethyl]hexahydropyrrolo[3,4-c]pyrrol-2(1H)-yl]-N-isopropylacetamide (m/z=357);

4-{2-[5-[3-(ethylsulfonyl)propyl]hexahydropyrrolo[3,4-c]pyrrol-2(1H)-yl]-ethoxy}benzonitrile (m/z=392);

4-{2-[5-[2-(2-methoxyethoxy)ethyl]hexahydropyrrolo[3,4-c]pyrrol-2(1H)-yl]ethoxy}benzonitrile (m/z=360);

4-{2-[5-(4-fluorobenzyl)hexahydropyrrolo[3,4-c]pyrrol-2(1H)-yl]ethoxy}-benzonitrile (m/z=366);

4-({3-[5-(3,3-dimethyl-2-oxobutyl)hexahydropyrrolo[3,4-c]pyrrol-2(1H)-yl]propyl}sulfonyl)benzonitrile (m/z=418);

4-({3-[5-(cyclopropylmethyl)hexahydropyrrolo[3,4-c]pyrrol-2(1H)-yl]-propyl}sulfonyl)benzonitrile (m/z=375);

4-({3-[5-[3-(4-acetylpiperazin-1-yl)propyl]hexahydropyrrolo[3,4-c]pyrrol-2(1H)-yl]propyl}sulfonyl)benzonitrile (m/z=488);

2-[5-{3-[(4-cyanophenyl)sulfonyl]propyl}hexahydropyrrolo[3,4-c]pyrrol-2(1H)-yl]-N-isopropylacetamide (m/z=419);

4-({3-[5-[3-(ethylsulfonyl)propyl]hexahydropyrrolo[3,4-c]pyrrol-2(1H)-yl]-propyl}sulfonyl)benzonitrile (m/z=454);

4-({3-[5-[2-(2-methoxyethoxy)ethyl]hexahydropyrrolo[3,4-c]pyrrol-2(1H)-yl]propyl}sulfonyl)benzonitrile (m/z=422);

4-({3-[5-[2-(4-methoxyphenyl)-2-oxoethyl]hexahydropyrrolo[3,4-c]pyrrol-2(1H)-yl]propyl}sulfonyl)benzonitrile (m/z=468);
4-({(2S)-2-amino-3-[5-(3,3-dimethyl-2-oxobutyl)hexahydropyrrolo[3,4-c]-pyrrol-2(1H)-yl]propyl}oxy)benzonitrile (m/z=385);
4-({(2S)-2-amino-3-[5-(cyclopropylmethyl)hexahydropyrrolo[3,4-c]pyrrol-2(1H)-yl]propyl}oxy)benzonitrile (m/z=341);
4-({(2S)-3-[5-[3-(4-acetylpiperazin-1-yl)propyl]hexahydropyrrolo[3,4-c]-pyrrol-2(1H)-yl]-2-aminopropyl}oxy)benzonitrile (m/z=455);
2-5-[(2S)-2-amino-3-(4-cyanophenoxy)propyl]hexahydropyrrolo[3,4-c]-pyrrol-2(1H)-yl]-N-isopropylacetamide (m/z=386);
4-({(2S)-2-amino-3-[5-[3-(ethylsulfonyl)propyl]hexahydropyrrolo[3,4-c]-pyrrol-2(1H)-yl]propyl}oxy)benzonitrile (m/z=421);
4-({(2S)-2-amino-3-[5-[2-(2-methoxyethoxy)ethyl]hexahydropyrrolo[3,4-c]pyrrol-2(1H)-yl]propyl}oxy)benzonitrile (m/z=389);
4-({(2S)-2-amino-3-[5-(4-fluorobenzyl)hexahydropyrrolo[3,4-c]pyrrol-2(1H)-yl]propyl}oxy)benzonitrile (m/z=395);
4-{2-[5-(3,3-dimethyl-2-oxobutyl)hexahydropyrrolo[3,4-c]pyrrol-2(1H)-yl]ethoxy}isophthalonitrile (m/z=381);
4-{2-[5-(cyclopropylmethyl)hexahydropyrrolo[3,4-c]pyrrol-2(1H)-yl]-ethoxy}isophthalonitrile (m/z=337);
4-{2-[5-[3-(4-acetylpiperazin-1-yl)propyl]hexahydropyrrolo[3,4-c]-pyrrol-2(1H)-yl]ethoxy}isophthalonitrile (m/z=451);
2-[5-[2-(2,4-dicyanophenoxy)ethyl]hexahydropyrrolo[3,4-c]pyrrol-2(1H)-yl]-N-isopropylacetamide (m/z=382);
4-{2-[5-[3-(ethylsulfonyl)propyl]hexahydropyrrolo[3,4-c]pyrrol-2(1H)-yl]-ethoxy}isophthalonitrile (m/z=417);
4-{2-[5-[2-(2-methoxyethoxy)ethyl]hexahydropyrrolo[3,4-c]pyrrol-2(1H)-yl]ethoxy}isophthalonitrile (m/z=385);
4-{2-[5-(4-fluorobenzyl)hexahydropyrrolo[3,4-c]pyrrol-2(1H)-yl]ethoxy}-isophthalonitrile (m/z=391);
4-{2-[5-[2-(4-methoxyphenyl)-2-oxoethyl]hexahydropyrrolo[3,4-c]pyrrol-2(1H)-yl]ethoxy}isophthalonitrile (m/z=431);
tert-butyl 5-[2-(2,4-dicyanophenoxy)ethyl]hexahydropyrrolo[3,4-c]pyrrole-2(1H)-carboxylate;
3,3-dimethyl-2-oxobutyl 5-[(2S)-3-(4-cyanophenoxy)-2-hydroxypropyl]-hexahydropyrrolo[3,4-c]pyrrole-2(1H)-carboxylate;
5-{3-[(4-cyanophenyl)amino]propyl}-N-methylhexahydropyrrolo[3,4-c]-pyrrole-2(1H)-carboxamide;
5-{3-[(4-cyanophenyl)amino]propyl}-N-propylhexahydropyrrolo[3,4-c]-pyrrole-2(1H)-carboxamide;
N-allyl-5-{3-[(4-cyanophenyl)amino]propyl}hexahydropyrrolo[3,4-c]-pyrrole-2(1H)-carboxamide; and
N-(tert-butyl)-5-{3-[(4-cyanophenyl)amino]propyl}hexahydropyrrolo[3,4-c]pyrrole-2(1H)-carboxamide.

Example 3

Compounds of the above Examples were tested in Test A above and were found to exhibit $D_{10}$ values of at least 5.5

Example 4

Compounds of the above Examples were tested in Test B above and were found to have pIC50 values of at least 4.5.

ABBREVIATIONS

Ac=acetyl
API=atmospheric pressure ionisation (in relation to MS)
aq.=aqueous
br=broad (in relation to NMR)
Bt=benzotriazole
t-BuOH=tert-butanol
CI=chemical ionisation (in relation to MS)
mCPBA=meta-chloroperoxybenzoic acid
d=doublet (in relation to NMR)
DBU=diazabicyclo[5.4.0]undec-7-ene
DCM=dichloromethane
dd=doublet of doublets (in relation to NMR)
DMAP=4-dimethylaminopyridine
DMF=N,N-dimethylformamide
DMSO dimethylsulfoxide
EDC=1-[3-(dimethylamino)propyl]-3-ethylcarbodiimide
Et=ethyl
EtOAc=ethyl acetate
eq.=equivalents
ES=electrospray (in relation to MS)
FAB=fast atom bombardment (in relation to MS)
h=hour(s)
HCl=hydrochloric acid
HEPES 4-(2-hydroxyethyl)-1-piperazineethanesulfonic acid
HPLC=high performance liquid chromatography
IMS=industrial methylated spirits
IPA=iso-propyl alcohol (propan-2-ol)
m=multiplet (in relation to NMR)
Me=methyl
MeCN=acetonitrile
MeOH=methanol
min.=minute(s)
m.p.=melting point
MS=mass spectroscopy
NADPH=nicotinamide adenine dinucleotide phosphate, reduced form
OAc=acetate
Pd/C=palladium on carbon
q=quartet (in relation to NMR)
rt=room temperature
s=singlet (in relation to NMR)
t=triplet (in relation to NMR)
TEA=triethylamine
THF=tetrahydrofuran
tlc=thin layer chromatography Prefixes n-, s-, i-, t- and tert- have their usual meanings: normal, secondary, iso, and tertiary.

The invention claimed is:
1. A compound of formula I,

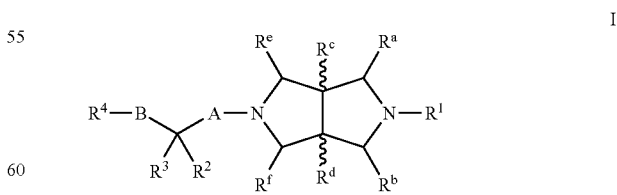

I wherein
the wavy lines represent optional relative cis- or trans-stereochemistry;
$R^1$ represents $C_{1-12}$ alkyl (optionally substituted and/or terminated by one or more groups selected from halo, cyano, nitro, aryl, —C(O)R$^{5a}$, —OR$^{5b}$, —N(R$^6$)R$^{5c}$, —C(O)XR$^7$, —C(O)N(R$^8$) R$^{5d}$ and —S(O)$_2$R$^9$), —C(O)R$^{5a}$, —C(O)XR$^7$, or —S(O)$_2$R$^9$;

R$^{5a}$ to R$^{5d}$ independently represent, at each occurrence when used herein, H, C$_{1-6}$ alkyl (optionally substituted and/or terminated by one or more substituents selected from —OH, C$_{1-6}$ alkoxy, halo, cyano, nitro, aryl, and —NHC(O)R$^{10}$), or aryl, or R$^{5d}$, together with R$^8$, represents C$_{3-6}$ alkylene (which alkylene group is optionally interrupted by an O atom and/or is optionally substituted by one or more C$_{1-3}$ alkyl groups);

R$^{10}$ represents H, C$_{1-4}$ alkyl (optionally substituted and/or terminated by one or more substituents selected from halo, cyano, aryl and —NHC(O)R$^{11}$) or aryl;

R$^{11}$ represents H, C$_{1-4}$ alkyl or aryl;

R$^6$ represents H, C$_{1-6}$ alkyl (optionally substituted and/or terminated by one or more substituents selected from —OH, halo, cyano, nitro and aryl), aryl, —C(O)R$^{12a}$, —C(O)OR$^{12b}$ or —C(O)N(H)R$^{12c}$;

R$^{12a}$, R$^{12b}$ and R$^{12c}$ represent C$_{1-6}$ alkyl (optionally substituted and/or terminated by one or more substituents selected from —OH, halo, cyano, nitro and aryl) or aryl, or R$^{12a}$ and R$^{12c}$ represent H;

X represents O or S;

R$^7$ represents, at each occurrence when used herein, aryl or C$_{1-2}$ alkyl (which alkyl group is optionally substituted and/or terminated by one or more substituents selected from —OH, halo, cyano, nitro, aryl, C$_{1-6}$ alkoxy, —SO$_2$R$^{13a}$, and —C(O)R$^{13b}$);

R$^{13a}$ and R$^{13b}$ independently represent C$_{1-6}$ alkyl or aryl;

R$^8$ represents, at each occurrence when used herein, H, C$_{1-12}$ alkyl, C$_{1-6}$ alkoxy (which latter two groups are optionally substituted and/or terminated by one or more substituents selected from —OH, halo, cyano, nitro, C$_{1-4}$ alkyl and C$_{1-4}$ alkoxy), —D-aryl, —D-aryloxy, —D—N(H)C(O)R$^{14a}$, —D—S(O)$_2$R$^{15a}$, —D—C(O)R$^{14b}$, —D—C(O)OR$^{15b}$, —D—C(O)N(R$^{14c}$)R$^{14d}$, or R$^8$, together with R$^{5d}$, represents C$_{3-6}$ alkylene (which alkylene group is optionally interrupted by an O atom and/or is optionally substituted by one or more C$_{1-3}$ alkyl groups);

R$^{14a}$ to R$^{14d}$ independently represent H, C$_{1-6}$ alkyl (optionally substituted and/or terminated by one or more substituents selected from —OH, halo, cyano, nitro and aryl), aryl, or R$^{14c}$ and R$^{14d}$ together represent C$_{3-6}$ alkylene;

R$^{15a}$ and R$^{15b}$ independently represent C$_{1-6}$ alkyl (optionally substituted and/or terminated by one or more substituents selected from —OH, halo, cyano, nitro and aryl) or aryl;

D represents a direct bond or C$_{1-6}$ alkylene;

R$^9$ represents, at each occurrence when used herein, C$_{1-6}$ alkyl (optionally substituted and/or terminated by one or more substituents selected from —OH, halo, cyano, nitro and aryl), or aryl;

R$^2$ represents H, halo, C$_{1-6}$ alkyl, —E—OR$^{16}$, —E—N(R$^{17}$)R$^{18}$ or, together with R$^3$, represents =O;

R$^3$ represents H, C$_{1-6}$ alkyl or, together with R$^2$ represents =O;

R$^{16}$ represents H, C$_{1-6}$ alkyl, —E-aryl, —C(O)R$^{19a}$, —C(O)OR$^{19b}$ or —C(O)N(R$^{20a}$)R$^{20b}$;

R$^{17}$ represents H, C$_{1-6}$ alkyl, —E-aryl, —C(O)R$^{19a}$, —C(O)OR$^{19b}$, —S(O)$_2$R$^{19c}$, —[C(O)]$_p$N(R$^{20a}$)R$^{20b}$ or —C(NH)NH$_2$;

R$^{18}$ represents H, C$_{1-6}$ alkyl, —E-aryl or —C(O)R$^{19d}$;

R$^{19a}$ to R$^{19d}$ independently represent, at each occurrence when used herein, C$_{1-6}$ alkyl (optionally substituted and/or terminated by one or more substituents selected from halo), aryl, or R$^{19a}$ and R$^{19d}$ independently represent H;

R$^{20a}$ and R$^{20b}$ independently represent, at each occurrence when used herein, H or C$_{1-6}$ alkyl (optionally substituted and/or terminated by one or more substituents selected from halo, and aryl), aryl, or together represent C$_{3-6}$ alkylene, optionally interrupted by an O atom;

E represents, at each occurrence when used herein, a direct bond or C$_{1-4}$ alkylene;

p represents 1 or 2;

A represents —G—, or —J—O— (in which O is attached to the carbon atom bearing R$^2$ and R$^3$);

B represents —Z—, —Z—S(O)$_n$—, —Z—O— (in which latter two groups, Z is attached to the carbon atom bearing R$^2$ and R$^3$);

G represents C$_{1-6}$ alkylene;

J represents C$_{2-6}$ alkylene;

Z represents a direct bond or C$_{1-4}$ alkylene;

R$^4$ represents aryl optionally substituted by one or more substituents selected from —OH, cyano, halo, nitro, C$_{1-6}$ alkyl (optionally terminated by —N(H)C(O)OR$^{23a}$), C$_{1-6}$ alkoxy, aryl, —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$; —N(R$^{24m}$)S(O)$_2$R$^{23b}$, —S(O)$_n$R$^{23c}$, —OS(O)$_2$R$^{23d}$, or —S(O)$_2$N(R$^{24n}$)R$^{24p}$;

R$^{23a}$ to R$^{23d}$ independently represent, at each occurrence when used herein, C$_{1-6}$ alkyl;

R$^{24a}$ to R$^{24p}$ independently represent, at each occurrence when used herein, H or C$_{1-6}$ alkyl;

n represents, at each occurrence, 0, 1 or 2; and

R$^a$ to R$^f$ independently represent H or C$_{1-4}$ alkyl;

wherein each aryl and aryloxy group, unless otherwise specified, is optionally substituted;

or a pharmaceutically acceptable derivative thereof;

provided that:
(a) when R$^3$ represents H or C$_{1-4}$ alkyl; and
  A represents —J—O—;
  then B does not represent —S(O)$_n$—, or —O—;
(b) when R$^2$ represents —E—OR$^{16}$ or —E—N(R$^{17}$)R$^{18}$ in which E represents a direct bond, then:
  (i) A does not represent —J—O—; and
  (ii) B does not represent —S(O)$_n$—, or —O—;
(c) the compound is not:
  3,7-bis(1-phenylehyl)-3,7-diazabicyclo[3.3.0]octane;
  2-{4-(7-benzyl-3,7-diazabicyclo[3.3.0]octan-3-yl)butyl}-1,2-benzisothiazol-3-one-1,1-dioxide;
  3-methyl-7-benzyl-3,7-diazabicyclo[3.3.0]octane;
  3-cyclohexyl-7-benzyl-3,7-diazabicyclo[3.3.0]octane;
  3-(thiazol-2-yl)-7-benzyl-3,7-diazabicyclo[3.3.0]octane;
  3-(2-pyrimidyl)-7-benzyl-3,7-diazabicyclo[3.3.0]octane; or
  3-(5,5-dimethoxy)pentyl-7-benzyl-3,7-diazabicyclo[3.3.0]octane.

2. A compound as claimed in claim 1, wherein, in the compound of formula I, the optional substituents on aryl and aryloxy groups are one or more groups selected from —OH, cyano, halo, nitro, C$_{1-6}$ alkyl (optionally terminated by —N(H)C(O)OR$^{23a}$), C$_{1-6}$ alkoxy, Het$^1$, aryl (which aryl group may not be substituted with any further aryl groups), —N(R$^{24a}$)R$^{24b}$, —C(O)R$^{24c}$, —C(O)OR$^{24d}$, —C(O)N(R$^{24e}$)R$^{24f}$, —N(R$^{24g}$)C(O)R$^{24h}$, —N(R$^{24i}$)C(O)N(R$^{24j}$)R$^{24k}$, —N(R$^{24m}$)S(O)$_2$R$^{23b}$, —S(O)$_n$R$^{23c}$, —OS(O)$_2$R$^{23d}$ and —S(O)$_2$N(R$^{24n}$)R$^{24p}$, wherein Het$^1$, R$^{23a}$ to R$^{23d}$, R$^{24a}$ to R$^{24p}$ and n are as defined in claim 1.

3. A compound as claimed in claim 1, wherein the wavy lines represent relative cis-stereochemistry.

4. A compound as claimed in claim 1, wherein R$^1$ represents C$_{1-8}$ alkyl (optionally substituted and/or terminated by one or more groups selected from halo, optionally substituted phenyl, —C(O)R$^{5a}$, —OR$^{5b}$, —C(O)OR$^7$, —C(O)N(H)R$^8$ and —S(O)$_2$—C$_{1-6}$ alkyl), —C(O)OR$^7$, or —S(O)$_2$R$^9$.

5. A compound as claimed in claim 1, wherein R$^{5a}$ and R$^{5b}$ independently represent, at each occurrence, H, C$_{1-6}$ alkyl (optionally substituted and/or terminated by one or more substituents selected from —OH, C$_{1-4}$ alkoxy and halo), or optionally substituted phenyl.

6. A compound as claimed in claim 1, wherein R$^7$ represents, at each occurrence, C$_{1-8}$ alkyl (which group is optionally substituted and/or terminated by one or more substituents selected from —OH, halo, cyano, optionally substituted phenyl, C$_{1-4}$ alkoxy, —SO$_2$R$^{13a}$, and —C(O)R$^{13b}$.

7. A compound as claimed in claim 6, wherein R$^{13a}$ and R$^{13b}$ independently represent C$_{1-6}$ alkyl.

8. A compound as claimed in claim 1, wherein R$^8$ represents, at each occurrence, C$_{1-8}$ alkyl (which group is optionally substituted and/or terminated by one or more substituents selected from —OH, halo, cyano and C$_{1-4}$ alkoxy), —D-(optionally substituted phenyl), —D—S(O)$_2$R$^{15a}$, —D—C(O)—C$_{1-6}$alkyl or —D—C(O)OR$^{15b}$.

9. A compound as claimed in claim 8, wherein R$^{15a}$ and R$^{15b}$ independently represent C$_{1-6}$ alkyl (optionally substituted and/or terminated by one or more substituents selected from halo, cyano and optionally substituted phenyl) or optionally substituted phenyl.

10. A compound as claimed in claim 1, wherein D represents a direct bond or C$_{1-3}$ alkylene.

11. A compound as claimed in claim 1, wherein R$^9$ represents, at each occurrence, C$_{1-5}$ alkyl (optionally substituted and/or terminated by one or more substituents selected from halo, cyano and optionally substituted phenyl) or optionally substituted phenyl.

12. A compound as claimed in claim 1, wherein R$^2$ represents H, C$_{1-2}$ alkyl, —OR$^{16}$, —N(H)R$^{17}$ or, together with R$^3$, represents =O.

13. A compound as claimed in claim 1, wherein R$^3$ represents H, C$_{1-2}$ alkyl or, together with R$^2$, represents =O.

14. A compound as claimed in claim 1, wherein R$^{16}$ represents H, C$_{1-4}$ alkyl, —E-optionally substituted phenyl, —C(O)R$^{9a}$ or —C(O)N(H)R$^{20a}$.

15. A compound as claimed in claim 1, wherein R$^{17}$ represents H, C$_{1-4}$ alkyl, —E-optionally substituted phenyl, —C(O)R$^{19a}$ or —C(O)OR$^{19b}$.

16. A compound as claimed in claim 1, wherein R$^{19a}$ and R$^{19b}$ independently represent, at each occurrence, C$_{1-6}$ alkyl, or optionally substituted phenyl.

17. A compound as claimed in claim 1, wherein R$^{20a}$ represents H or C$_{1-4}$ alkyl.

18. A compound as claimed in claim 1, wherein E represents, at each occurrence, a direct bond or C$_{1-2}$ alkylene.

19. A compound as claimed in claim 1, wherein A represents —G—.

20. A compound as claimed in claim 1, wherein B represents —Z—, —Z—S(O)$_n$—, —Z—O— (in which latter two groups, Z is attached to the carbon atom bearing R$^2$ and R$^3$).

21. A compound as claimed in claim 19, wherein G represents C$_{1-5}$ alkylene.

22. A compound as claimed in claim 1, wherein Z represents a direct bond or C$_{1-3}$ alkylene.

23. A compound as claimed in claim 1, wherein R$^4$ represents phenyl optionally substituted by one or more substituents selected from cyano, halo, nitro, C$_{1-4}$ alkyl (optionally terminated by —N(H)C(O)OR$^{23a}$), C$_{1-4}$ alkoxy, optionally substituted phenyl, —C(O)N(H)R$^{24e}$, —N(H)C(O)R$^{24h}$, —N(H)C(O)N(H)R$^{24j}$, —N(H)S(O)$_2$R$^{23b}$, —S(O)$_2$R$^{23c}$ and —S(O)$_2$N(R$^{24n}$)R$^{24p}$.

24. A compound as claimed in claim 1, wherein R$^a$ to R$^f$ independently represent H or C$_{1-2}$ alkyl.

25. A compound as claimed in claim 1, wherein optional substituents on phenyl groups are one or more groups selected from —OH, cyano, halo, nitro, C$_{1-4}$ alkyl (optionally terminated by —N(H)C(O)OR$^{23a}$), C$_{1-4}$ alkoxy, —NH$_2$, —C(O)R$^{24c}$, —C(O)OR$^{24d}$, —C(O)N(H)R$^{24e}$, —N(H)C(O)R$^{24h}$, —N(H)C(O)N(H)R$^{24j}$, N(H)S(O)$_2$R$^{23b}$, —S(O)$_n$R$^{23c}$ and —S(O)$_2$N(R$^{24n}$)R$^{24p}$.

26. A compound as claimed in claim 25, wherein and R$^{23a}$ to R$^{23c}$, R$^{24c}$, R$^{24d}$, R$^{24e}$, R$^{24h}$, R$^{24j}$, R$^{24n}$ and R$^{24p}$ independently represent C$_{1-4}$ alkyl.

27. A compound as claimed in claim 1, wherein n represents 0 or 2.

28. A compound as claimed in claim 1, wherein alkyl groups and alkoxy groups may be, unless otherwise specified:

(i) straight- or branched-chain or cyclic or part cyclic/acyclic;
  (ii) saturated or unsaturated;
  (iii) interrupted by one or more oxygen atoms; and/or
  (iv) substituted by one or more fluoro or chloro atoms.

29. A pharmaceutical formulation including a compound as defined in any one of claims 1 to 23 or 24 to 28 in admixture with a pharmaceutically-acceptable adjuvant, diluent or carrier.

* * * * *

UNITED STATES PATENT AND TRADEMARK OFFICE
CERTIFICATE OF CORRECTION

PATENT NO. : 7,144,914 B2
APPLICATION NO. : 10/467043
DATED : December 5, 2006
INVENTOR(S) : William Brown et al.

It is certified that error appears in the above-identified patent and that said Letters Patent is hereby corrected as shown below:

Column 55, Claim 1, Line 26, "$C_{1-2}$" should read -- $C_{1-12}$ --.

Column 55, Claim 1, Line 57, "$R_{3\ 18}$" should read -- $R_{18}$ --.

Column 57, Claim 14, Line 48, "$C(O)R9_a$" should read -- $C(O)R19_a$ --.

Signed and Sealed this

Sixteenth Day of June, 2009

JOHN DOLL
*Acting Director of the United States Patent and Trademark Office*